(12) United States Patent
Raju et al.

(10) Patent No.: US 10,881,434 B2
(45) Date of Patent: Jan. 5, 2021

(54) BONE SCREW

(71) Applicant: VERTISCREW, LLC, Dover, DE (US)

(72) Inventors: Muralidhara Rudhra Raju, Fountain Valley, CA (US); Amir Ali Akhavi, Irvine, CA (US)

(73) Assignee: VertiScrew, LLC, Dover, DE (US)

( * ) Notice: Subject to any disclaimer, the term of this patent is extended or adjusted under 35 U.S.C. 154(b) by 275 days.

(21) Appl. No.: 15/230,190

(22) Filed: Aug. 5, 2016

(65) Prior Publication Data

US 2016/0338741 A1 Nov. 24, 2016

Related U.S. Application Data

(63) Continuation of application No. 14/175,058, filed on Feb. 7, 2014, now Pat. No. 9,451,991, and a
(Continued)

(51) Int. Cl.
*A61B 17/70* (2006.01)
*A61B 17/88* (2006.01)
*A61B 17/86* (2006.01)

(52) U.S. Cl.
CPC ...... *A61B 17/7035* (2013.01); *A61B 17/7032* (2013.01); *A61B 17/7085* (2013.01);
(Continued)

(58) Field of Classification Search
CPC . A61B 17/70; A61B 17/7001; A61B 17/7032; A61B 17/7034; A61B 17/7035;
(Continued)

(56) References Cited

U.S. PATENT DOCUMENTS

| 5,443,467 A | 8/1995 | Biedermann et al. |
| 5,586,984 A | 12/1996 | Errico et al. |

(Continued)

OTHER PUBLICATIONS

Biomet. Lineum OCT Spine System. Printed Apr. 4, 2014. http://www.biomet.com/wps/wcm/connect/internet/2d66d094-1a55-40fb-8fec-6e84929ad752/Lineum+OCT+Spine+System+Surgical+Technique.pdf?MOD=AJPERES&CACHEID=2d66d094-1a55-40fb-8fec-6e84929ad752 44 pages.

(Continued)

*Primary Examiner* — Lynnsy M Summitt
(74) *Attorney, Agent, or Firm* — Rimas T. Lukas

(57) ABSTRACT

A bone fixation system with variable z-axis translation is provided. The bone fixation system includes an outer tulip coupled to a bone fastener. An inner tulip, which provides a seat for an elongate fixation rod, is located inside the outer tulip. The inner tulip together with a seated rod is permitted to translate along the z-axis in an unlocked position. Also in the unlocked position, the bone fastener is free to angulate relative to the outer tulip. The bone fixation system includes a locked position in which the z-axis position of the inner tulip and rod relative to the outer tulip is fixed. Also in the locked position, the bone fastener is locked with respect to the outer tulip. The system may be adjusted between the locked and unlocked positions by way of a set screw or independently by rotation of the inner tulip relative to the outer tulip.

12 Claims, 32 Drawing Sheets

Related U.S. Application Data continuation of application No. 14/175,065, filed on Feb. 7, 2014, now Pat. No. 9,463,047.

(60) Provisional application No. 61/762,854, filed on Feb. 9, 2013.

(52) U.S. Cl.
CPC ...... *A61B 17/7086* (2013.01); *A61B 17/7091* (2013.01); *A61B 17/862* (2013.01); *A61B 17/8883* (2013.01)

(58) Field of Classification Search
CPC ............ A61B 17/7037; A61B 17/7038; A61B 17/7041; A61B 17/7046
See application file for complete search history.

(56) References Cited

U.S. PATENT DOCUMENTS

| | | | |
|---|---|---|---|
| 7,588,593 B2 | 9/2009 | Aferzon | |
| 7,635,380 B2 | 12/2009 | Zucherman et al. | |
| 7,662,172 B2 | 2/2010 | Warnick | |
| 7,766,946 B2 | 8/2010 | Bailly | |
| 7,828,829 B2 | 11/2010 | Ensign | |
| 7,862,588 B2 | 1/2011 | Abdou | |
| 8,029,539 B2 | 10/2011 | Kirschman | |
| 8,048,124 B2 * | 11/2011 | Chin | A61B 17/7032 606/264 |
| 8,100,947 B2 | 1/2012 | Ensign | |
| 8,123,782 B2 | 2/2012 | Altarac et al. | |
| 8,221,472 B2 | 7/2012 | Peterson | |
| 8,236,035 B1 * | 8/2012 | Bedor | A61B 17/7037 606/328 |
| 8,308,782 B2 | 11/2012 | Jackson | |
| 8,361,123 B2 | 1/2013 | Fanger | |
| 8,663,289 B2 | 3/2014 | Scwab | |
| 8,808,330 B2 | 8/2014 | Biedermann | |
| 8,951,294 B2 | 2/2015 | Gennari | |
| 9,439,700 B2 | 9/2016 | Peterson | |
| 2006/0161152 A1 | 7/2006 | Ensign | |
| 2010/0249846 A1 | 9/2010 | Simonson | |
| 2010/0305620 A1 | 12/2010 | Gotfried | |
| 2011/0106178 A1 | 5/2011 | Schwab | |
| 2011/0112578 A1 | 5/2011 | Keiser et al. | |
| 2011/0282399 A1 | 11/2011 | Jackson | |
| 2012/0016425 A1 | 1/2012 | Shaffrey et al. | |
| 2012/0130436 A1 * | 5/2012 | Haskins | A61B 17/7032 606/305 |
| 2014/0358182 A1 | 12/2014 | Puekert | |
| 2015/0134006 A1 | 5/2015 | Ziolo et al. | |
| 2015/0196338 A1 | 7/2015 | Biedermann | |

OTHER PUBLICATIONS

Scoliosisnutty.com. Medtronic TSRH-3D system. Printed Apr. 4, 2014. http://www.scoliosisnutty.com/tsrh.php 2 pages.

* cited by examiner

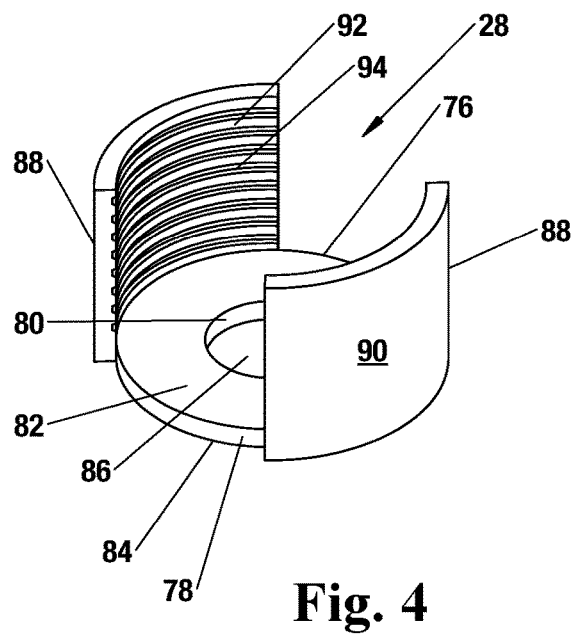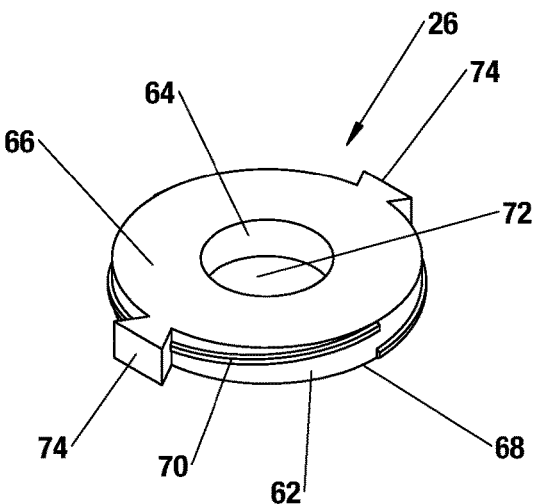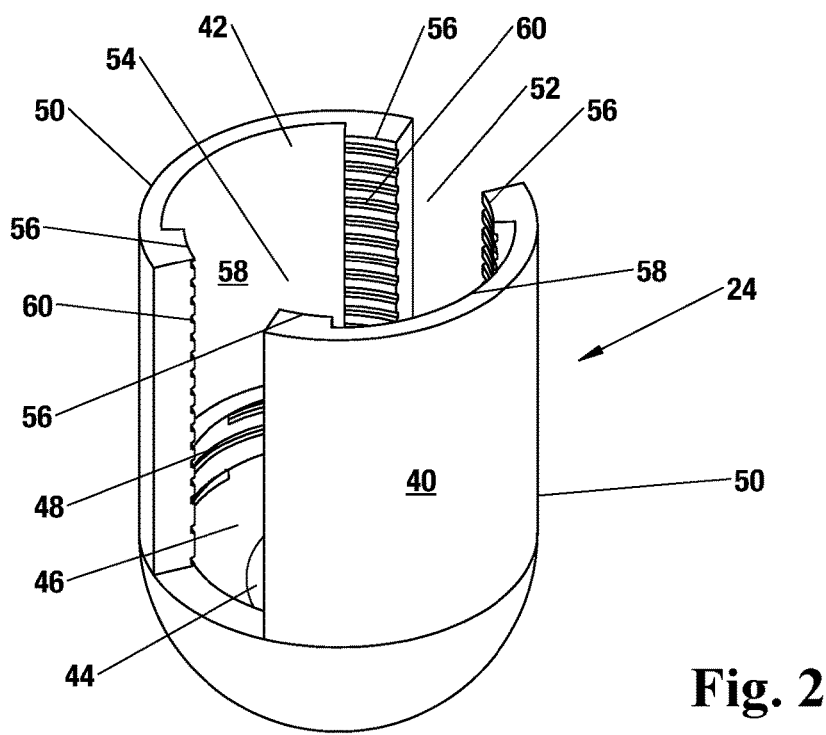
Fig. 4
Fig. 3
Fig. 2

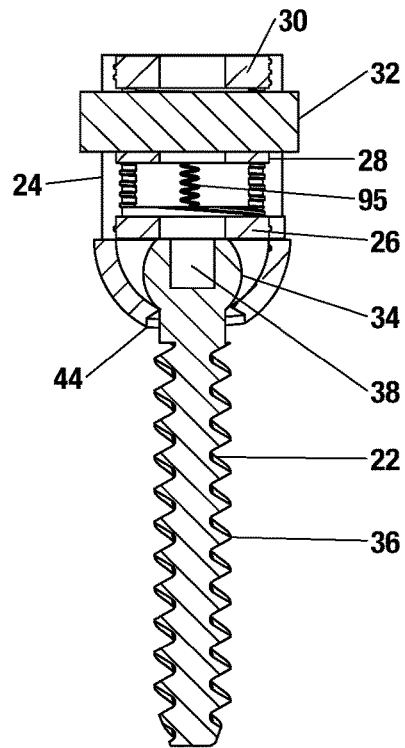
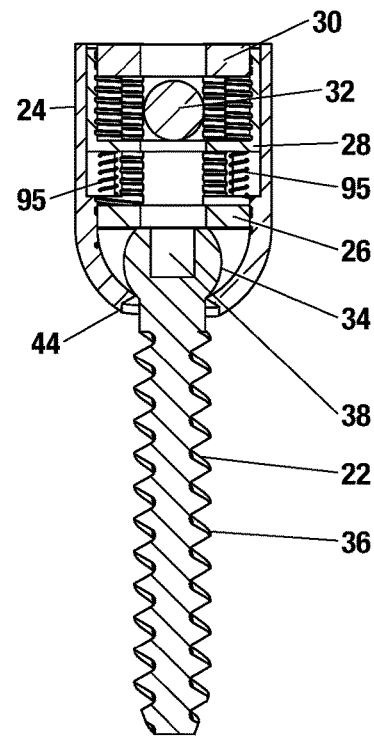
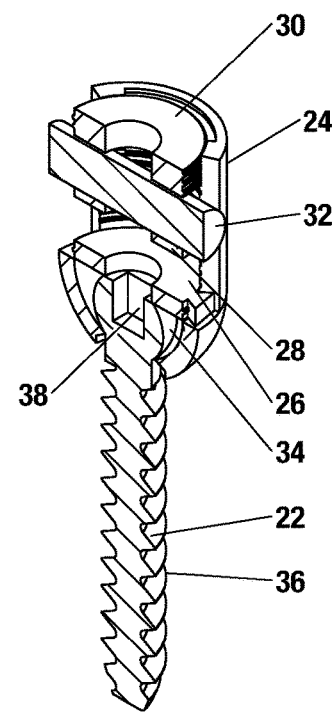
Fig. 5B　　　Fig. 6B　　　Fig. 7B
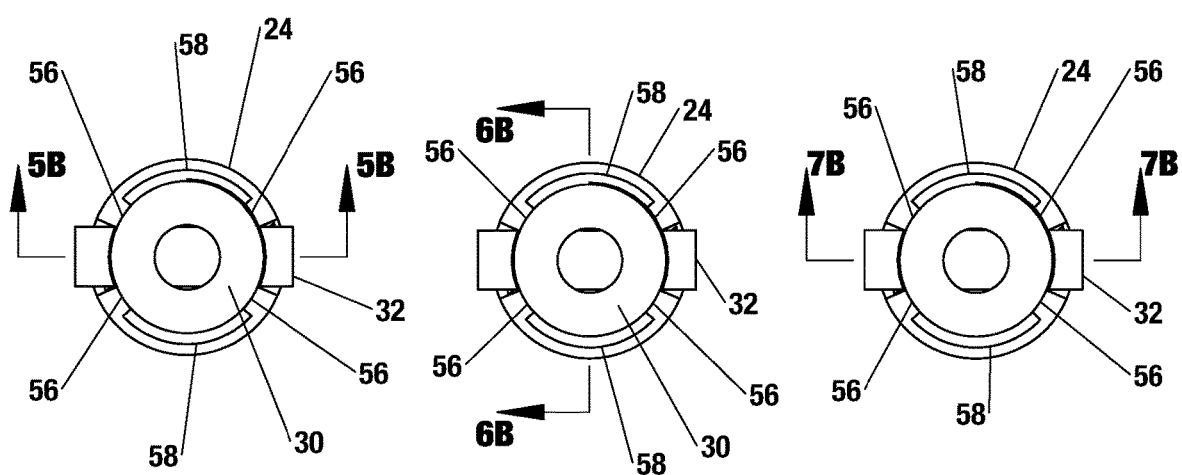
Fig. 5A　　　Fig. 6A　　　Fig. 7A

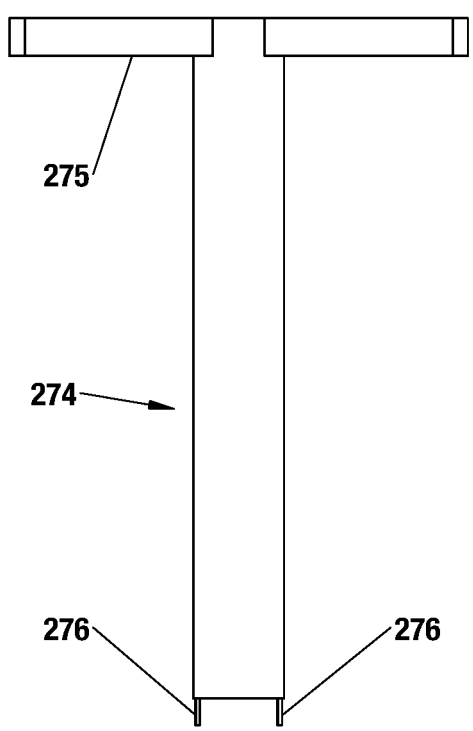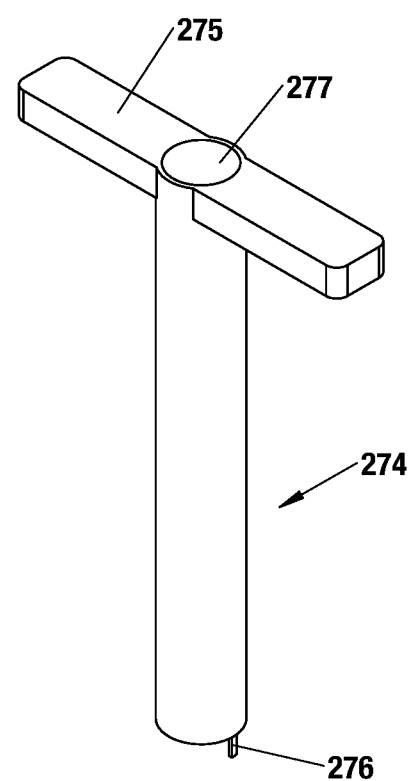
Fig. 29B
Fig. 29A

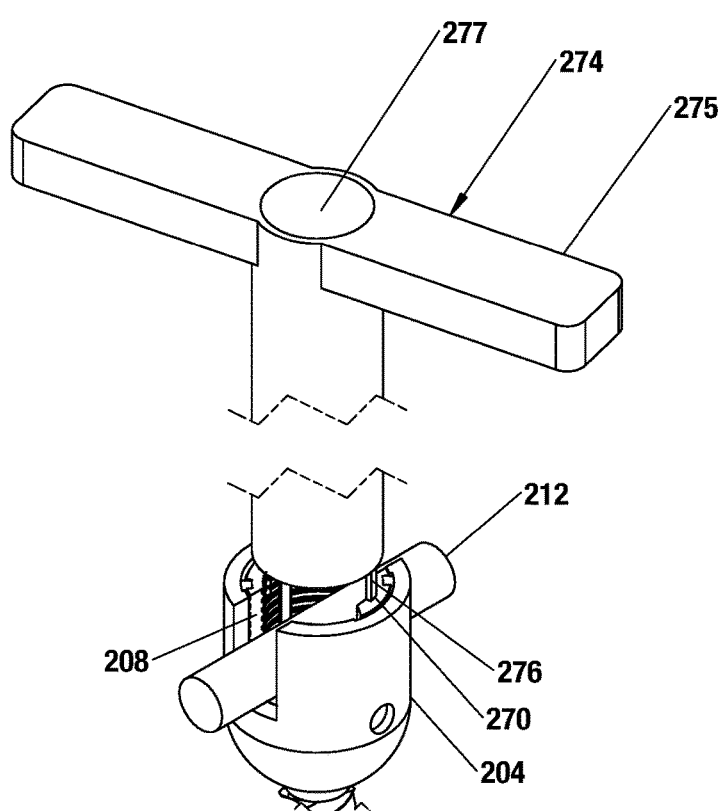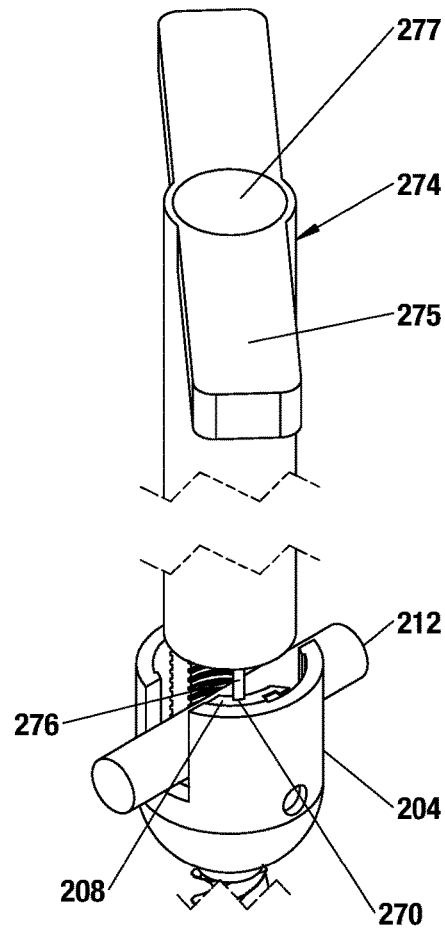
Fig. 31B
Fig. 32B

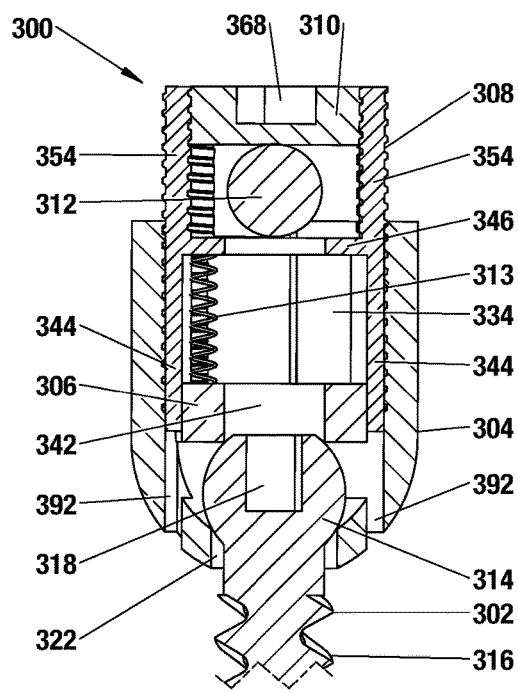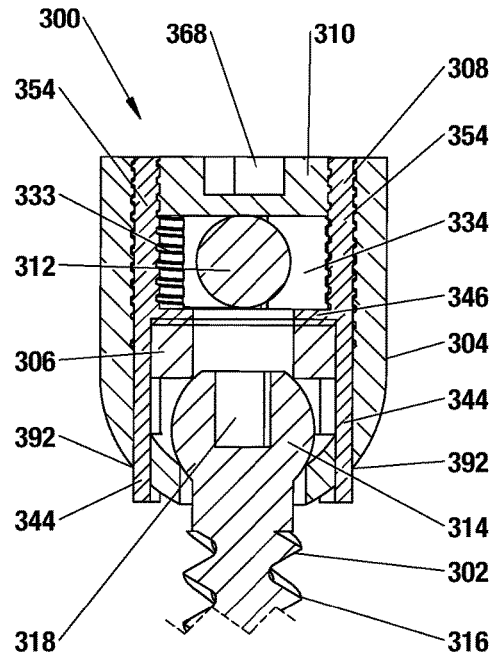
Fig. 40B  Fig. 39B
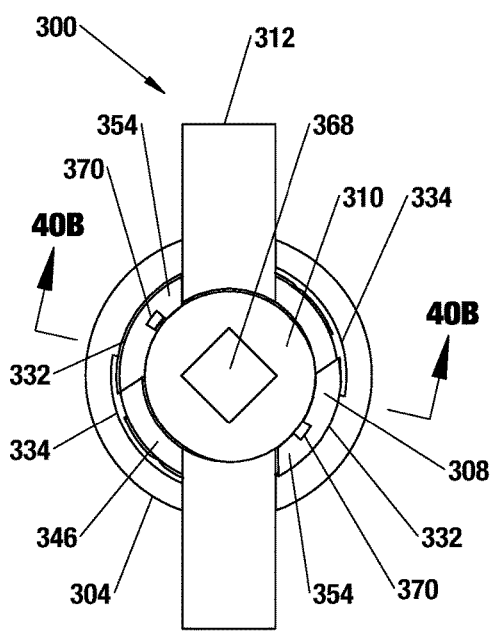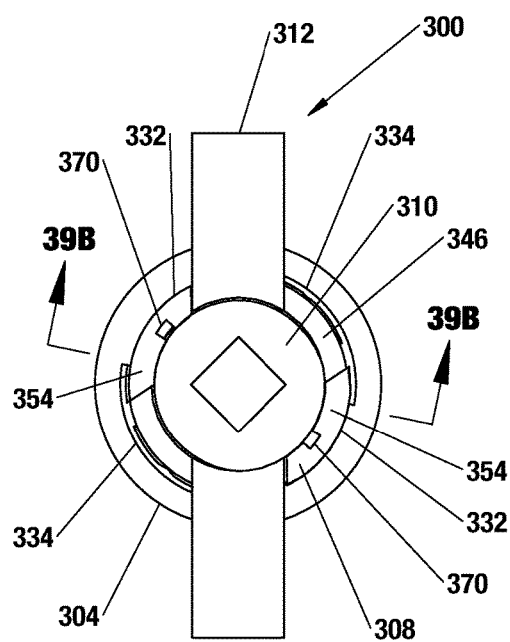
Fig. 40A  Fig. 39A

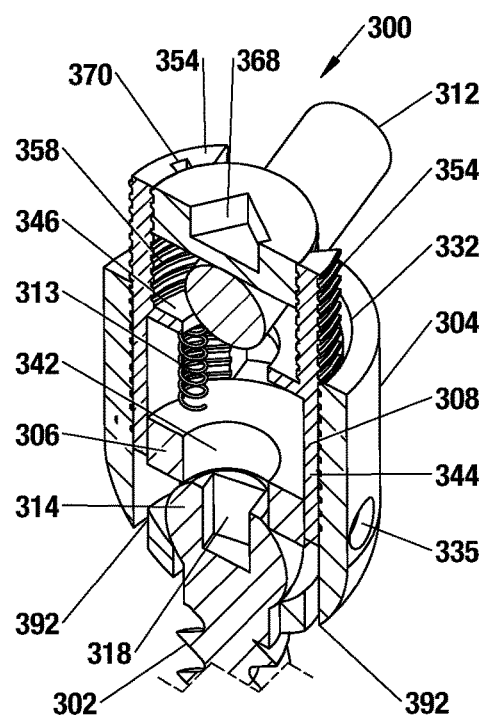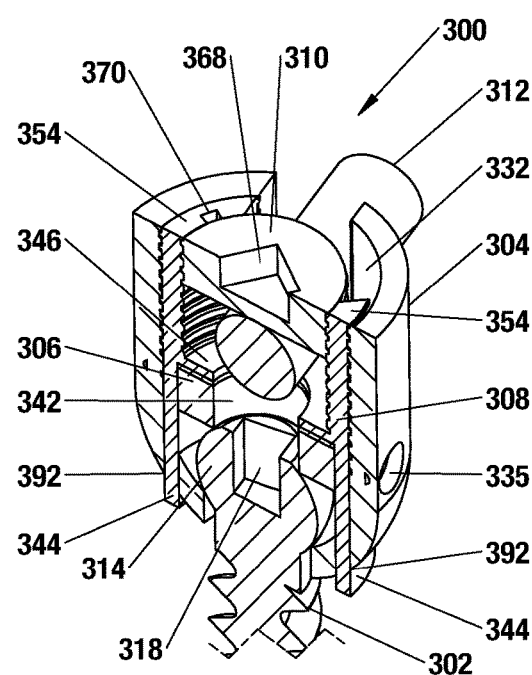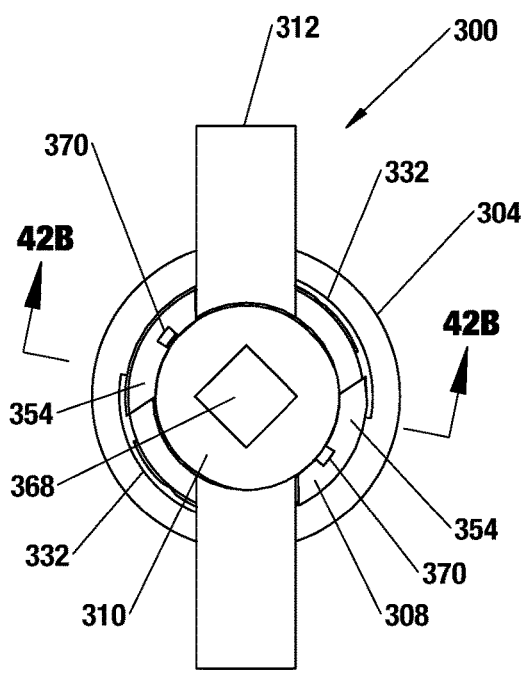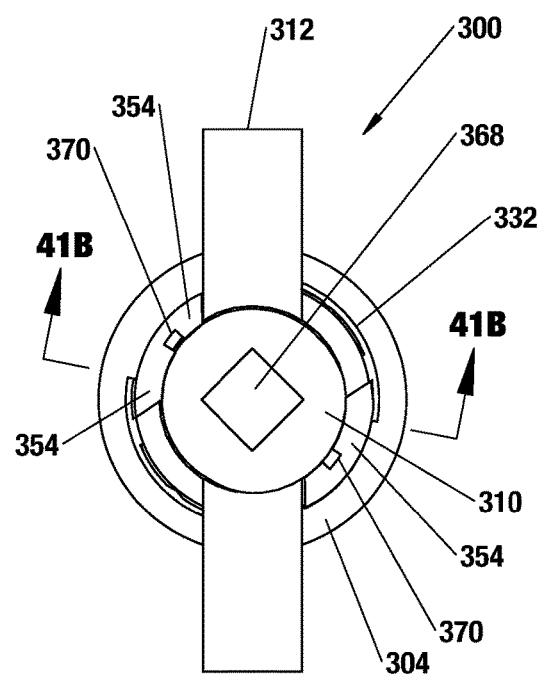
Fig. 42B
Fig. 41B
Fig. 42A
Fig. 41A

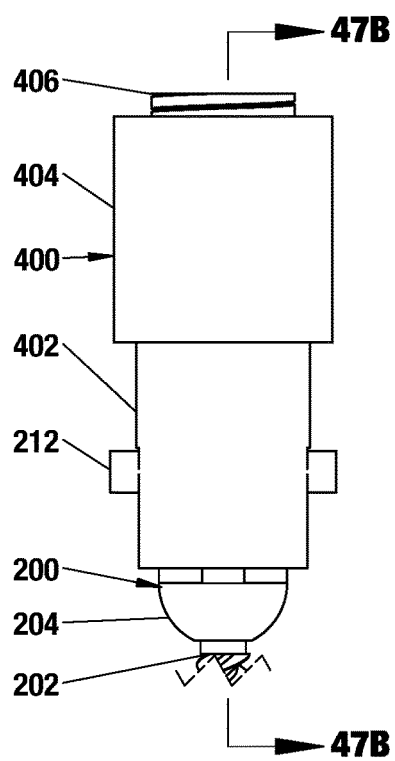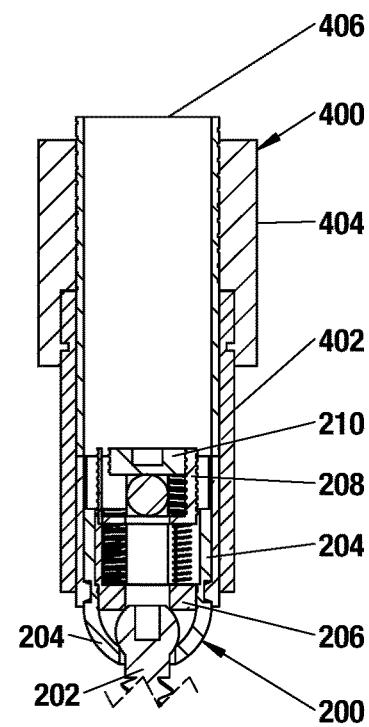
Fig. 47A    Fig. 47B
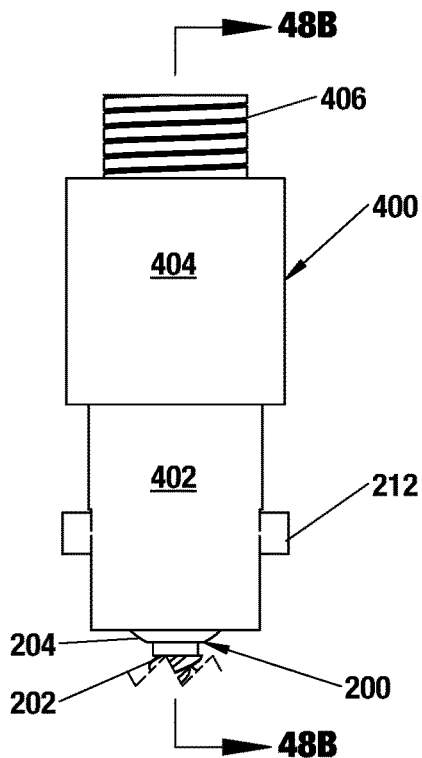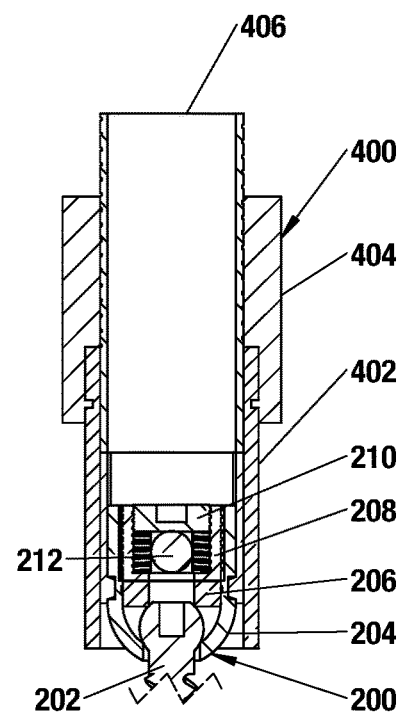
Fig. 48A    Fig. 48B

BONE SCREW

CROSS-REFERENCE TO RELATED APPLICATION

This application is a continuation of U.S. patent application Ser. No. 14/175,058 filed on Feb. 7, 2014 entitled "Bone screw" which claims priority to and benefit of U.S. Provisional Patent Application Ser. No. 61/762,854 entitled "Threaded bone screw with variable Z-axis translation" filed on Feb. 9, 2013, this application is also a continuation of U.S. patent application Ser. No. 14/175,065 filed on Feb. 7, 2014 entitled "Bone screw" which claims priority to and benefit of U.S. Provisional Patent Application Ser. No. 61/762,854 entitled "Threaded bone screw with variable Z-axis translation" filed on Feb. 9, 2013, all of which are incorporated by reference in their entirety herein.

FIELD OF THE INVENTION

The present invention is directed to surgical devices and methods, and in particular, to bone fixation devices used in spinal surgery.

BACKGROUND OF THE INVENTION

Spinal fusion is a common surgical procedure used to correct numerous disease states including degenerative disorders, trauma, instability, and deformity. A frequent method of fusion entails the use of bone screws placed through various sections of the vertebral body including the body, pedicle, facets, lamina, lateral masses, and/or transverse processes. These screws are then linked rigidly with a rod, plate or other fixation device to immobilize the vertebral segments.

Due to the variation in a patient's anatomy and differences in screw placement technique, screws are often not perfectly aligned which makes securement of a fixation device more difficult. To solve this, many screws that have a threaded shank portion incorporate an articulating tulip or receiver connected to the proximal end of the shank portion, such as in a polyaxial or multi-axial bone screw. Polyaxial bone screws allow for a variation in the angulation of the tulip/receiver relative to the shank portion in order to allow the tulip/receiver to more closely align for receiving a fixation device such as a fixation rod within the tulip/receiver. Some bone screws allow for the lateral translation of the tulip/receiver relative to its point of fixation. Further alignment may be accomplished by contouring of the fixation device itself to compensate for any remaining misalignment. For example, if a fixation rod is employed, the rod is bent to conform to the patient anatomy and location of the tulip/receiver to securely attach thereto.

A body in three-dimensional space has six degrees of freedom, namely, translation through the perpendicular x, y, and z planes, combined with the rotation through the three perpendicular axes (pitch, yaw, and roll). Typical articulating polyaxial screws allow three dimensional rotations (pitch, yaw, and roll). Some designs also incorporate lateral x-plane translation. Longitudinal translation (y-plane), generally along the cephalad-caudal direction or axis of the fixating rod or plate, is usually accomplished by fixing the tulip/receiver to different positions along the rod or plate.

Anterior/posterior translation (along the z-plane) is typically accomplished by persuading the vertebral body itself, using instruments to raise or lower the vertebral body until the tulip/receiver is properly aligned with the rod or plate. Frequently, however, this anterior/posterior translation may not be desirable as it may produce suboptimal alignment of the vertebral bodies or even cause fractures of the bone or pullout of the shank portion of the screw from the bone due to the stresses placed on it during the persuading process. The other option for adjustment along the z-axis employed is to partially back out the screw, leaving it proud. This, however, reduces the bone-screw interface thereby weakening the overall strength of the construct. Some designs, such as the one illustrated in U.S. Pat. No. 7,588,593, allow for vertical adjustment but require manual assembly of the screw and head construct during surgery. Hence, there is a need for modular bone screw assemblies that can provide variable angle orientation together with z-axis translation which are easy to assemble.

SUMMARY OF THE INVENTION

According to one aspect of the invention, a bone fixation system is provided. The bone fixation system includes a bone fastener having a bone engaging portion and a head connected to the bone engaging portion. The system includes an outer receiver having a proximal end, a distal end and a longitudinal axis. The outer receiver includes a sidewall extending between the proximal end and the distal end and having an inner surface and an outer surface. An inner bore extends through the outer receiver between a top opening at the proximal end and a bottom opening at the distal end. The bone fastener is connected to the outer receiver such that the bone engaging portion extends through the bottom opening. The outer receiver includes two oppositely disposed arms that are defined by the sidewall and at least one rod channel that is defined between the two arms. The at least one rod channel is interconnected with the top opening and the inner bore. The inner surface of each arm has a longitudinally extending interlocking surface adjacent to a longitudinally extending smooth surface. The interlocking surface of one arm is opposite from the interlocking surface of the other arm and the smooth surface of one arm is opposite from the smooth surface of the other arm. The outer receiver further includes an interlocking inner surface at the distal end. The bone fixation system further includes a first locking cap located inside the inner bore of the outer receiver. The first locking cap has an interlocking outer surface configured to interlock with the interlocking inner surface at the distal end of the outer receiver. The first locking cap has at least one upwardly extending tab. The bone fixation system further includes an inner receiver that is sized to fit inside the outer receiver. The inner receiver includes a base and two oppositely disposed arms extending upwardly from the base. The inner receiver includes at least one channel defined between the arms. Each arm has an interlocking inner surface and an interlocking outer surface. The interlocking outer surface of each arm of the inner receiver is configured to engage the interlocking surfaces on the arms of the outer receiver. The inner receiver is coupled to the first locking cap by the at least one tab. A second locking cap is removably located between the arms of the inner receiver and has an interlocking outer surface configured to interlock with the interlocking inner surface of the arms of the inner receiver. The bone fixation system includes an unlocked position in which the bone fastener angulates with respect to the outer receiver and the inner receiver is free to translate longitudinally with respect to the outer receiver; and a locked position in which the bone fastener and inner receiver are fixed with respect to the outer receiver.

According to another aspect of the invention, a bone fixation system is provided. The bone fixation system includes a bone fastener having a bone engaging portion and a head integrally connected to the bone engaging portion. The system includes an outer receiver having a proximal end, a distal end and a longitudinal axis. The outer receiver has a sidewall extending between the proximal end and the distal end and an inner surface and an outer surface. The outer receiver includes an inner bore extending between a top opening at the proximal end and a bottom opening at the distal end. The bone fastener is connected to the outer receiver such that the bone engaging portion extends through the bottom opening. The outer receiver includes two oppositely disposed arms defined by the sidewall and at least one rod channel defined between the two arms. The at least one rod channel is interconnected with the top opening and the inner bore. The inner surface of each arm of the outer receiver has a longitudinally extending interlocking inner surface adjacent to a longitudinally extending smooth surface. The interlocking inner surface of one arm is opposite from the interlocking inner surface of the other arm and the smooth surface of one arm is opposite from the smooth surface of the other arm. The outer receiver includes an interlocking inner surface at the distal end. The bone fixation system further includes a first locking cap located inside the inner bore of the outer receiver. The first locking cap has an interlocking outer surface configured to interlock with the interlocking inner surface at the distal end. The outer surface of the first locking cap is interconnected by a top surface and a bottom surface. The first locking cap includes two tab-engaging surfaces. The bone fixation system further includes an inner receiver sized to fit inside the outer receiver. The inner receiver includes a base and two oppositely disposed arms extending upwardly from the base. The inner receiver includes at least one channel defined between the arms and each arm has an interlocking inner surface and an interlocking outer surface. The interlocking outer surface of each arm of the inner receiver is configured to engage the interlocking inner surfaces on the arms of the outer receiver. The inner receiver further includes two oppositely disposed tabs extending downwardly from the base. The two tabs are configured for engagement with the two tab-engaging surfaces on the first locking cap. The inner receiver is coupled to the first locking cap by the two tabs engaging the tab-engaging surfaces. The bone fixation system further includes a second locking cap removably located between the arms of the inner receiver and having an interlocking outer surface configured to interlock with the interlocking inner surface of the arms of the inner receiver. The bone fixation system includes an unlocked position in which the bone fastener angulates with respect to the outer receiver and the inner receiver is free to translate longitudinally with respect to the outer receiver and a locked position in which the bone fastener and inner receiver are fixed with respect to the outer receiver.

According to another aspect of the invention, a bone fixation system is provided. The bone fixation system includes an outer receiver having an inner bore and an open proximal end and an inner receiver having an inner bore and an open proximal end. The inner receiver is located inside an outer receiver. The inner receiver is movable along a longitudinal axis relative to the outer receiver in an unlocked position and the inner receiver is longitudinally fixed relative to the outer receiver in a locked position. Converting between the locked and unlocked positions is achieved by rotation of the inner receiver relative to the outer receiver.

According to another aspect of the invention, a bone fixation system is provided. The bone fixation system includes an outer receiver having a sidewall that defines an inner bore and an open proximal end. The sidewall has an inner surface and an outer surface that defines at least one channel opening to the inner bore and the open proximal end. The outer receiver includes an interlocking inner surface formed on the inner surface. The bone fixation system further includes an inner receiver including a sidewall that defines an interior, an open proximal end, and an inner base at a distal end. The sidewall has an inner surface and an outer surface that defines at least one channel opening to the interior and the open proximal end. The inner receiver includes an interlocking inner surface formed on the inner surface and an interlocking outer surface formed on the outer surface. The inner receiver is located inside the outer receiver such that the at least one channel of the inner receiver is substantially aligned with the at least one channel of the outer receiver. The inner receiver is movable along a longitudinal axis relative to the outer receiver in an unlocked position. A rod is disposed inside the at least one channel of the inner receiver. The bone fixation system further includes a first locking cap having an interlocking outer surface. The first locking cap is located in the inner receiver such that the interlocking outer surface of the first locking cap is interlocked with the interlocking inner surface of the inner receiver in a first locked position. The rod is located between the inner base and the first locking cap and the inner receiver is free to translate longitudinally in the first locked position.

According to another aspect of the invention, a bone fixation system is provided. The bone fixation system includes a bone fastener having a bone engaging portion and a head integrally connected to the bone engaging portion. The bone fixation system further includes an outer receiver having a proximal end, a distal end and a longitudinal axis. The outer receiver has a sidewall extending between the proximal end and the distal end and an inner surface and an outer surface. An inner bore extends between a top opening at the proximal end and a bottom opening at the distal end of the outer receiver. The bone fixation system further includes a bone fastener connected to the outer receiver such that the bone engaging portion extends through the bottom opening. Two oppositely disposed arms are defined by the sidewall of the outer receiver and at least one rod channel is defined between the two arms. The at least one rod channel is interconnected with the top opening and the inner bore. The inner surface of each arm has a longitudinally extending interlocking inner surface adjacent to a longitudinally extending smooth surface. The interlocking inner surface of one arm is opposite from the interlocking inner surface of the other arm and the smooth surface of one arm is opposite from the smooth surface of the other arm. The outer receiver further includes an interlocking inner surface at the distal end. The bone fixation system further includes a first locking cap located inside the inner bore of the outer receiver. The first locking cap has an interlocking outer surface configured to interlock with the interlocking inner surface at the distal end of the outer receiver. The bone fixation system further includes an inner receiver sized to fit inside the outer receiver. The inner receiver includes a base and two oppositely disposed arms extending upwardly from the base. The inner receiver includes at least one channel between the arms. Each arm has an interlocking inner surface. The inner receiver is located inside the inner bore of outer receiver such that the oppositely disposed arms of the inner receiver are disposed in the location of the smooth surfaces and the interlocking inner surface of each arm is flush with the adjacent interlocking surfaces of the outer receiver. The bone fixation system further includes a second locking cap located between the arms of the inner receiver. The second locking cap has an interlocking outer surface configured to interlock with both the interlocking inner surface of the arms of the inner receiver and the adjacent interlocking inner surface of the arms of the outer receiver. The inner receiver includes an unlocked position in which the inner receiver is free to translate longitudinally with respect to the outer receiver and a locked position in which the inner receiver is fixed with respect to the outer receiver. The locked position is achieved by the interlocking outer surface of the second locking cap engaging both the interlocking inner surface of the outer receiver and the interlocking inner surface of the inner receiver.

According to another aspect of the invention, a bone fixation system is provided. The bone fixation system includes an outer receiver. The outer receiver has a sidewall that defines an inner bore and an open proximal end. The sidewall has an inner surface and an outer surface that defines at least one channel opening to the inner bore and the open proximal end. The outer receiver includes an interlocking inner surface formed on the inner surface. The bone fixation system further includes an inner receiver. The inner receiver has a sidewall that defines an interior, an open proximal end, and an inner base at a distal end. The sidewall of the inner receiver has an inner surface and an outer surface that defines at least one channel opening to the interior and the open proximal end. The inner receiver includes an interlocking inner surface formed on the inner surface. The inner receiver is located inside the outer receiver such that the at least one channel of the inner receiver is substantially aligned with the at least one channel of the outer receiver. The inner receiver is movable along a longitudinal axis relative to the outer receiver in an unlocked position. The bone fixation system further includes a locking cap having an interlocking outer surface. The locking cap is located in the inner receiver and interlocked with the interlocking inner surface of the outer receiver and the interlocking inner surface of the inner receiver in a locked position wherein longitudinal translation of the inner receiver is fixed relative to the outer receiver.

According to another aspect of the invention, a bone fixation system is provided. The bone fixation system includes an outer receiver. The outer receiver has a sidewall that defines an inner bore and an open proximal end. The sidewall has an inner surface and an outer surface that defines at least one channel opening to the inner bore and the open proximal end. The outer receiver includes an interlocking outer surface formed on the outer surface. The bone fixation system further includes an inner receiver. The inner receiver has a sidewall that defines an interior, an open proximal end, and an inner base at a distal end. The sidewall has an inner surface and an outer surface that defines at least one channel opening to the interior and the open proximal end. The inner receiver includes an interlocking inner surface formed on the inner surface. The inner receiver is located inside the outer receiver such that the at least one channel of the inner receiver is substantially aligned with the at least one channel of the outer receiver. The inner receiver is movable along a longitudinal axis relative to the outer receiver in an unlocked position. The bone fixation system includes a locking cap. The locking cap has an interlocking outwardly-facing surface and an interlocking inwardly-facing surface. The interlocking outwardly-facing surface is movable independently and relative to the interlocking inwardly-facing surface. The interlocking outwardly-facing surface is located in the inner receiver and interlocked with the interlocking inner surface of the inner receiver in a first locked position. The interlocking inwardly-facing surface is interlocked with the interlocking outer surface of the outer receiver in a second locked position. The second locked position prevents the longitudinal translation of the inner receiver relative to the outer receiver.

According to another aspect of the invention, a bone fixation system is provided. The bone fixation system includes a bone fastener having a bone-engaging portion and a head integrally connected to the bone-engaging portion. The bone fixation system further includes an outer receiver having a proximal end, a distal end and a longitudinal axis. The outer receiver includes a sidewall extending between the proximal end and the distal end. The outer receiver has an inner surface and an outer surface and an inner bore extending between a top opening at the proximal end. The outer receiver includes a bottom opening at the distal end. The bone fastener is connected to the outer receiver such that the bone-engaging portion extends through the bottom opening. The outer receiver includes two oppositely disposed arms defined by the sidewall and at least one rod channel defined between the two arms. The at least one rod channel is interconnected with the top opening and the inner bore. The outer surface of each arm has a longitudinally extending interlocking outer surface adjacent to a longitudinally extending smooth surface. The interlocking outer surface of one arm is opposite from the interlocking outer surface of the other arm and the smooth surface of one arm is opposite from the smooth surface of the other arm. The outer receiver includes an interlocking inner surface at the distal end. The bone fixation system includes a first locking cap located inside the inner bore of the outer receiver. The first locking cap has an interlocking outer surface configured to interlock with the interlocking inner surface at the distal end of the outer receiver. The bone fixation system further includes inner receiver that includes a base and two oppositely disposed arms extending upwardly from the base. At least one channel is defined between the arms. Each arm has an interlocking inner surface. The inner receiver is located inside the inner bore of the outer receiver. The bone fixation system includes a second locking cap having an outer surface and inner surface interconnected by a top surface and a bottom surface. The second locking cap has two oppositely disposed, downwardly extending legs; each leg has an interlocking inner surface configured to engage the longitudinally extending interlocking outer surface of each arm of the outer receiver. The second locking cap includes a cylinder configured to rotate relative to the legs. The cylinder includes an interlocking outer surface that is configured to engage with the interlocking inner surface of the inner receiver. The cylinder is connected to the inner receiver by engagement of the threaded outer surface of the cylinder with the threaded inner surface of the inner receiver. The inner receiver includes an unlocked position in which the inner receiver is free to translate longitudinally with respect to the outer receiver and a locked position in which the inner receiver is fixed with respect to the outer receiver. The bone fastener includes an unlocked position in which the bone fastener angulates with respect to the outer receiver and a locked position in which the bone fastener is fixed with respect to the outer receiver. The first locking cap is rotated into interlocking engagement with the interlocking surface of the interlocking inner surface at the distal end and downwardly within the inner bore of the outer receiver against the head of the bone fastener into the locked position to fix the position of the bone fastener relative to the outer receiver. The top surface of the second locking cap includes slots for engaging a tool to rotate the legs of the second locking cap between the unlocked and locked positions. The bone fixation system further includes a cover having a circular top and a plurality of downwardly extending, circumferentially located legs. The top has at least one slot configured to access the slots of the second locking cap. The bone fixation system further includes an elongate fixation rod located between the arms of the inner receiver. Rotation of the cylinder of the second locking cap downwardly onto the rod fixes the position of the rod relative to the inner receiver. In the locked position, the legs of the second locking cap are interlocked with the outer receiver.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary the dimensions of the various features are arbitrarily expanded or reduced for clarity. Included in the drawings are the following figures:

FIG. 2 is a top perspective view of an outer receiver according to the present invention.

FIG. 3 is a top perspective view of a fastener locking cap according to the present invention.

FIG. 4 is a top perspective view of an inner receiver according to the present invention.

FIG. 5A is a top view of a bone fixation system according to the present invention.

FIG. 5B is a cross-sectional view taken along line 5B-5B of FIG. 5A of a bone fixation system according to the present invention.

FIG. 6A is a top view of the bone fixation system according to the present invention.

FIG. 6B is a cross-sectional view taken along line 6B-6B of FIG. 6A of a bone fixation system according to the present invention.

FIG. 7A is a top view of a bone fixation system according to the present invention.

FIG. 7B is a cross-sectional view taken along line 7B-7B of FIG. 7A of a bone fixation system according to the present invention.

FIG. 29A is a top perspective view of a tool according to the present invention.

FIG. 29B is a side elevational view of a tool according to the present invention.

FIG. 31B is a top perspective and sectional view of a tool and bone fixation system without a set screw according to the present invention.

FIG. 32B is a top perspective and sectional view of a tool and bone fixation system without a set screw according to the present invention.

FIG. 39A is a top view of a bone fixation system according to the present invention.

FIG. 39B is a cross-sectional view taken along line 39B-39B of FIG. 39A of a bone fixation system according to the present invention.

FIG. 40A is a top view of a bone fixation system according to the present invention.

FIG. 40B is a cross-sectional view taken along line 40B-40B of FIG. 40A of a bone fixation system according to the present invention.

FIG. 41A is a top view of a bone fixation system according to the present invention.

FIG. 41B is a cross-sectional view taken along line 41B-41B of FIG. 41A of a bone fixation system according to the present invention.

FIG. 42A is a top view of a bone fixation system according to the present invention.

FIG. 42B is a cross-sectional view taken along line 42B-42B of FIG. 42A of a bone fixation system according to the present invention.

FIG. 47A is a side elevational view, sectional of a bone fixation system and rod reduction instrument according to the present invention.

FIG. 47B is a cross-sectional view taken along line 47B-47B of FIG. 47A of a bone fixation system and rod reduction instrument according to the present invention.

FIG. 48A is a side elevational, sectional view of a bone fixation system and rod reduction instrument according to the present invention.

FIG. 48B is a cross-sectional view taken along line 48B-48B of FIG. 48A of a bone fixation system and rod reduction instrument according to the present invention.

DETAILED DESCRIPTION OF THE INVENTION

Figure 1:
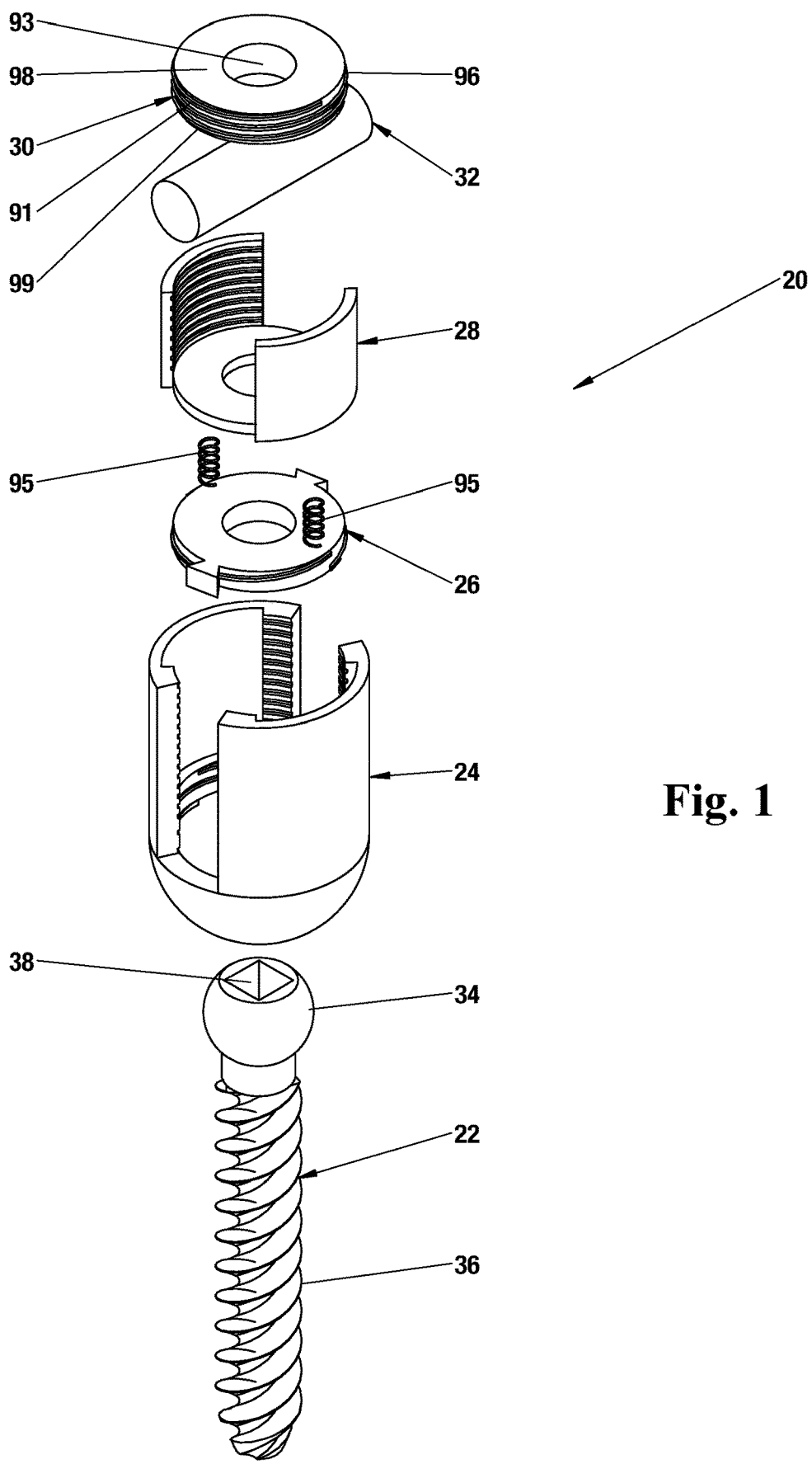
FIG. 1 is a top perspective, exploded view of a bone fixation system according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It should also be understood that the term "system", when referring to a system of the present invention, most typically refers to a set of components which includes multiple bone stabilization components such as a superior or cephalad component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intra-operatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means or fixation devices such as elongate fixation members, rods and plates but are not limited thereto. In other embodiments, components interface, in a manner that constrains their relative movement and enables the treated segment to mimic the function or partial function and/or movement or partial movement of a healthy segment. Typically, spinal interconnecting means is a dorsally positioned component, i.e., positioned posterior of the superior and inferior components, or may be a laterally positioned component, i.e., positioned to the outer side of the posterior and inferior components. The structures may include one or more struts and/or joints that provide for stabilized spinal motion. The various system embodiments may further include a band, interchangeably referred to as a ligament, which provides a tensioned relationship between the superior and inferior components and helps to maintain the proper relationship between the components.

Reference will now be made in detail to the present embodiments of the invention, examples of which are illustrated in the accompanying drawings. Wherever possible, the same reference numbers will be used throughout the drawings to refer to the same or like parts. In addition, each of the inventive embodiments described herein may be employed in a percutaneous, minimally invasive surgical procedure, a mini-open procedure or an open procedure. Utilization of minimally invasive techniques can shorten the procedure's time and speed recovery by the patient. The application of these inventions in a minimally invasive manner is not a requirement. Also, the invention is not limited to the spine and may be employed in other areas where fixation to bone is useful either in human or animal applications.

Turning to FIG. 1, there is shown a bone fixation system 20 suitable for use in orthopedic surgery. In particular, the bone fixation systems in the present invention are all adapted for use in spinal fixation procedures and as such can be installed in a patient for treating at least one or more of the following: degenerative disc disease, spinal stenosis, spondylolisthesis, spinal deformities, fractures, pseudarthrosis, tumors, failed previous fusions, other vertebral segment trauma or diseases. However, the invention is not so limited and various aspects of the present invention may have application for other procedures. The bone fixation system 20 includes a bone fastener 22, an outer receiver or outer tulip 24 coupled to the bone fastener 22, a fastener locking cap 26, an inner receiver or inner tulip 28, and a rod locking cap or set screw 30. The bone fixation system 20 may also include an elongate fixation member or connecting rod 32. It should be noted, however, that although the bone fixation system 20 is generally illustrated and described as a single assembly for use with a single connecting rod 32, any combination of bone fixation systems 20 and connecting rods 32 can be employed during a surgical procedure. For example, in a single level spinal fixation procedure, two bone fixation systems 20 can receive a single connecting rod 32 along one side of the spine and two bone fixation systems 20 can receive another connecting rod 32 along the opposite side of the spine. A multiple level spinal fixation procedure, however, will generally require additional bone fixation systems 20. In addition, the bone fixation systems 20 need not be coupled to adjacent vertebral bodies, but rather, the bone fixation systems 20 can be positioned so as to skip adjacent vertebral bodies if desired. The bone fixation system 20 can be composed of any suitable material, such as titanium, stainless steel, metal, metal alloys, polymers, synthetic polymers such as polyether ether ketone (PEEK), plastics or any other sufficiently rigid and strong material which is biologically compatible and can maintain its strength in vivo for at least six months. The various components of the bone fixation system 20 can be made of materials that are different from the other components of the system 20.

Still referencing FIG. 1, the bone fastener 22 is configured to engage the anatomy to couple the bone fixation system 20 to the anatomy. The bone fastener 22 includes a head 34 at a proximal end and an elongate threaded shank portion 36 extending between the head 34 and a distal end along a longitudinal axis. The bone fastener 22 is configured as a typical bone screw; however, the invention is not so limited and any fastener or other-shaped anchor may be employed such as a laminar hook. The bone fastener 22 may be a self-tapping bone screw having at least one cutting flute. Alternatively, a bone screw that requires a hole to be pre-tapped prior to insertion may be employed. The head 34 can be generally arcuate having a curved or bulbous outer surface and may be spherical or partially spherical in shape. The head 34 can include a driver connection feature 38 at the proximal end for mating with any type of driver such as a hex tool having a hexagonal distal tip to enable the application of torque to drive the bone fastener 22 into the anatomy. Generally, the head 34 has a wider lateral dimension relative to the lateral dimension of the shank portion 36.

Turning now to FIG. 2, the outer receiver or outer tulip 24 will now be described in detail. The outer receiver 24 includes a sidewall 40 having an outer surface and an inner surface. The sidewall 40 forms a proximal opening 42 at the proximal end leading into a substantially cylindrical inner bore that extends to a distal opening 44 at the distal end of the outer receiver 24. The distal opening 44 is configured for receiving at least a part of the shank portion 36 and/or head 34 of the bone fastener 22. The inner surface of the outer receiver 24 at the distal end defines a bone fastener-receiving location 46. The inner surface of the outer receiver 24 in the bone fastener-receiving location 46 is contoured to form a conforming seat for the bone fastener 22 such that when the bone fastener 22 is inserted into the distal opening 44, the bone fastener 22 may freely pivot and angulate polyaxially unimpeded relative to the outer receiver 24 as well as rotate about the longitudinal axis of the fastener 22. The inner surface of the outer receiver 24 in the bone fastener-receiving location 46 includes threads 48 or other interlocking surface configured for engagement with threads or complimentary interlocking surface on the outer surface of the fastener locking cap 26.

The sidewall 40 of the outer receiver 24 forms two upstanding, oppositely disposed arms 50. The arms 50 are spaced apart from each other to define at least one channel 52 in the sidewall 40. In one variation, the channels 52 comprise two oppositely disposed, substantially U-shaped spaces that interconnect with the proximal opening 42 and the inner bore of the outer receiver 24. The channels 52 are shaped to receive an elongate fixation member 32 such as a spinal fixation rod or other elongate member to be connected to the outer receiver 24 by placement of the elongate fixation member 32 into the channels 52. The outer receiver 24 includes a rod-receiving location 54. The rod-receiving location 54 is generally located above the bone fastener receiving location 46. In the rod-receiving location 50 of the outer receiver 24, the inner surface defines at least two oppositely disposed threaded portions or inner interlocking surfaces 56. These threaded portions 56 extend longitudinally vertically in the rod-receiving location 54 and are configured to threadingly engage threads or other complimentary interlocking features formed on the outer surface of the rod locking cap 30. Adjacent to the threaded portions 56 are two oppositely disposed smooth surfaces 58 that also run longitudinally vertically in the rod-receiving location 54. The smooth surfaces 58 provide the inner receiver 28 with a channel or location for unimpeded longitudinal, vertical translation of the inner receiver 28 relative to the outer receiver 24. The smooth surfaces 58 may appear as vertical notches or recessed portions formed into the inner surface of the outer receiver 24. Hence, the inner surface of the outer receiver 24 includes both recessed regions 58 and non-recessed regions 56. The non-recessed regions 56 include threads 60. The recessed regions 58 are recessed with respect to the non-recessed regions 56. The recessed regions 58 are smooth surfaces that extend longitudinally vertically adjacent to the longitudinally extending non-recessed threaded regions 56 in the rod receiving location 54. The recessed regions 58 are configured to receive the arms of the inner receiver 28 such that the inner receiver 28 may translate vertically relative to the outer receiver 24 within the recessed regions 58. With the inner receiver 28 positioned within the recessed regions 58, the inner surface of the arms of the inner receiver 28 are flush with the non-recessed regions 56 of the inner surface of the outer receiver 24 as are their respectively interlocking surfaces/threads to provide a smooth transition between them for unimpeded locking engagement. The outer surface of the outer receiver 24 may include two small holes (not shown) oppositely disposed in the arms 50 for permitting a reduction instrument or other instrument to grasp onto the outer receiver 24.

With reference to FIG. 3, the fastener locking cap 26 will now be described. The fastener locking cap 26 includes an outer surface 62 and an inner surface 64 interconnected by a top surface 66 and a bottom surface 68 to define a substantially cylindrical shape. The fastener locking cap 26 is configured to fit inside the inner bore of the outer receiver 24. The outer surface 62 includes threads or other interlocking surface 70 configured to engage the threads or other interlocking surface 48 formed on the inner surface of the outer receiver 24 in the bone fastener-receiving location 46. The bottom surface 68 of the fastener locking cap 26 may be curved to conformingly accommodate the spherical or curved head 34 of the bone fastener 22. As the fastener locking cap 26 is threaded downwardly into the inner bore of the outer receiver 24, the bottom surface 68 will engage at least part of the bone fastener head 34 and force it against the seat or inner surface of the outer receiver 24 arresting or otherwise locking the bone fastener 22 in a desired angular position relative to the outer receiver 24. The fastener locking cap 26 also includes an inner bore 72 for accessing the driver connection feature 38 formed on the head 34 of the bone fastener 22. Furthermore, the fastener locking cap 26 includes two oppositely disposed, prongs 74 that extend radially outwardly from the outer surface 62. The prongs 74 provide a location to grasp the fastener locking cap 26 with an instrument or by hand to rotate the fastener locking cap 26 from an unlocked position in which the bone fastener 22 is free to angulate with respect to the outer receiver 24 to a locked position in which the bone fastener 22 is fixed in a desired position relative to the outer receiver 24. In the locked position, the fastener locking cap 26 bears down upon the head 34 of the bone fastener 22 forcing it against the outer receiver 24 in the bone fastener receiving location 46. Of course, the prongs 74 may be any instrument engaging surface feature including notches or indents extending inwardly from the outer surface of the fastener locking cap 26.

With reference to FIG. 4, the inner receiver or inner tulip 28 will now be described in detail. The inner receiver 28 includes a circular base 76 that is sized and configured for insertion into the inner bore of the outer receiver 24. The base 76 includes an outer surface 78 and an inner surface 80 interconnected by a top surface 82 and a bottom surface 84. A central aperture 86 is optional and extends through the base 76 for accessing the driver connection feature 38 in the head 34 of the bone fastener 22 with an instrument for driving the bone fastener 22 into anatomy. Two upstanding, oppositely disposed arms 88 extend longitudinally upwardly from the top surface 82. The arms 88 are curved circumferential segments, each having an outer surface 90 and an inner surface 92 with inner threads 94. Two oppositely disposed substantially U-shaped channels 89 are defined between the arms 88 for receiving an elongate fixation member 32. The outer surface 90 is configured for being received within the smooth surfaces or recessed portions 58 of the inner surface of the outer receiver 24 in the rod-receiving location 54. The inner surface 92 with threads 94 or interlocking surface 94 is configured for alignment with threaded or interlocking surface portions 56 of the outer receiver 24 such that when the inner receiver 28 is placed into the recessed portions 58 the threads or interlocking surface 94 on the inner receiver 28 align with the threads or interlocking surface 60 on the outer receiver 24 such that threads or interlocking surface 91 on the outer surface of the rod locking cap 30 engage both sets of threads or interlocking features 60, 94 simultaneously when inserted into the outer receiver 24 and between the arms 88 of the inner receiver 28. Prior to insertion of the rod locking cap 30, the inner receiver 28 is free to translate longitudinally vertically with respect to the outer receiver 24. This vertical translation advantageously permits z-axis positioning of an elongate fixation member 32 placed within the channels 52 with the base 76 of the inner receiver 28 vertically supporting the elongate fixation member 32 and the rod locking cap 30 locking down the elongate fixation member 32 into position along the longitudinal axis within the rod receiving location 54.

With reference back to FIG. 1, the rod locking cap or set screw 30 is a substantially cylindrical object having an outer surface 96 interconnected with a top surface 98 and a bottom surface 99. The outer surface 96 includes threads 91 and is configured to fit inside the inner receiver 28 and threadingly engage with the threads 94 on the inner surface 92 of the arms 88 of the inner receiver 28 as well as engage with threads 60 on the inner surface of the outer receiver 24. The top surface 98 of the set screw 30 includes a driver receiving connection bore 93 or socket configured for engaging the tip of a driving instrument for turning the set screw 30 between a locked position and an unlocked position. The bottom surface 99 of the set screw 30 may include a conforming surface that conforms to the outer contour of an elongate fixation member 32. As the set screw 30 is threadingly translated downwardly into threaded engagement with the inner bore of the outer receiver 24 via threads 60 and into threaded engagement with the inner receiver 28 via threads 94, it will bear down with force onto the elongate fixation member 32 to lock it into the desired position. Threaded engagement of the set screw 30 with both the outer receiver 24 and the inner receiver 28 advantageously locks the z-axis vertical position of the inner receiver 28 relative to the outer receiver 24. It is understood that threads may be substituted for any mechanical interlocking surface feature where suitable and appropriate.

With continued reference to FIG. 1, the elongate fixation member 32 is a typical spinal fixation rod having a solid cylindrical shape having a circular cross-section and a length that spans any number of vertebrae that are desired to be fixed. A short portion of the elongate fixation member 32 is pictured in the figures for exemplary purposes only. Although a spinal fixation rod is pictured, the use of any fixation member having any cross-section is within the scope of the present invention.

With reference to FIG. 1, at least one optional spring 95 is provided between the inner receiver 28 and the fastener locking cap 26. The at least one spring 95 provides a bias force to raise the inner receiver 28 relative to the fastener locking cap 26 so that the z-axis position of the inner receiver 28 and hence, the z-axis position of the elongate fixation member 32 may be more easily adjusted. Spring receiving areas may be provided to help retain the at least one spring 95 in position.

Figure 8A:
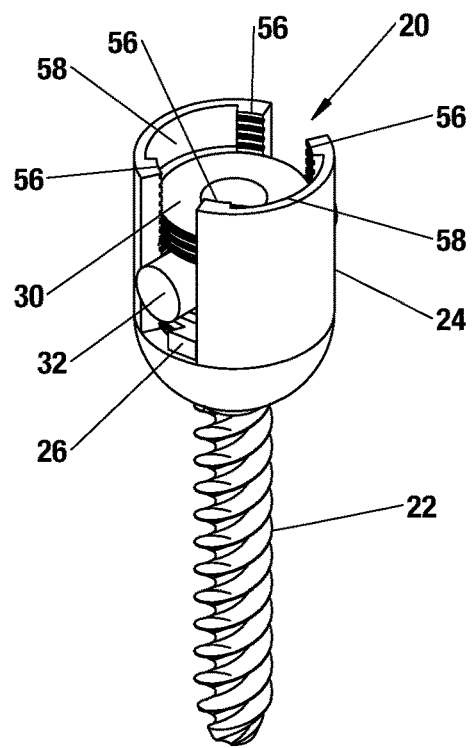
FIG. 8A is a top perspective view of a bone fixation system according to the present invention.
Figure 9A:
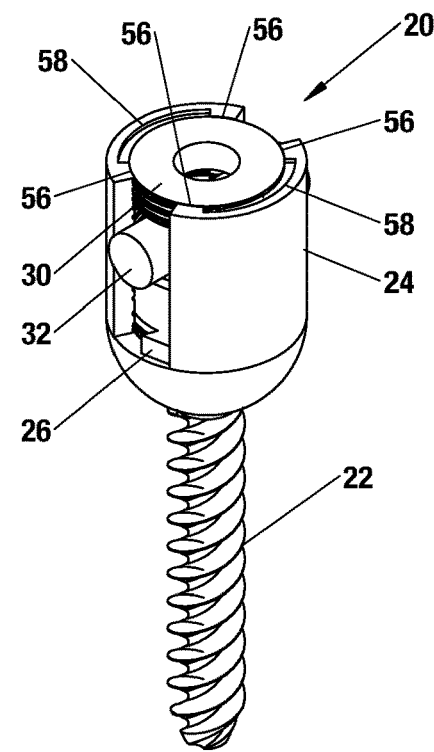
FIG. 9A is a top perspective view of a bone fixation system according to the present invention.
Figure 8B:
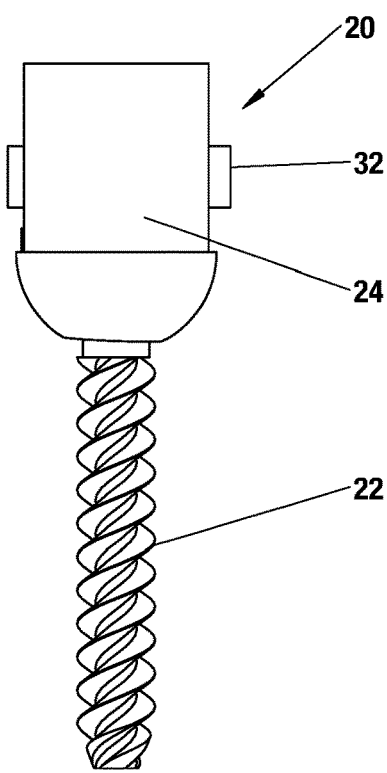
FIG. 8B is a side elevational view of a bone fixation system according to the present invention.
Figure 9B:
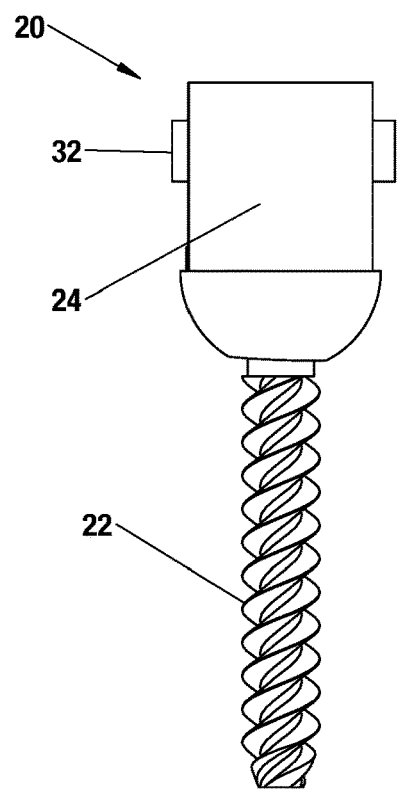
FIG. 9B is a side elevational view of a bone fixation system according to the present invention.

The bone fixation system 20 is assembled by passing the shank portion 36 of the bone fastener 22 through the proximal opening 42 and into the distal opening 44 in the outer receiver 24 with the head 34 coming to rest in the seat of the bone fastener receiving location 46 of the outer receiver 24. An additional retainer (not shown) may be employed if the distal opening 44 is too large to retain the head 34 of the bone fastener 22. The retainer forms an additional seating location for the bone fastener 22 permitting it to be retained inside the outer receiver 24. The fastener locking cap 26 is inserted into inner bore of the outer receiver 24 and into the bone fastener receiving location 46 where the threads 70 of the bone fastener locking cap 26 are engaged with threads 48 in the bone fastener receiving location 46 in a manner that permits angulation of the fastener 22 or not as desired. At least one optional spring 95 is disposed in spring-receiving areas and the inner receiver 28 is inserted into the inner bore of the outer receiver 24 such that the arms 88 of the inner receiver 28 slide within the recessed portions 58. An elongate fixation member 32 is located between the arms 88 within the inner receiver 28. The elongate fixation member 32 is permitted to translate along the longitudinal z-axis together with the inner receiver 28 being biased by the at least one spring 95 when in an unlocked position. When the desired position along the z-axis is ascertained, the rod locking cap 30 is inserted into the outer receiver 24 and between the arms 88 of the inner receiver 28 and the threads 91 on the rod locking cap 30 are threadingly engaged with the threads 94 on the inner receiver 28 simultaneously with the threads 60 on the outer receiver 24 to lock the longitudinal translation of the inner receiver 28 relative to the outer receiver 24. Initial threaded engagement of the rod-locking cap 30 may be with the inner receiver 28 or outer receiver 24 before simultaneously threading with both. Continued downward threaded engagement of the rod locking cap 30 results in the rod locking cap 30 bearing down upon the elongate fixation member 32 locking it into position. At any time, the fastener locking cap 26 may be turned by grasping the prongs 74 such that the fastener locking cap 26 translates downwardly and bears down with force onto the head 34 of the bone fastener 22 locking its angulation relative to the outer receiver 24. Prior to insertion of an elongate fixation member 32, a driver is inserted into the inner bore of the outer receiver 24, through the central aperture 86 of the inner receiver 28, through the bore 72 of the fastener locking cap 26 to engage the driver connection feature 38 in the head 34 of the bone fastener 22. The driver is then turned to drive the bone fastener 22 into the bone anatomy. With the shank portion 36 resident in the anatomy, the outer receiver 24 is permitted to angulate relative to the bone fastener 22 until the fastener locking cap 26 is turned to a locked position in which it bears downwardly onto the head 34 of the fastener 22 thereby arresting the angulation of the outer receiver 24 relative to the bone fastener 22. The fastener locking cap 26 may be rotated in an opposite direction to unlock the outer receiver 24 relative to the bone fastener 22 so that the angulation of the outer receiver 24 may be adjusted and relocked as desired. This may be repeated as needed FIGS. 5A, 5B, 6A, 6B, 7A, 7B, 9A, 9B show the elongate fixation member 32 locked into a relatively high position along the z-axis or longitudinal axis within the outer receiver 24. In comparison, FIGS. 8A, 8B, illustrate the bone fixation system 20 with the elongate fixation member 32 locked into a relatively low position along the z-axis within the outer receiver 24. The relative z-axis translation range is advantageously approximately 10 mm on a standard sized outer tulip 24. Of course, the range may be greater if a larger outer tulip 24 with a longer inner bore is provided or, alternatively, in another variation of the invention, multiple inner receivers are configured to telescope relative to each other to achieve a larger range of translation along the z-axis. The multiple inner receivers are nested within each other to create the telescoping effect. The arms 50 with the smooth surfaces 54 permit the inner receiver 24 and attached fastener locking cap 26 to telescope freely vertically within the bore of the outer receiver 24. A driver instrument may then be inserted into the proximal opening 40 of the bore of the outer receiver 24 and through the central aperture 80 of the inner receiver 28 and through the bore 66 of the fastener locking cap 26 and into the driver connection feature in the bone fastener head 34. The user may then rotate the driver to drive the bone fastener 22 into the anatomy. With the shank portion 36 delivered into bone, the outer receiver 24 is permitted to angulate with respect to the bone fastener 22. An elongate fixation member 32 is then placed into the channel 48 and between the arms 88 of the inner receiver 28. Since the inner receiver 28 is advantageously free to translate longitudinally within the bore of the outer receiver 24, in particular, free to translate longitudinally within the rod-receiving location of the outer receiver 24, substantial z-axis translation is afforded for precisely locating the elongate fixation member 32 in the desired location custom to the anatomy. A set screw 30 is placed into the inner receiver 28 such that its threads 96 engage the threads 94 of the inner surface 92 of the arms 88. A driver instrument is employed to turn the set screw 30 translating it longitudinally downwardly onto the elongate fixation member 32. Throughout this time, the elongate fixation member 32 and angle of the outer receiver 24 may be precisely determined and the set screw 30 incrementally advanced downward to zero in on the precise orientation of these components.

Figure 10:
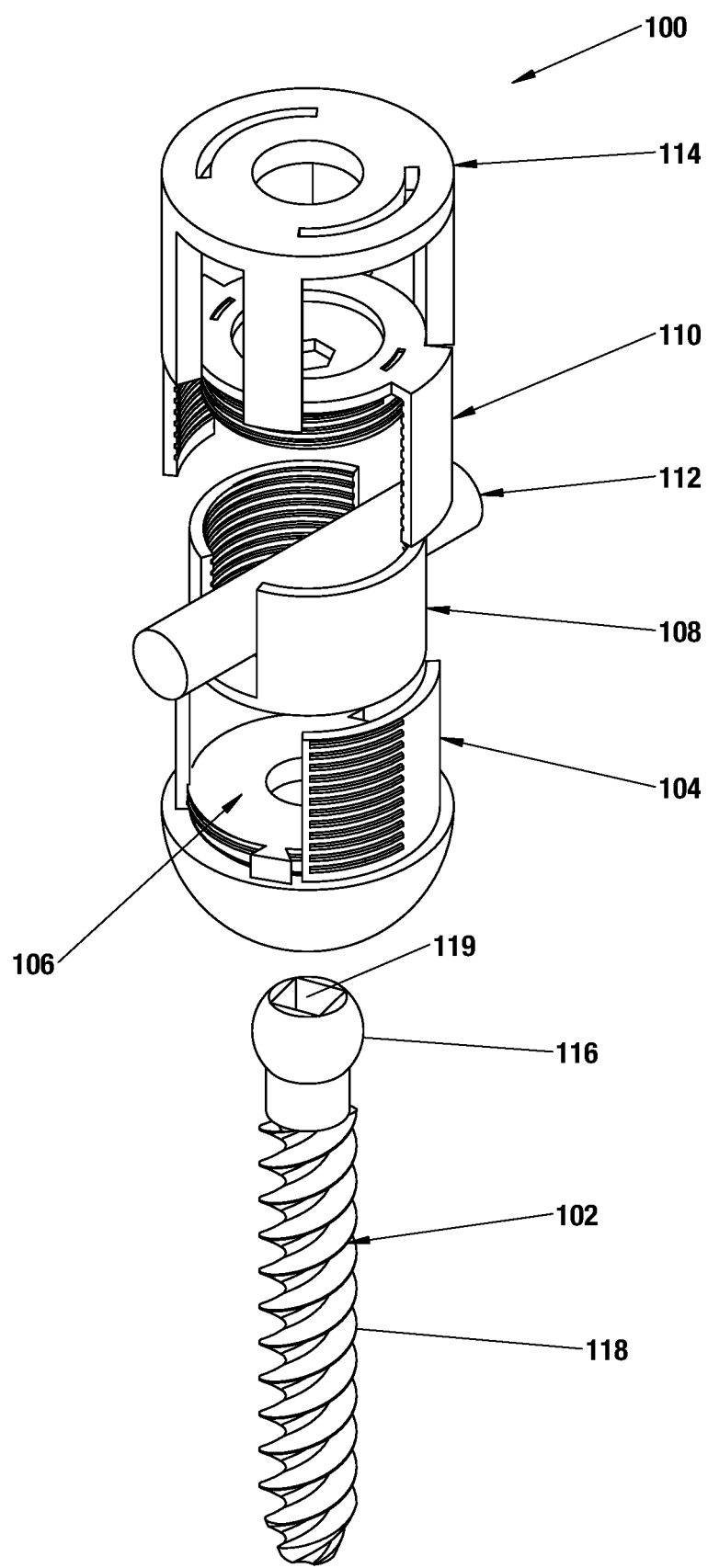
FIG. 10 is a top perspective, exploded view of a bone fixation system according to the present invention.

Turning now to FIG. 10, there is shown another bone fixation system 100 according to the present invention. The bone fixation system 100 includes a bone fastener 102, an outer receiver or outer tulip 104, a fastener locking cap 106, an inner receiver or inner tulip 108, a rod locking cap or set screw 110, an elongate fixation member 112 and an optional cover 114.

The bone fastener 102 is configured to engage the anatomy to couple the bone fixation system 100 to the anatomy. The bone fastener 102 includes a head 116 at a proximal end and an elongate threaded shank portion 118 extending between the head 116 and a distal end along a longitudinal axis. The bone fastener 102 is configured as a typical bone screw; however, the invention is not so limited and any fastener or other-shaped anchor may be employed. The bone fastener 102 may be a self-tapping bone screw having at least one cutting flute. Alternatively, a bone screw that requires a hole to be pre-tapped prior to insertion may be employed. The head 116 can be generally arcuate having a curved or bulbous outer surface and may be spherical or partially spherical in shape. The head 116 can include a driver connection feature 119 at the proximal end for mating with any type of driver such as a hex tool having a hexagonal distal tip to enable the application of torque to drive the bone fastener 102 into the anatomy.

Figure 11A:
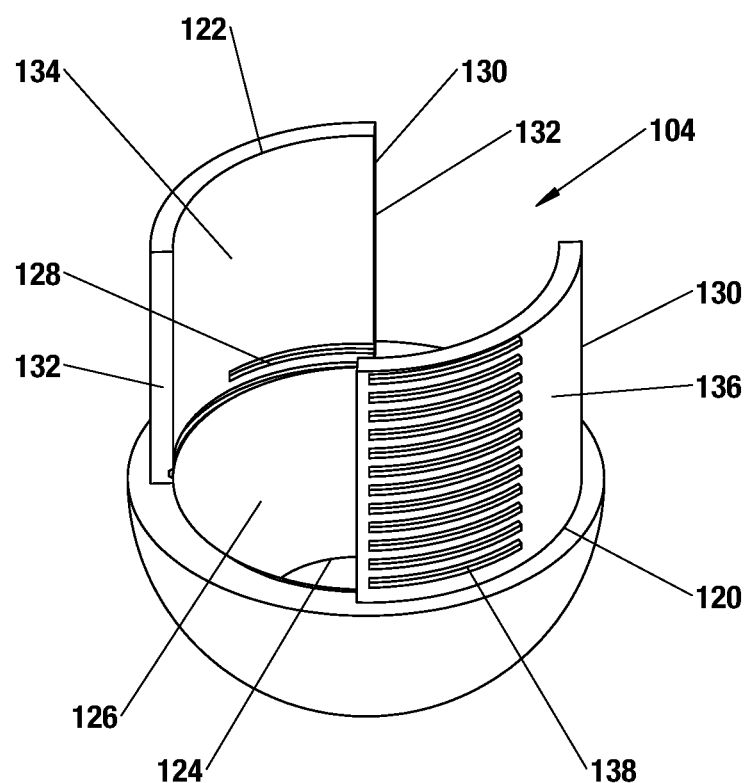
FIG. 11A is a top perspective view of an outer receiver according to the present invention.

Turning now to FIG. 11A, the outer receiver or outer tulip 104 will now be described in detail. The outer receiver 104 includes a sidewall 120 having an outer surface and an inner surface. The sidewall 120 forms a proximal opening 122 at the proximal end leading into a substantially cylindrical inner bore that extends to a distal opening 124 at the distal end of the outer receiver 104. The distal opening 124 is configured for receiving at least a part of the shank portion 118 and/or head 116 of the bone fastener 102. The inner surface of the outer receiver 104 at the distal end defines a bone fastener-receiving location 126. The inner surface of the outer receiver 104 in the bone fastener-receiving location 126 is contoured to form a conforming seat for the bone fastener 102 such that when the bone fastener 102 is inserted into the distal opening 124, the bone fastener 102 may freely pivot and angulate polyaxially unimpeded relative to the outer receiver 104 as well as rotate about the longitudinal axis of the shank portion 118. The inner surface of the outer receiver 104 in the bone fastener-receiving location 126 includes threads or other interlocking surface feature 128 configured for engagement with threads or interlocking surface feature on the outer surface of the fastener locking cap 106.

The sidewall 120 of the outer receiver 104 forms two upstanding, oppositely disposed arms 130. The arms 130 are spaced apart from each other to define two oppositely disposed channels 132 formed in the sidewall 120. The channels 132 comprise two oppositely disposed, substantially U-shaped spaces that interconnect with the proximal opening 122 and the inner bore of the outer receiver 104. The channels 132 are shaped to receive an elongate fixation member 112 such as a spinal fixation rod or other elgonate member to be connected to the outer receiver 104 by placement of the elongate fixation member 112 into the channels 132. The outer receiver 104 includes a rod-receiving location 134. The rod-receiving location 134 of the outer receiver 104 is substantially in the location of the two arms 130 and the inner surface of the arms 132 define two oppositely disposed smooth surfaces such that the inner receiver 108 which fits within the arms 130 of the outer receiver 104 may unimpededly translate longitudinally along the z-axis. The arms 130 extend upwardly from the bone fastener receiving location 126 such that the outer surface of the arms 130 is set back from the outer surface of the bone fastener receiving location 126 to create a circumferential ledge surrounding the arms 130. The outer surface of each of the arms 130 includes a smooth surface 136 extending longitudinally that is adjacent to a threaded or interlocking outer surface 138 extending longitudinal along the outer surface of each arm 130. The threaded surface 138 on the outer surface of one arm 130 is oppositely disposed from a threaded surface 138 on the outer surface of the second arm 130. Also, the smooth surface 136 on the outer surface of one arm 130 is oppositely disposed from the smooth surface 136 located on the outer surface of the second arm 130. The outer surface of the outer receiver 104 may include two small holes (not shown) oppositely disposed in the arms 130 for permitting a reduction instrument or other instrument to grasp onto the outer receiver 104.

Figure 11B:
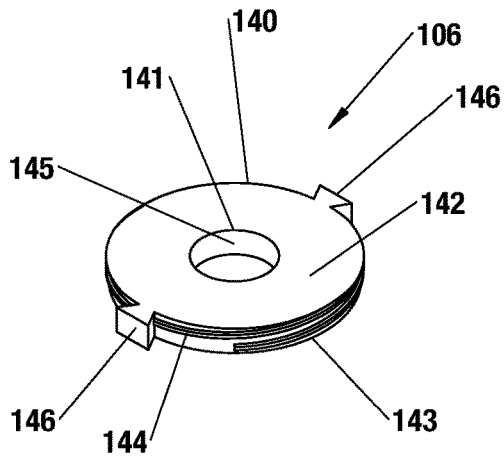
FIG. 11B is a top perspective view of a fastener lock according to the present invention.

Turning now to FIG. 11B, the fastener locking cap 106 will now be described. The fastener locking cap 106 includes an outer surface 140 and an inner surface 141 interconnected by a top surface 142 and a bottom surface 143 to define a substantially cylindrical shape. The fastener locking cap 106 is configured to fit inside the inner bore of the outer receiver 104. The outer surface 140 includes threads/interlocking features 144 configured to engage the threads or other interlocking surface features 128 formed on the inner surface of the outer receiver 104 in the bone fastener-receiving location 126. The bottom surface 143 of the fastener locking cap 106 may be curved to conformingly accommodate the spherical or curved head 116 of the bone fastener 102. As the fastener locking cap 106 is threaded downwardly into the inner bore of the outer receiver 104, the bottom surface 143 will engage at least part of the bone fastener head 116 and force it against the seat or inner surface of the outer receiver 104 arresting or otherwise locking the bone fastener 102 in a desired angular position relative to the outer receiver 104. The fastener locking cap 106 also includes an inner bore 145 for accessing the driver connection feature 119 formed on the head 116 of the bone fastener 102. The inner bore 145 may not only serve as a through-hole for accessing the driver connection feature 119 on the bone fastener 102 for driving the bone fastener 102 into bone, but also, the inner bore 145 may be shaped for accepting a tool for driving the fastener locking cap 106 itself. As such, the inner bore 145 may be hexagonal in shape for receiving a hexagonal-shaped tip of a driver instrument. The driver instrument is configured to rotate the fastener locking cap 106 from an unlocked position in which the bone fastener 102 is free to angulate with respect to the outer receiver 104 to a locked position in which the bone fastener 102 is fixed in a desired position relative to the outer receiver 104. In the locked position, the fastener locking cap 106 bears down upon the head 116 of the bone fastener 102 forcing it against the outer receiver 104 in the bone fastener receiving location 126.

Figure 12:
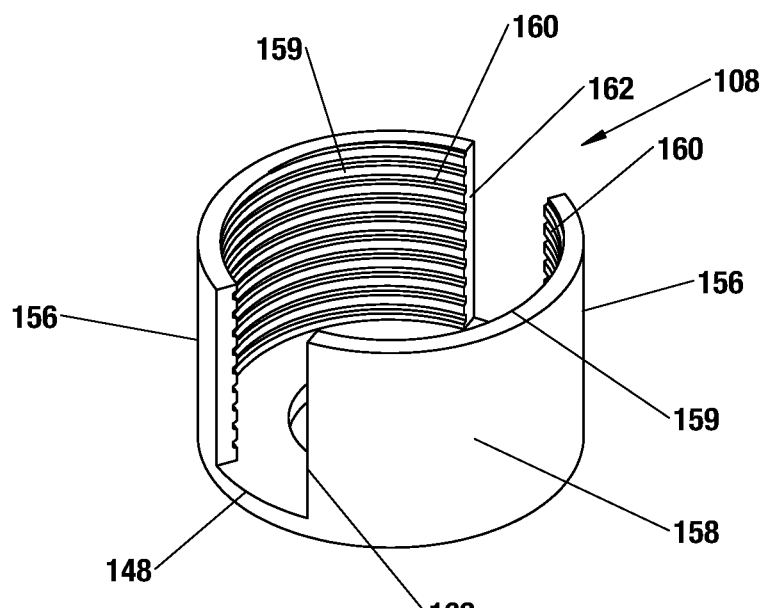
FIG. 12 is a top perspective view of an inner receiver according to the present invention.

With reference to FIG. 12, the inner receiver or inner tulip 108 will now be described in detail. The inner receiver 108 includes a circular base 148 that is sized and configured for insertion into the inner bore of the outer receiver 104. In particular, the inner receiver 108 is sized and configured for being received between the arms 130 of the outer receiver 104. The base 148 includes an outer surface and an inner surface interconnected by a top surface and a bottom surface. A central aperture extends through the base 148 for accessing the driver connection feature 119 in the head 116 of the bone fastener 102 with an instrument for driving the bone fastener 102 into anatomy. Two upstanding, oppositely disposed arms 156 extend longitudinally upwardly from the top surface 152. The arms 156 are curved circumferential segments, each having an outer surface 158 and an inner surface 159 with inner threads 160. At least one channel 162 is defined between the arms 156 for receiving an elongate fixation member 112. The outer surface 158 of the each arm 156 is configured for being received within the smooth inner surface of the outer receiver 104 in the rod-receiving location 134. The inner surface 159 with threads 160 is configured for threaded engagement with threads of the rod-locking cap or set screw 110. The base 148 serves as a support or floor for the elongate fixation member 112 placed within the channels 162 of the inner receiver 108. With the inner receiver 108 disposed between the arms 130 of the outer receiver 104, the inner receiver 108 is free to translate longitudinally relative to the outer receiver 104.

Figure 13:
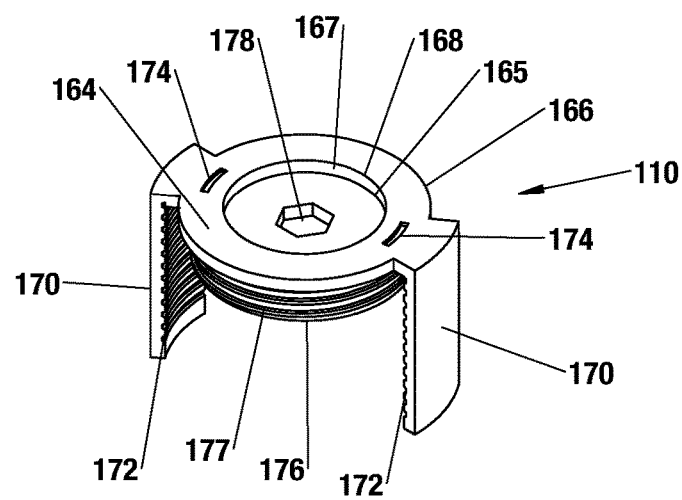
FIG. 13 is a top perspective view of a set screw according to the present invention.

Turning now to FIG. 13, the rod-locking cap or set screw 110 will now be described. The set screw 110 includes a top surface 164 and a bottom surface 165 interconnected by an outer surface 166 and an inner surface 167. The inner surface 167 defines a central aperture 168. Two oppositely disposed legs 170 extend outwardly from the outer surface 166 and downwardly. The inner surface of the legs 170 includes threads 172 or interlocking features that are configured for engaging with the threads 138 or other interlocking features of the outer surface of the arms 130 of the outer receiver 104. The set screw 110 further includes slots 174 configured to engage a tool for rotating the legs 170 from an unlocked position to a locked position relative to the outer receiver 104. The set screw 110 further includes a cylinder 176 coupled to the bottom surface 153. The cylinder 176 includes threads 177 or other interlocking features on its outer surface and is configured to rotate independently of the remainder of the set screw 110 such as the legs 179 and surfaces 164, 165, 166, 167. The top surface of the cylinder 176 includes a tool receiving feature 178 such as a hexagonal socket for receiving a hexagonally shaped driving tool for rotating the cylinder 176.

Figure 14:
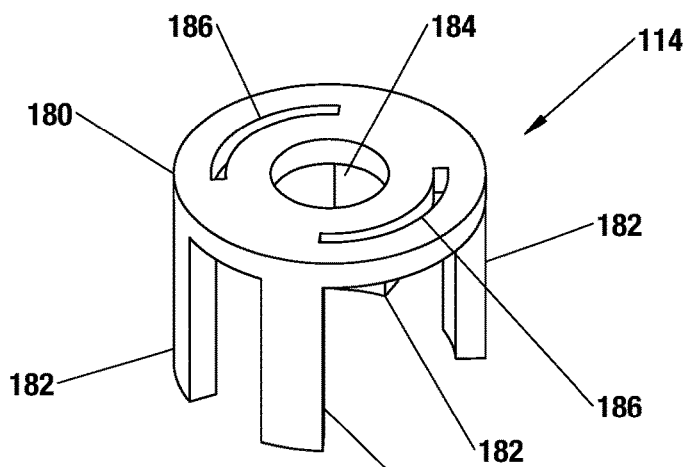
FIG. 14 is a top perspective view of a cover according to the present invention.

Turning now to FIG. 14, the cover 114 will now be described. The cover 114 includes a circular top 180 with a plurality of downwardly extending legs 182. The top 180 includes a central aperture 184 and two oppositely disposed slots 186. The central aperture 184 provides access to the driver connection feature 119 on the bone fastener 102 or the tool receiving feature 178 for rotating the threaded cylinder 176. The oppositely disposed slots 186 provide access to the slots 174 on the set screw 110 for rotating the set screw 110 to lock the inner receiver 108 to the outer receiver 104.

Figure 15A:
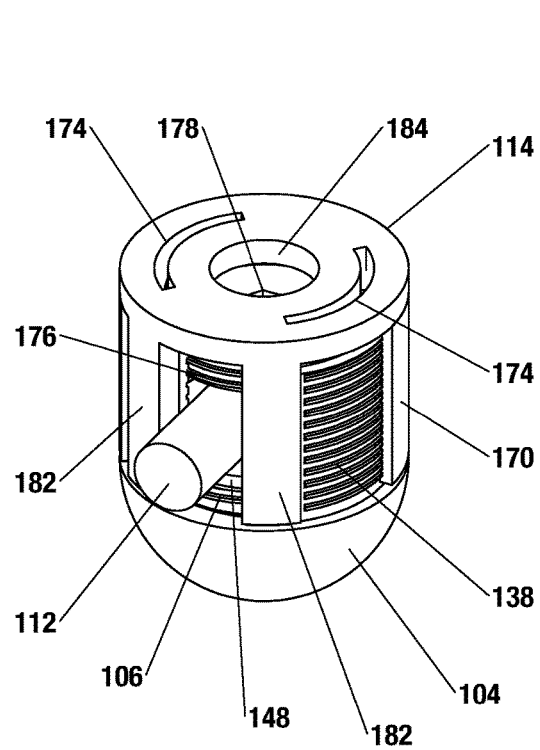
FIG. 15A is a top perspective view of a bone fixation system without a bone fastener according to the present invention.
Figure 16A:
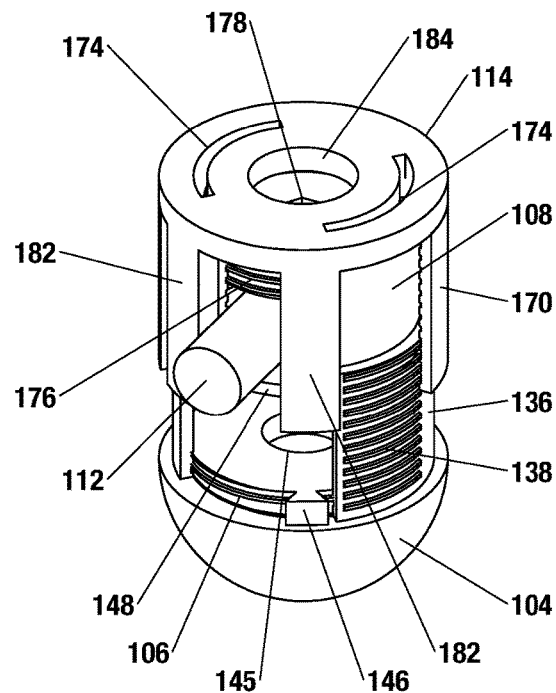
FIG. 16A is a top perspective view of a bone fixation system without a bone fastener according to the present invention.
Figure 15B:
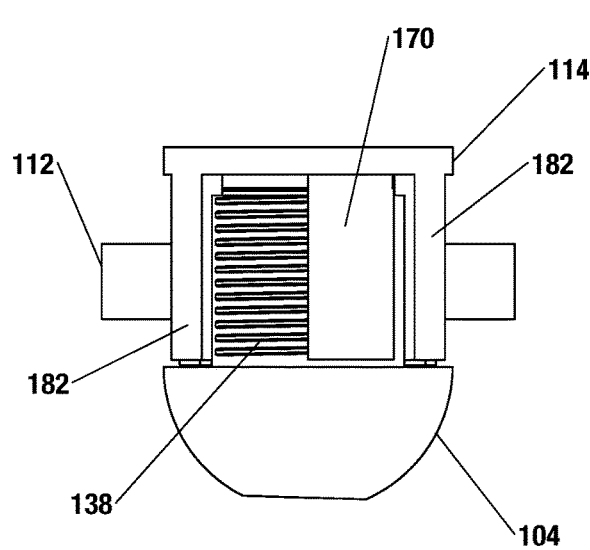
FIG. 15B is a side elevational view of a bone fixation system without a bone fastener according to the present invention.
Figure 16B:
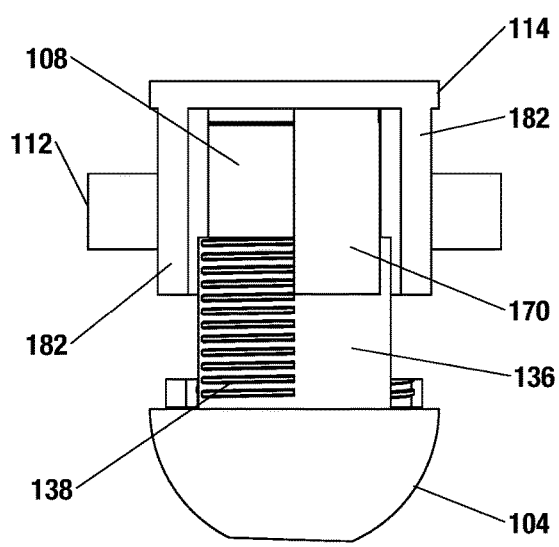
FIG. 16B is a side elevational view of a bone fixation system without a bone fastener according to the present invention.
Figure 17A:
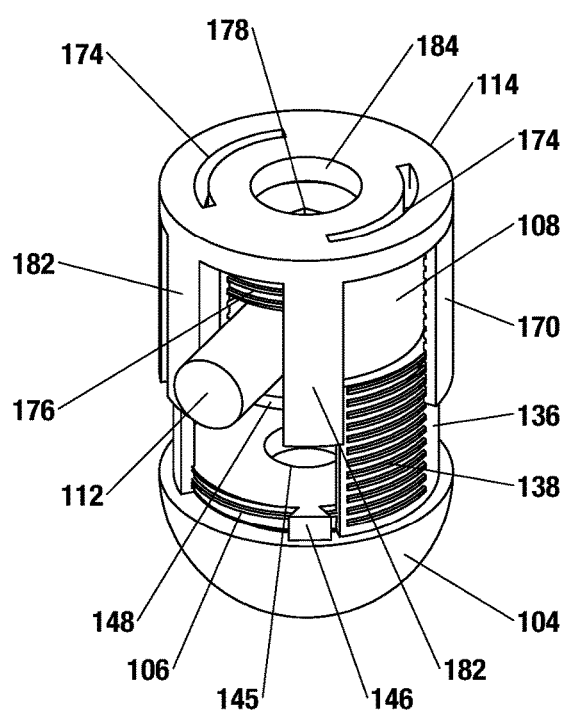
FIG. 17A is a top perspective view of a bone fixation system without a bone fastener according to the present invention.
Figure 18A:
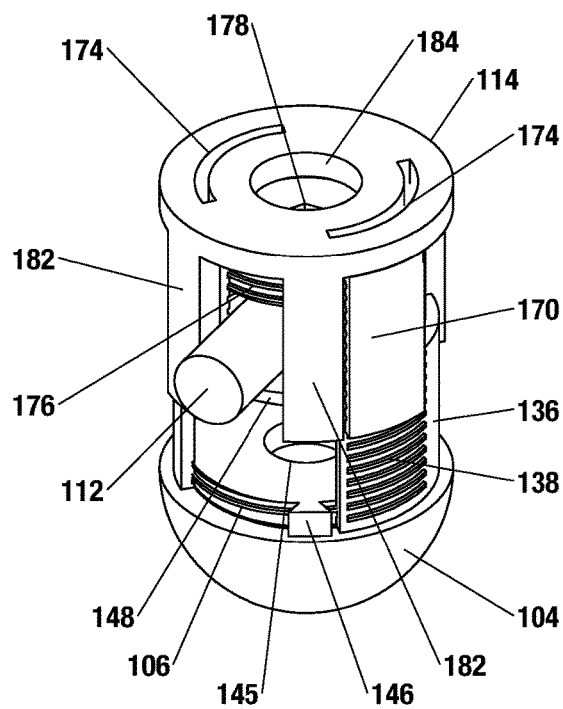
FIG. 18A is a top perspective view of a bone fixation system without a bone fastener according to the present invention.
Figure 17B:
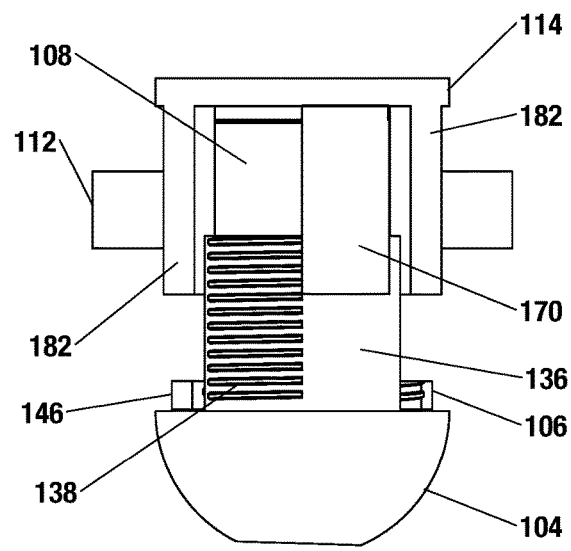
FIG. 17B is a side elevational view of a bone fixation system without a bone fastener according to the present invention.
Figure 18B:
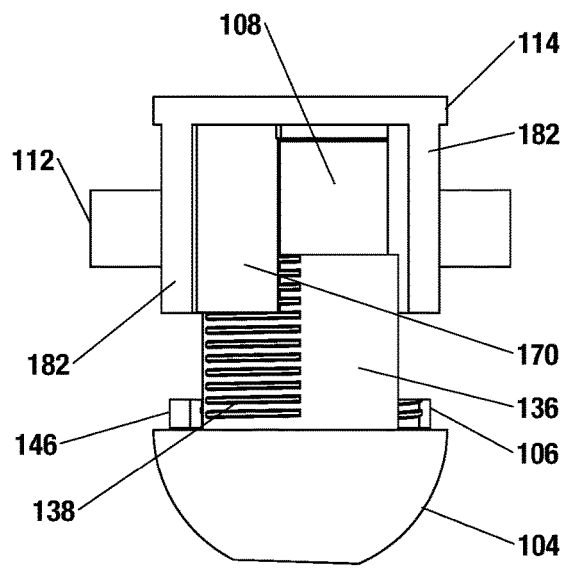
FIG. 18B is a side elevational view of a bone fixation system without a bone fastener according to the present invention.

The bone fixation system 100 is assembled by inserted the bone fastener 102 into the distal opening 124 of the outer receiver 104. A fastener locking cap 106 is inserted into the inner bore of the outer receiver 104 an into the bone fastener receiving location 126 where the threads 144 on the fastener locking cap 106 are engaged with threads 128 in the bone fastener receiving location. The bone fastener 102 is free to angulate polyaxially relative to the outer receiver 104 in an unlocked position. In a locked position, the fastener locking cap 106 is threaded or turned downwardly to bear upon the head 116 of the bone fastener 102 to lock it into a desired angular relationship. The inner receiver 108 is inserted into the inner bore of the outer receiver 108 such that the arms 156 of the inner receiver 108 are substantially aligned inside the arms 130 of the outer receiver 104. The channels 132 of the outer receiver 104 are also substantially aligned with the channels 162 of the inner receiver 108. The outer surface of the inner receiver 108 is substantially flush with the inner surface of the outer receiver 104 and the inner receiver 108 is free to translate longitudinally along the z-axis inside the outer receiver 104. Prior to the placement of an elongate fixation member 112 into the channels 132, 162, the angular relationship of the outer receiver 104 relative to the bone fastener 102 is fixed or otherwise locked into position by employing a driving tool inserted through the central aperture 154 of the inner receiver 108 to engage the inner bore 145 of the fastener locking cap 106 and rotate it into a locked position. When an elongate fixation member 112 is placed into the channels 132, 162, the elongate fixation member 112 rests on the top surface 152 of the inner receiver 108 and the z-axis or longitudinal position of the elongate fixation member may be adjusted moving both the elongate fixation member and inner receiver into the desired position. The set screw 110 is positioned such that the threaded cylinder 176 is inserted into the inner receiver 108 between the arms 156 of the inner receiver 108. The legs 170 of the set screw 110 slide on the outside of the arms 130 of the outer receiver 104 such that the inner surface of the legs 170 is substantially flush with the outer surface of the arms 130 of the outer receiver 104. With the legs 170 in the location of smooth surfaces 136 of the arms 130, the inner receiver 108 is free to translate relative to the outer receiver 104. FIGS. 15A and 15B illustrate the elongate fixation member 112 in a relatively low position along the z-axis, that is, the elongate fixation member 112 is in a position proximal to the bone fastener 112 or distal end of the outer receiver 104. In FIGS. 16A and 16B, the elongate fixation member 112 is shown in a relatively high position along the longitudinal, z-axis. The threaded cylinder 176 may be threaded to the inner receiver 108 to connect the set screw 110 to the inner receiver 108. The threaded cylinder 176 may be rotated with a tool engaged with the tool receiving feature 178 from an unlocked position in which the elongate fixation member 112 is free to move within the channels 162 to a locked position in which the threaded cylinder 176 is rotatingly threaded downwardly to bear against the elongate fixation member 112 locking it into position. In the locked position, the inner receiver 108, the elongate fixation member 112 and the set screw 110 together form substantially a unitary body that is capable of longitudinal translation relative to the outer receiver 104. In essence, there is a first locked position that locks the angulation of the bone fastener 102 relative to the outer receiver 104, a second locked position in which the set screw 110 locks down to fix the elongate fixation member 112 relative to the inner receiver 108 and a third locked position in which the longitudinal z-axis translation of the inner receiver 108 is locked with respect to the outer receiver 104. This third locked position is accomplished by inserting a driving tool into slots 174 on the set screw 110. The tool is then used to rotate the set screw 110 such that the legs 170 of the set screw 110 rotate along the outer surface of the arms 130 of the outer receiver 104 from being adjacent to the smooth surfaces 136 representing an unlocked position as shown in FIGS. 17A and 17B to a locked position in which the threads 172 on the inner surface of the legs 170 engage the threads 138 on the outer surfaces of the arms 130 as shown in FIGS. 18A and 18B.

Figure 19:
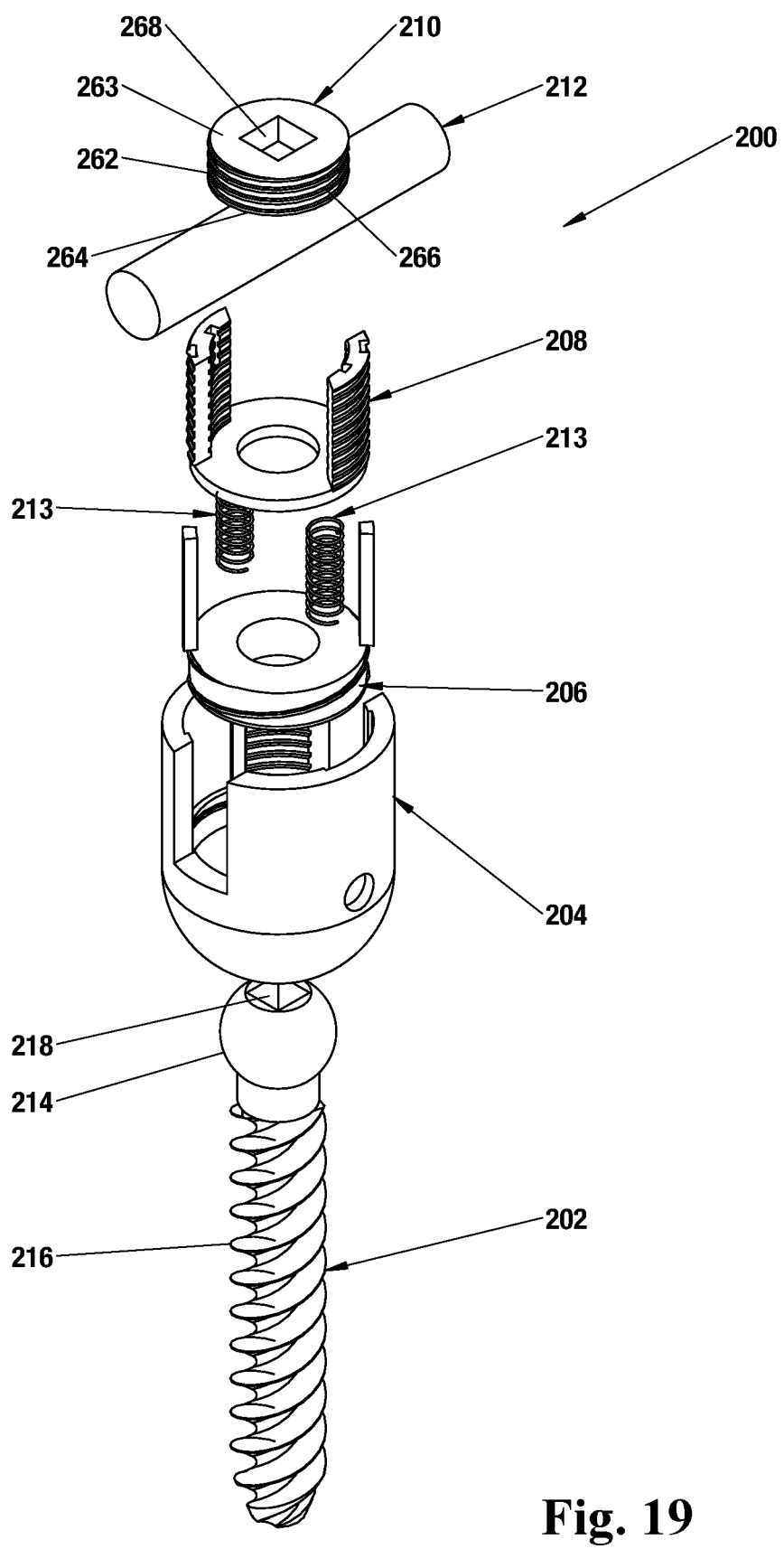
FIG. 19 is a top perspective, exploded view of a bone fixation system according to the present invention.

Turning now to FIG. 19, another variation of the bone fixation system 200 will now be described. The bone fixation system 200 of the present invention includes a bone fastener 202, an outer receiver or outer tulip 204 coupled to the bone fastener 202, a fastener locking cap 206 interconnected with an inner receiver or inner tulip 208, and a rod locking cap or set screw 210. The bone fixation system 200 may also include an elongate fixation member or connecting rod 212 and at least one spring 213 disposed between the fastener locking cap 206 and inner receiver 208. It should be noted, however, that although the bone fixation system 200 is generally illustrated and described as a single assembly for use with a single connecting rod 212, any combination of bone fixation systems 200 and connecting rods 212 can be employed during a surgical procedure. For example, in a single level spinal fixation procedure, two bone fixation systems 200 can receive a single connecting rod 212 along one side of the spine and two bone fixation systems 200 can receive another connecting rod 212 along the opposite side of the spine. A multiple level spinal fixation procedure, however, will generally require additional bone fixation systems 200. In addition, the bone fixation systems 200 need not be coupled to adjacent vertebral bodies, but rather, the bone fixation systems 200 can be positioned so as to skip adjacent vertebral bodies if desired. The bone fixation system 200 can be composed of any suitable material, such as titanium, stainless steel, metal, metal alloys, polymers, synthetic polymers such as polyether ether ketone (PEEK), plastics or any other sufficiently rigid and strong material which is biologically compatible and can maintain its strength in vivo for at least six months. The various components of the bone fixation system 200 can be made of materials that are different from the other components of the system 200.

Still referencing FIG. 19, the bone fastener 202 is configured to engage the anatomy to couple the bone fixation system 200 to the anatomy. The bone fastener 202 includes a head 214 at a proximal end and an elongate threaded shank portion 216 extending between the head 214 and a distal end along a longitudinal axis. The bone fastener 202 is configured as a typical bone screw; however, the invention is not so limited and any fastener or other-shaped anchor may be employed. The bone fastener 202 may be a self-tapping bone screw having at least one cutting flute. Alternatively, the bone screw may require a hole to be pre-tapped prior to insertion. The head 214 can be generally arcuate having a curved or bulbous outer surface and may be spherical or partially spherical in shape. The head 214 can include a driver connection feature 218 or socket at the proximal end for mating with any type of driver such as a driver with a hexagonal-shaped tip to enable the application of torque to drive the bone fastener 202 into the anatomy.

Figure 20:
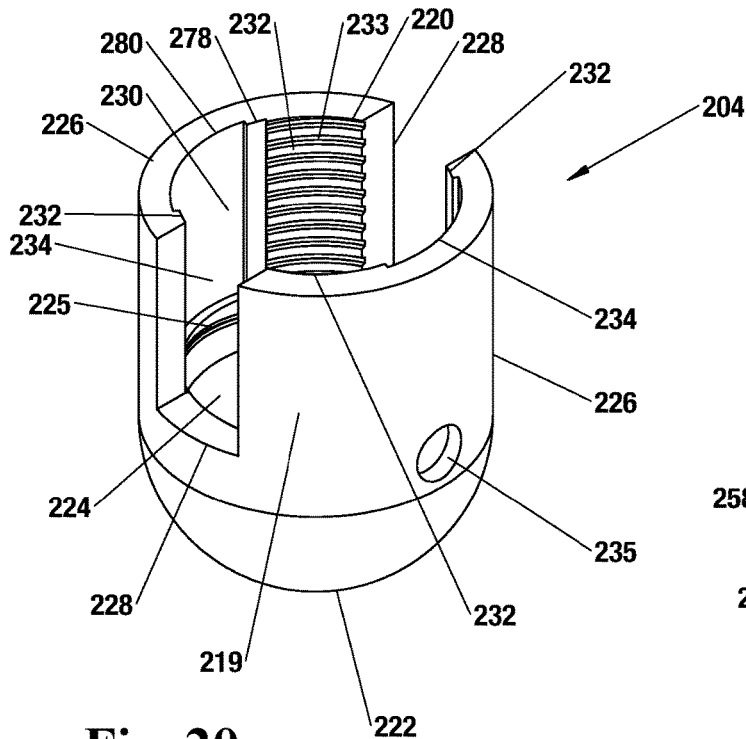
FIG. 20 is a top perspective view of an outer receiver according to the present invention.

Turning now to FIG. 20, the outer receiver or outer tulip 204 will now be described in detail. The outer receiver 204 includes a sidewall 219 having an outer surface and an inner surface. The sidewall 219 forms a proximal opening 220 at the proximal end leading into a substantially cylindrical bore that extends to a distal opening 222 at the distal end of the outer receiver 204. The distal opening 222 is configured for receiving at least a part of the shank portion 216 and/or bone fastener head 214 of the bone fastener 202. The inner surface of the outer receiver 204 at the distal end defines a bone fastener-receiving location 224. The inner surface of the outer receiver 204 in the bone fastener-receiving location 224 is contoured to form a conforming seat for the bone fastener head 214 such that when the bone fastener 202 is inserted into the distal opening 222, the bone fastener 202 may freely pivot and angulate polyaxially unimpeded relative to the outer receiver 204 as well as rotate about the longitudinal axis of the shank portion 216. The inner surface of the outer receiver 204 in the bone fastener-receiving location 224 includes threads or other interlocking surface feature 225 configured for engagement with threads or other interlocking surface feature on the outer surface of the fastener locking cap 206.

Figure 21:
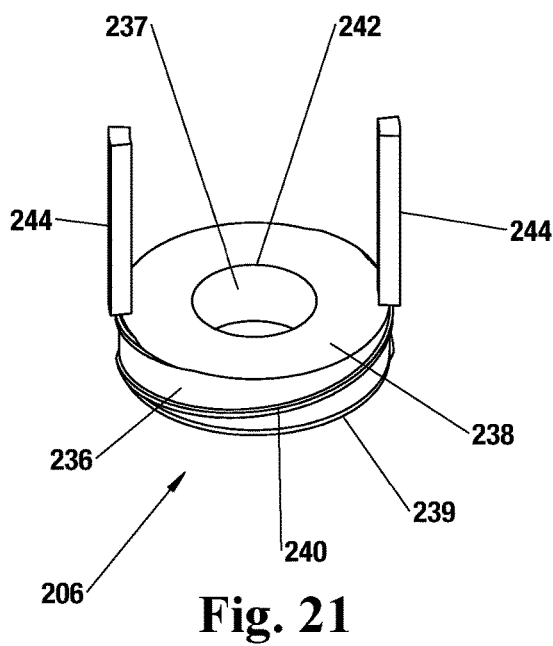
FIG. 21 is a top perspective view of a fastener locking cap according to the present invention.
Figure 33A:
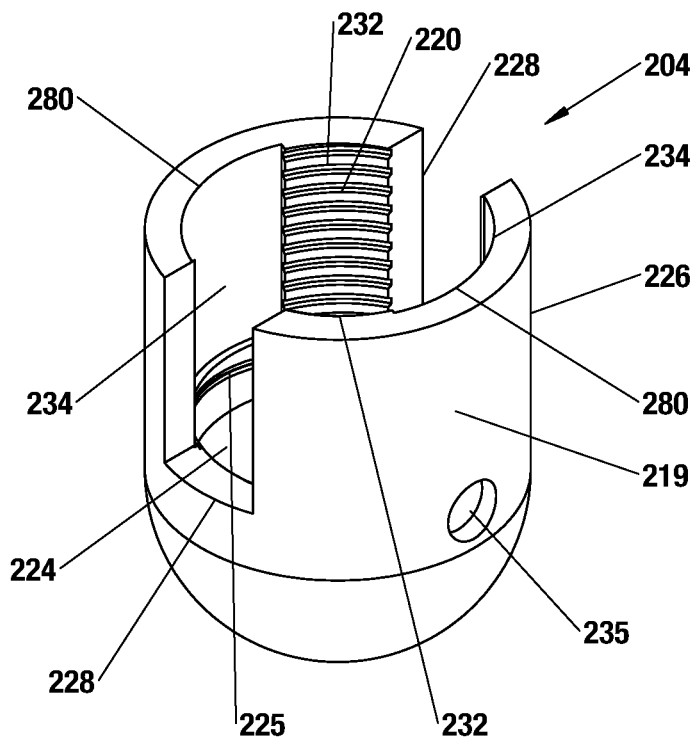
FIG. 33A is a top perspective view of an outer receiver according to the present invention.
Figure 33B:
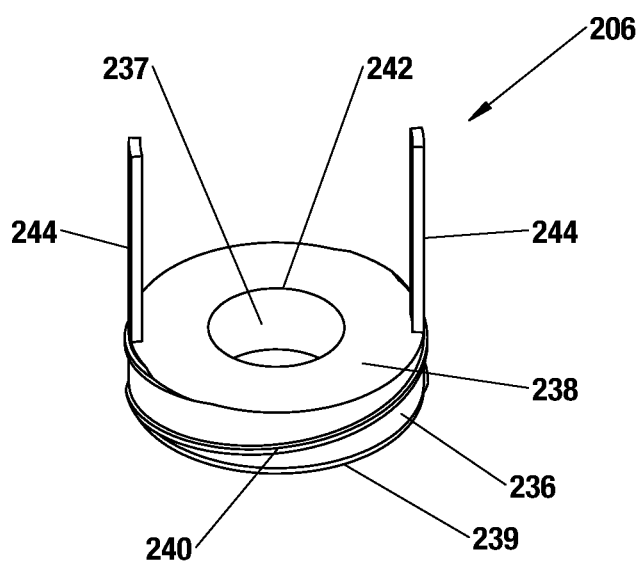
FIG. 33B is a top perspective view of a fastener locking cap according to the present invention.
Figure 34:
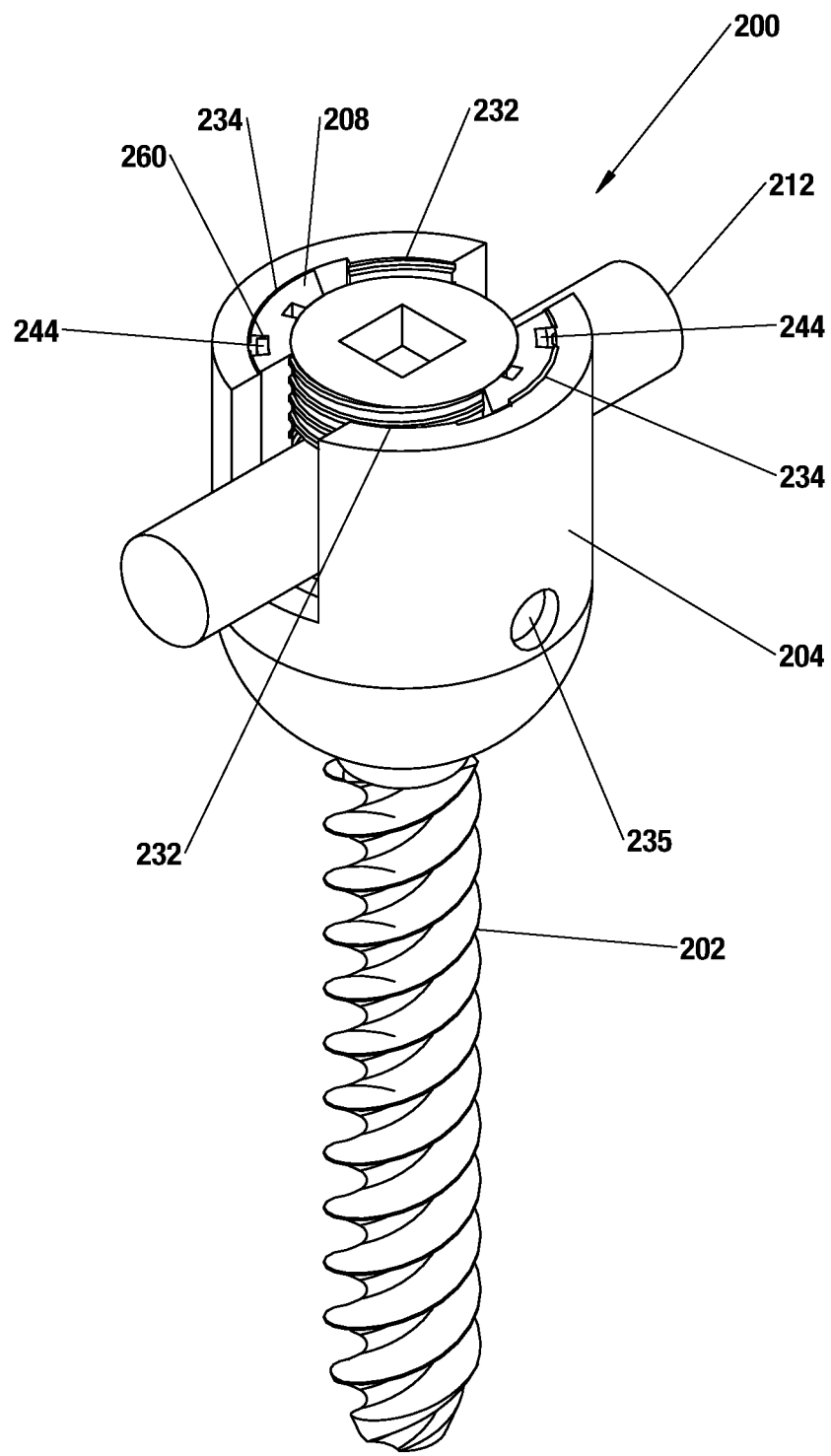
FIG. 34 is a top perspective view of a bone fixation system according to the present invention.

Still referencing FIG. 20, the sidewall 219 of the outer receiver 204 forms two upstanding, oppositely disposed arms 226. The two arms 226 are spaced apart from each other to define at least one channel 228 formed in the sidewall 219. The channels 228 comprise two oppositely disposed, substantially U-shaped spaces that interconnect with the proximal opening 220 and the inner bore of the outer receiver 204. Each channel 228 is shaped to receive an elongate fixation member 212 such as a spinal fixation rod or other elgonate member to be connected to the outer receiver 204 by placement of the rod 212 into the channels 228. The outer receiver 204 includes a rod-receiving location 230 along at least part of the longitudinal length of the outer receiver 204. In the rod-receiving location 230 of the outer receiver 204, the inner surface defines at least two oppositely disposed threaded portions 232 having threads 233 or other interlocking surface features. These threaded portions 232 extend longitudinally vertically in the rod-receiving location 230 and are configured to threadingly engage threads formed on the outer surface of the inner receiver 208. Adjacent to the threaded portions 232 are two oppositely disposed smooth surfaces 234 that also run longitudinally vertically in the rod-receiving location 230. The smooth surfaces 234 provide a channel for unimpeded longitudinal/vertical translation of the inner receiver 208 relative to the outer receiver 204 when disposed therein. The smooth surfaces 234 may appear as vertical notches or recessed portions formed into the inner surface of the outer receiver 204. Hence, the inner surface of the outer receiver 204 includes both recessed regions 234 and non-recessed regions 232. The non-recessed regions 232 include threads 233 or other interlocking surface features. The recessed regions 234 are recessed with respect to the non-recessed regions 232. The recessed regions 234 are smooth surfaces that extend longitudinally vertically adjacent to the longitudinally extending non-recessed threaded regions 232 in the rod receiving location 230. The recessed regions 234 are configured to receive the arms of the inner receiver 208 such that the inner receiver 208 may translate vertically relative to the outer receiver 204 within the recessed regions 234. With the inner receiver 208 positioned within the recessed regions 234, the inner surface of the arms of the inner receiver 208 are flush with the non-recessed regions 232 of the inner surface of the outer receiver 204. In one variation, the recessed region 234 includes a first recessed region 278 and a second recessed region 280. The second recessed region 280 is deeper relative to the first recessed region 278, that is, the second recessed region extends radially outwardly from the inner surface of the arms 226 beyond the first recessed region 278 providing for a recessed region 234 wherein at least a portion of the recessed region 234 has a greater depth relative to the first recessed region 278 as seen in FIG. 20. The second recessed region 280 is sized and configured to receive larger tabs 244 formed on the fastener locking cap 206 as shown in FIG. 21. The larger tabs 244 are thicker and extend beyond the outer wall of the inner receiver. The first recessed region 278 is sized and configured to receive the inner receiver 208. The larger tabs 244 are radially thicker and, hence, the recessed region 234 is correspondingly sized to accommodate the thicker tabs 244. The tabs 244 are inserted into the longitudinal notches 260 of the inner receiver 208 to couple the fastener locking cap 206 to the inner receiver 208. The two notches 260 on the inner receiver 208 are located circumferentially opposite from each other and such that the inner receiver 208 may still be rotated from being adjacent or in juxtaposition to the smooth recessed regions 234 in an unlocked position to being adjacent or in juxtaposition to the threaded, non-recessed regions 232 in a locked position without the thicker tabs 244 coming into rotational interference with the intersection of the recessed and non-recessed regions 234, 232. FIGS. 33A, 33B and 34 illustrate the variation with a single recessed region 280. The outer surface of the outer receiver 204 may include two small holes 235 oppositely disposed in the arms 226 for permitting a reduction instrument or other instrument to grasp onto the receiver 204.

Turning now to FIG. 21, the fastener locking cap 206 will now be described. The fastener locking cap 206 includes an outer surface 236 and an inner surface 237 interconnected by a top surface 238 and a bottom surface 239 to define a substantially cylindrical shape. The fastener locking cap 206 is configured to fit inside the inner bore of the outer receiver 204. The outer surface 236 includes threads 240 or other interlocking surface feature configured to engage the threads or other interlocking surface feature 225 formed on the inner surface of the outer receiver 204 in the bone fastener-receiving location 224. The bottom surface 239 of the fastener locking cap 206 may be curved to conformingly accommodate the spherical or curved head of the bone screw head 214. As the fastener locking cap 206 is threaded downwardly into the inner bore of the outer receiver 204, the bottom surface 239 will engage at least part of the bone screw head 214 and force it against the seat or inner surface of the outer receiver 204 arresting or otherwise locking the bone fastener 202 in a desired angular position relative to the outer receiver 204. The fastener locking cap 206 also includes an inner bore 242 for accessing the driver connection feature 218 formed on the bone screw head 214. Further, the fastener locking cap 206 includes two oppositely disposed, upstanding tabs 244 that extend longitudinally upwardly from the fastener locking cap 206. The tabs 244 are narrow beams having curved outer surfaces that conform to the curved inner surface of the outer receiver 204.

Figure 22:
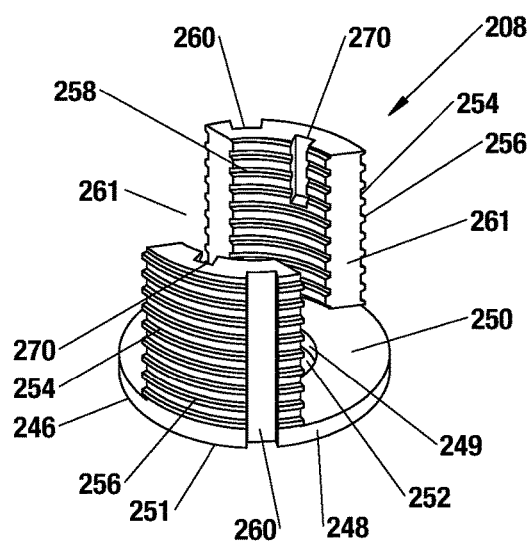
FIG. 22 is a top perspective view of an inner receiver according to the present invention.

With reference to FIG. 22, the inner receiver or inner tulip 208 will now be described in detail. The inner receiver 208 includes a circular base 246 and is sized and configured for insertion into the inner bore of the outer receiver 204. The base 246 includes an outer surface 248 and an inner surface 249 interconnected by a top surface 250 and a bottom surface 251. A central aperture 252 extends through the base 246 for accessing the driver connection feature 218 in the bone screw head 214 with an instrument for driving the bone fastener 202 into anatomy. Two upstanding, oppositely disposed arms 254 extend longitudinally upwardly from the top surface 250. The arms 254 are curved circumferential segments having a threaded outer surface 256 and a threaded inner surface 258. The threaded outer surface 256 is configured for threadingly engaging with the threaded portions 232 of the rod-receiving location 230 and the threaded inner surface 258 is configured for threadingly engaging with the threads on the set screw 210 as will be described in greater detail below. Of course, other interlocking surface features in lieu of threads may be employed. The outer surface 256 of each of the arms 254 includes a longitudinal notch 260 or tab engaging feature 260 that is sized and configured to receive or engage with the fastener locking cap tabs 244. The fastener locking cap 206 is interconnected with the inner receiver 208 by aligning the tabs 244 of the fastener locking cap 206 with the notches 260 of the inner receiver 208 and sliding the inner receiver 208 relative to the fastener locking cap 206 by any desired distance. Two oppositely disposed, substantially U-shaped channels 261 are defined between the arms 254 for receiving an elongate fixation member 212.

Referring back to FIG. 19, the set screw 210 is a substantially cylindrical object having an outer surface 262 interconnected with a top surface 263 and a bottom surface 264. The outer surface 262 includes threads 266 and is configured to fit inside the inner receiver 208 and threadingly engage with the threaded inner surface 258 of the inner receiver 208. Of course, other interlocking surface features in lieu of threads may be employed. The top surface 263 of the set screw 210 includes a driver-receiving connection or socket 268 configured for engaging the tip of a driving instrument for turning the set screw 210 into a lock position or unlock position. The bottom surface 264 of the set screw 210 may include a conforming surface that conforms to the outer contour of an elongate fixation member 212. As the set screw 210 is threadingly translated into threaded engagement with the inner receiver 208, it will bear down with force onto the elongate fixation member 212 to lock it into the desired position.

Still referencing FIG. 19, the elongate fixation member 212 is a typical spinal fixation rod having a solid cylindrical shape having a circular cross-section and a length that spans any number of vertebrae that are desired to be fixed. Only a short portion of the elongate fixation member 212 is pictured in FIG. 19 for exemplary purposes only. Although a spinal fixation rod is pictured, the use of any fixation member having any cross-section is within the scope of the present invention.

Still referring to FIG. 19, at least one optional spring 213 is provided between the inner receiver 208 and the fastener locking cap 206. Two springs 213 are shown in FIG. 19. The at least one spring 213 provides a bias force to raise the inner receiver 208 relative to the fastener locking cap 206 so that the z-axis position of the inner receiver 208, and hence, the z-axis position of the elongate fixation member 212 may be more easily adjusted. Spring-receiving areas may also be provided to help retain the at least one spring 213 in position.

Figure 23:
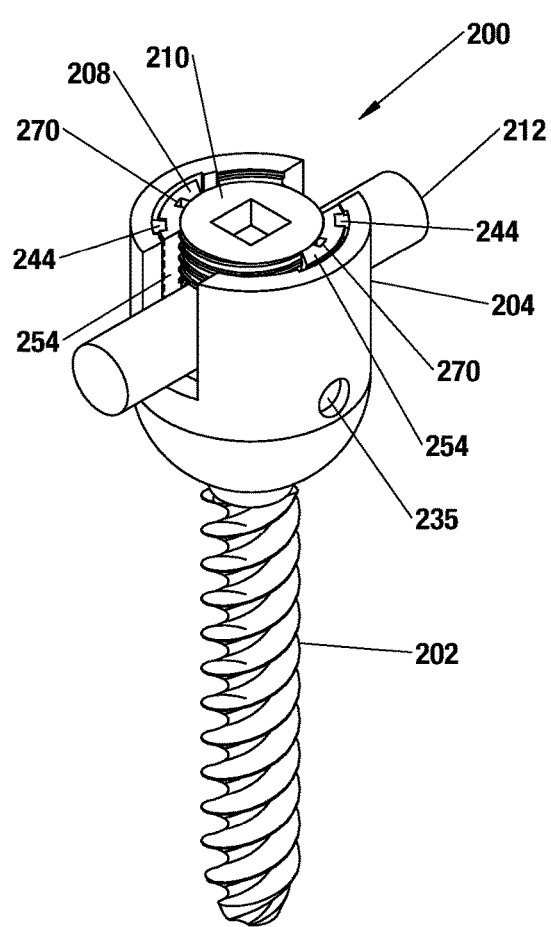
FIG. 23 is a top perspective view of a bone fastener system according to the present invention.
Figure 24:
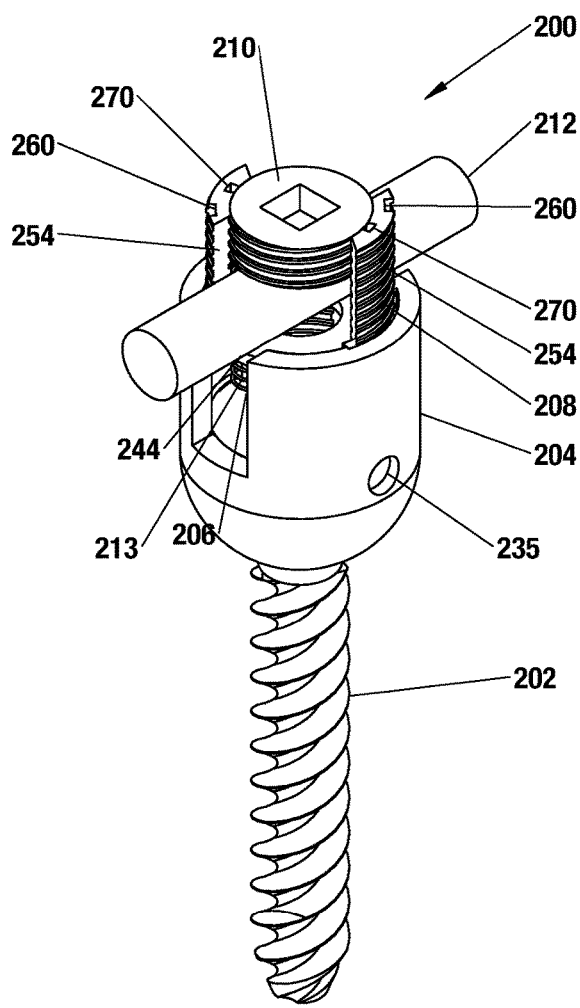
FIG. 24 is a top perspective view of a bone fastener system according to the present invention.

In use, the bone fixation system 200 is assembled by passing the shank portion 216 of the bone fastener 202 through the proximal opening 220 and into the distal opening 222 in the outer receiver 204 with the bone screw head 214 coming to rest in the seat of the bone fastener receiving location 224 of the outer receiver 204. An additional retainer (not shown) may be employed if the distal opening 222 is too large to retain the bone fastener head 214. The retainer forms an additional seating location for the bone fastener head 214 permitting it to be retained inside the outer receiver 204. The fastener locking cap 206 is coupled to the inner receiver 208 by sliding the tabs 244 into the notches 260 of the inner receiver 208. Both the fastener locking cap 206 and the inner receiver 208 are inserted into the inner bore of the outer receiver 204 such that the arms 254 of the inner receiver 208 are aligned with the smooth surfaces 234 of the outer receiver 204 so that inner receiver 208 and connected fastener locking cap 206 may telescope freely vertically within the inner bore of the outer receiver 204 for adjusting the height of the inner receiver 208, and hence, the height of the elongate fixation member 212 relative to the outer receiver 204. A driver instrument may then be inserted into the proximal opening 220 of the inner bore of the outer receiver 204 and through the central aperture 252 of the inner receiver 208 and through the bore 242 of the fastener locking cap 206 and into the driver connection feature 218 in the bone fastener head 214. The user may then rotate the driver to drive the bone fastener 202 into the anatomy. With the shank portion 216 delivered into bony anatomy, the outer receiver 204 is permitted to angulate with respect to the bone fastener 202. An elongate fixation member 212 is then placed into the channels 228, 261 and between the arms 254 of the inner receiver 208. A set screw 210 is placed into the inner receiver 208 such that its threads 266 engage the threads of the inner surface 258 of the arms 254. The set screw 210 is only slightly advanced into the inner receiver 208 such that the inner receiver 208 may still translate longitudinally relative to the outer receiver 204. Since the inner receiver 208 is advantageously free to translate longitudinally within the inner bore of the outer receiver 204, in particular, free to translate longitudinally within the rod-receiving location of the outer receiver 204, substantial z-axis translation is afforded for precisely locating the elongate fixation member 212 in the desired location custom to the anatomy. FIG. 23 illustrates the elongate fixation member 212 in a relatively low position along the z-axis, that is, the elongate fixation member 212 is in a position proximal to the head 214 of the bone fastener 202. The inner receiver 208 is also in a relatively low position along the z-axis in which the inner receiver 208 is proximal to the head 214 of the bone fastener 202. FIG. 23 illustrates the inner receiver 208 in an unlocked position relative to the outer receiver 204 as the arms 254 of the inner receiver 208 are adjacent to the smooth surfaces or recessed regions 234 of the outer receiver 204. FIG. 24 illustrates the elongate fixation member 212 in a relatively high position along the z-axis, that is, the elongate fixation member 212 is in a position most distal from the head 214 of the bone fastener 202. The inner receiver 208 is also in a relatively high position together with the elongate fixation member 212 along the z-axis in which the inner receiver 208 is distal to the head 214 of the bone fastener 202. FIG. 24 illustrates the inner receiver 208 in an unlocked position relative to the outer receiver 204 as the arms 254 of the inner receiver 208 are adjacent to the smooth surfaces or recessed regions 234 of the outer receiver 204. In the unlocked position, the inner receiver 208, which forms a seat for the elongated fixation member 212, together with the elongate fixation member 212 are free to translate longitudinally and the longitudinal, z-axis translation may be adjusted as desired until the desired position is achieved and locked in place.

Figure 26:
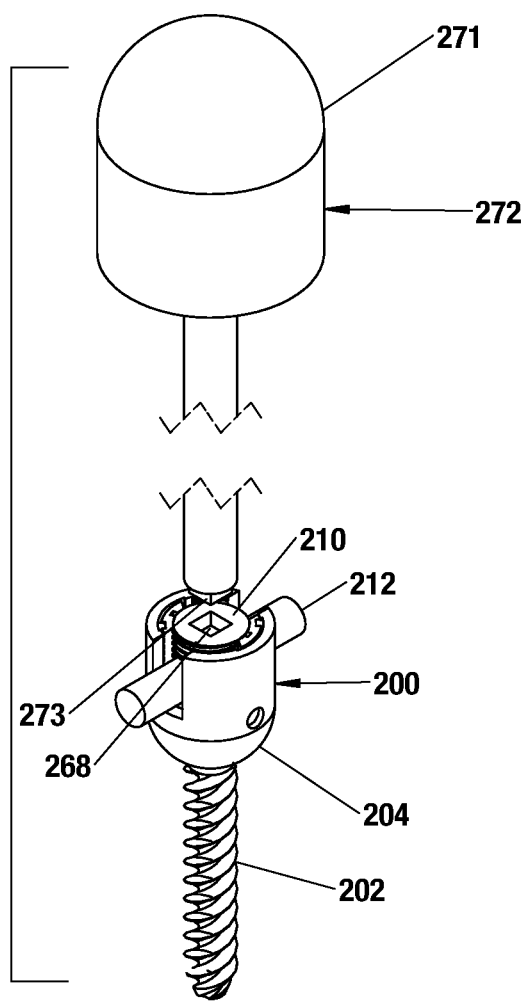
FIG. 26 is a top perspective view of a driver instrument and bone fixation system according to the present invention.
Figure 25:
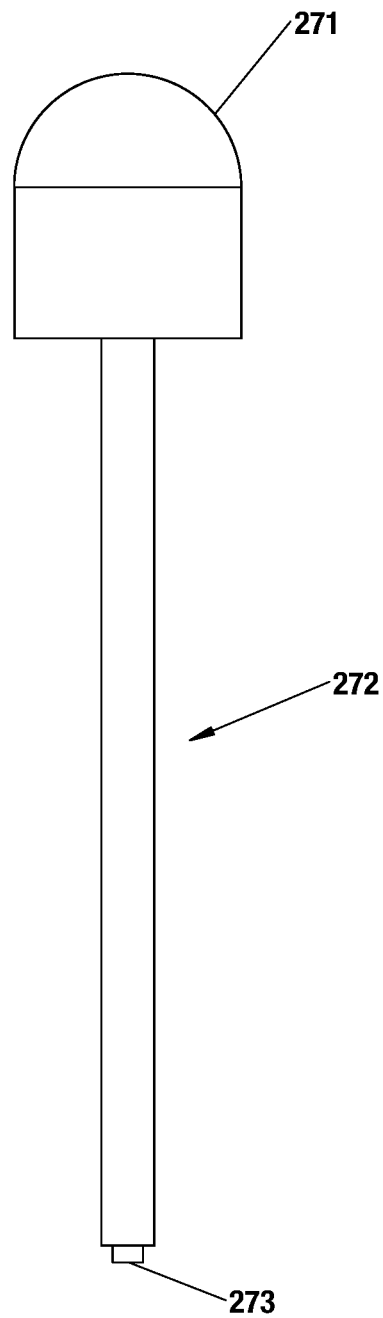
FIG. 25 is a side elevational view of a driver instrument according to the present invention.
Figure 27:
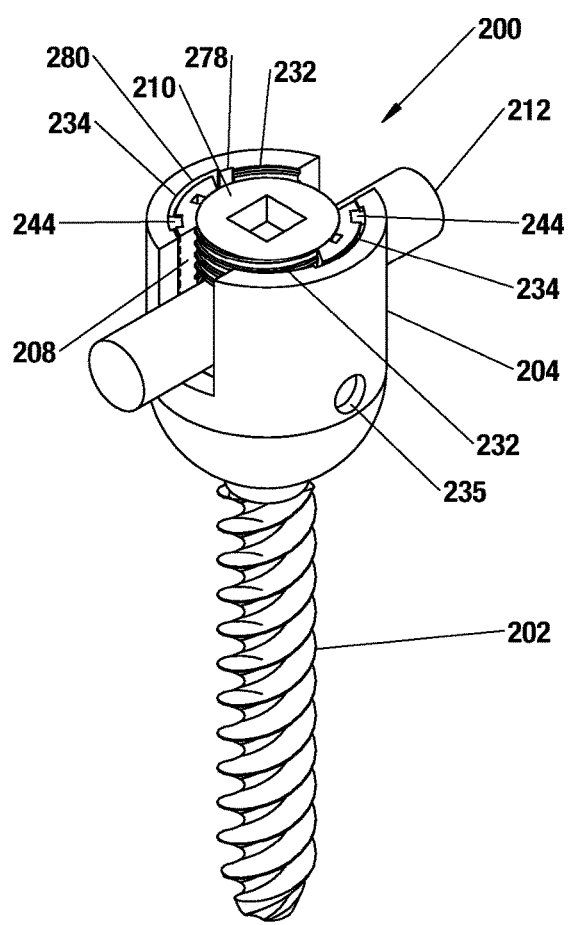
FIG. 27 is a top perspective view of a bone fixation system according to the present invention.
Figure 28:
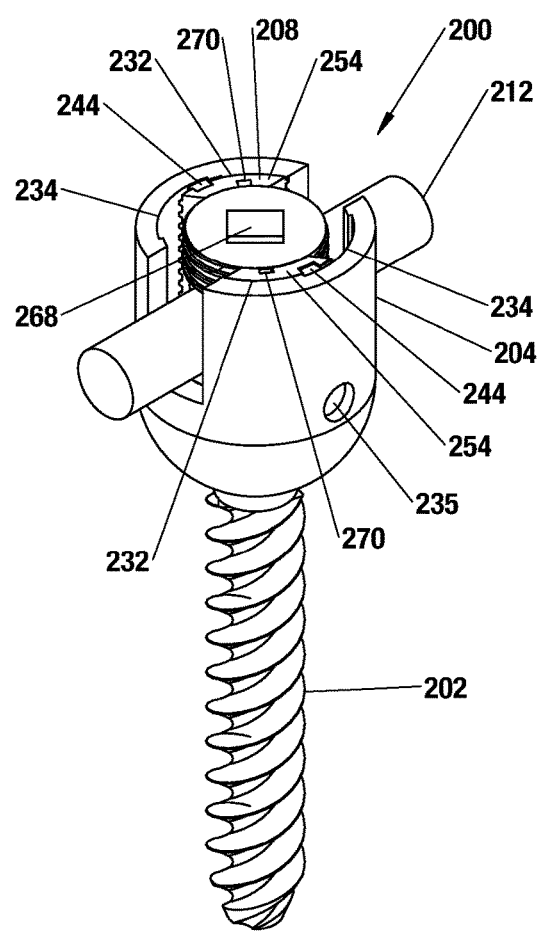
FIG. 28 is a top perspective view of a bone fixation system according to the present invention.

With the set screw 210 in position within the inner receiver 208, a driver instrument 272 of the type depicted in FIG. 25 is employed to turn the set screw 210. The driver instrument 272 includes a handle 271 at the proximal end and a distal tip 273 configured to engage the socket 268 on the set screw 210 as shown in FIG. 26. The driver instrument 272 rotates the set screw 210 translating it longitudinally downwardly onto the elongate fixation member 212. Throughout this time, the position of the elongate fixation member 212 along the z-axis and in the cephalad-caudal direction may be incrementally adjusted together with the angle of the outer receiver 204 relative to the bone fastener 202. The set screw 210 is advanced downwardly to precisely lock the desired position of these components. When downward force is exerted onto the elongate fixation member 212 with continued threaded advancement of the set screw 210, the elongate fixation member 212 will bear down with force against the circular base 246 of the inner receiver 208. Also, the z-axis translation of the elongate fixation member 212 relative to the inner receiver will be substantially arrested. With continued rotation of the set screw 210 with the driver instrument 272, the angular moment of the set screw 210 will also turn the inner receiver 208 relative to the outer receiver 204 such that the arms 254 of the inner receiver 208 move from being in contact with or adjacent to the smooth surfaces or recessed regions 234 shown in FIG. 27 and into threaded engagement with the threaded portions or non-recessed regions 232 of the outer receiver 204 in the rod-receiving location 230 as shown in FIG. 28. Such rotation of the inner receiver 208 relative to the outer receiver 204 will result in locking or arresting the z-axis, or vertical or longitudinal position of the elongate fixation member 212 relative to the outer receiver 204. Of course, reverse rotation of the set screw 210 will unlock the z-axis position of the inner receiver 208 and elongate fixation member 212 so that it can be conveniently readjusted and repositioned as needed. Simultaneously the relative rotation of the inner receiver 208 will also rotate the connected fastener locking cap 206 within the threads 240 of the bone fastener receiving location 224 resulting in the locking down and setting of the angular orientation of the outer receiver 204 relative to the bone fastener 202. Hence, the present invention permits the set screw 210 to be used to lock down simultaneously not only the exact position of the elongate fixation member 212 relative to the outer receiver 204 in at least the longitudinal direction, but also, the angulation of the outer receiver 204 relative to the bone fastener 202. Furthermore, the fastener locking cap 206 is movable relative to the inner receiver 208 which advantageously allows the distance between the inner receiver 208 and the fastener locking cap 206 to be adjusted. This adjustment of the distance between the inner receiver 208 and the fastener locking cap 206 is assisted by the presence of the at least one spring 213 located between the inner receiver 208 and the fastener locking cap 206 which biases these two elements apart.

Furthermore, the inner receiver 208 may include a notch 270 formed in each arm 254 that extends radially from the inner surface 258 of the arms 254. The at least one notch 270 is clearly shown in FIG. 22. Alternatively, the at least one notch 270 may be formed in the top surface of each arm 254. The notches 270 are sized and configured for receiving a tool 274 shown in FIGS. 29A and 29B for rotating the inner receiver 208 relative to the outer receiver 204 independently of the set screw 210, that is the inner receiver 208 may be rotated relative to the outer receiver 204 at any time without the use of a set screw 210 or prior to the insertion of a set screw 210 in order to lock down the z-axis distance of the elongate fixation member 212 and inner receiver 208 relative to the outer receiver 204. FIG. 31B illustrates the driving tool 274 engaging the inner receiver 208 in an unlocked position and FIG. 32B illustrates the driving tool 274 engaging the inner receiver 208 in a locked position in the absence of a set screw 210.

Figure 30A:
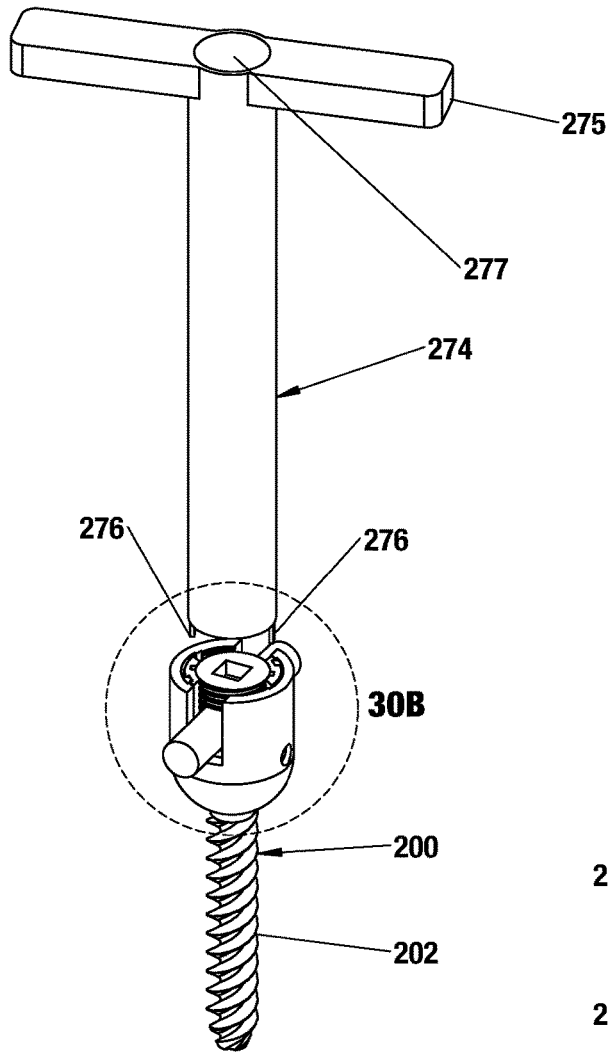
FIG. 30A is a top perspective and sectional view of a tool and bone fixation system according to the present invention.
Figure 30B:
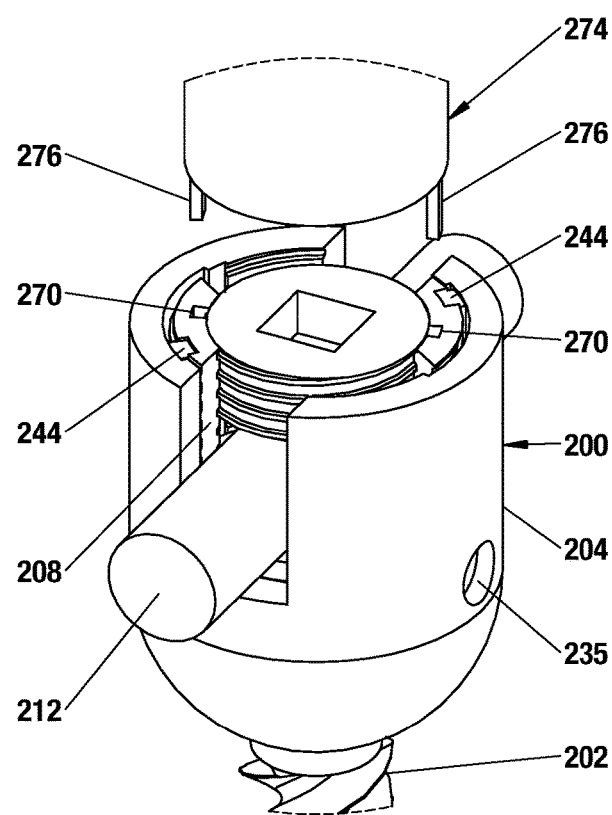
FIG. 30B is a sectional view of section 30B of FIG. 30A of a tool and bone fixation system according to the present invention.
Figure 31A:
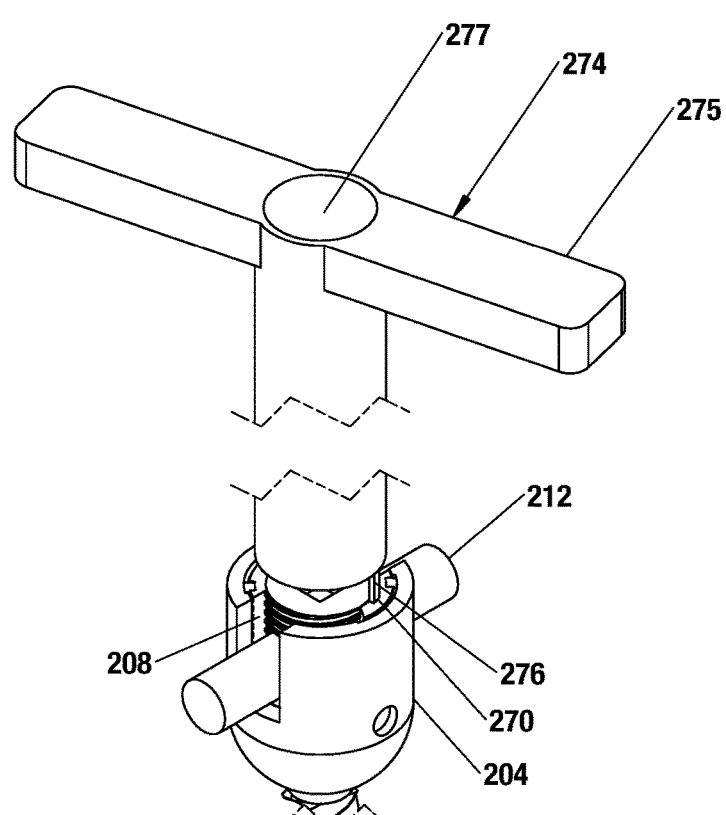
FIG. 31A is a top perspective and sectional view of a tool and bone fixation system according to the present invention.
Figure 32A:
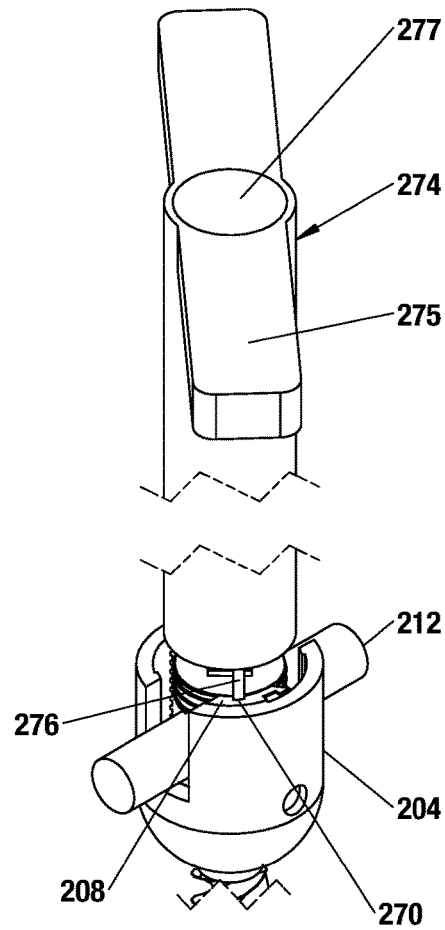
FIG. 32A is a top perspective and sectional view of a tool and bone fixation system according to the present invention.

FIGS. 29A and 29B illustrate the tool 274 having a handle 275 at the proximal end and distal tip having two oppositely disposed prongs 276 that are configured for engaging the oppositely disposed notches 270 of the inner receiver 208 to rotate the inner receiver 208 independently of the set screw 210. The tool 274 may include a central lumen 277 extending longitudinally within the tool 274 between an opening at the proximal end and an opening at the distal end. FIGS. 30A and 30B illustrates the tool 274 above the bone fixation system 200 with the distal prongs 276 substantially aligned with the notches 270. FIG. 31A illustrates the tool 274 with prongs 276 inserted into the notches 270 with the inner receiver 208 in an unlocked position and FIG. 32A illustrates the tool 274 with prongs 276 inserted into the notches 270 and the inner receiver 208 rotated into a locked position in which the arms 254 of the inner receiver 208 are engaging the threaded portions 232 of the outer receiver 204.

Turning now to FIG. 33A, an alternative outer receiver or outer tulip 204 for use with the bone fixation system 200 is shown. The outer receiver 204 includes all of the same features as described above wherein like reference numbers are used to describe like parts. In the variation of FIG. 33A, the recessed region 234 of the outer receiver 204 includes a single recessed region 280 that accommodates the relatively narrower tabs 244 of the bone fastener lock 206 of FIG. 33B. The assembly of FIG. 34 shows the outer receiver 204 with a single recessed region 280 in an unlocked position relative to the inner receiver 208.

When downward force is exerted onto the elongate fixation member 212, with continued threaded advancement of the set screw 210, z-axis translation will be substantially arrested, as the angular moment or torque of the set screw 210 will turn the inner receiver 208 such that its arms 254 move from the smooth surfaces 234 and into threaded engagement with the threaded portions 232 of the rod-receiving location. Such rotation of the inner receiver 208 relative to the outer receiver 204 will result in locking the z-axis, or vertical or longitudinal position of the elongate fixation member 212 relative to the outer receiver 204. Simultaneously the relative rotation of the inner receiver 208 will also rotate the connected fastener locking cap 206 within the threads 225 of the bone fastener receiving location 224 resulting in the locking down and setting of orientation/angulation of the outer receiver 204 relative to the bone fastener 202. Hence, the present invention permits the set screw 210 to be used to lock down not only the exact position of the rod, but also, the angulation of the outer receiver 204 relative to the bone fastener 202. Furthermore, the fastener locking cap 206 is movable relative to the inner receiver 208 which advantageously allows the distance between the inner receiver 208 and the fastener locking cap 206 to be adjusted. The inner receiver 208 may include a notch 270 formed in the arms 254 such as the top surface of the arms 254 for receiving a tool for rotating the inner receiver 208 relative to the outer receiver 204 without the use of a set screw 210 or prior to the insertion of a set screw 210 to lock down the z-axis distance of the elongate fixation member 212 relative to the outer receiver 204.

Figure 35:
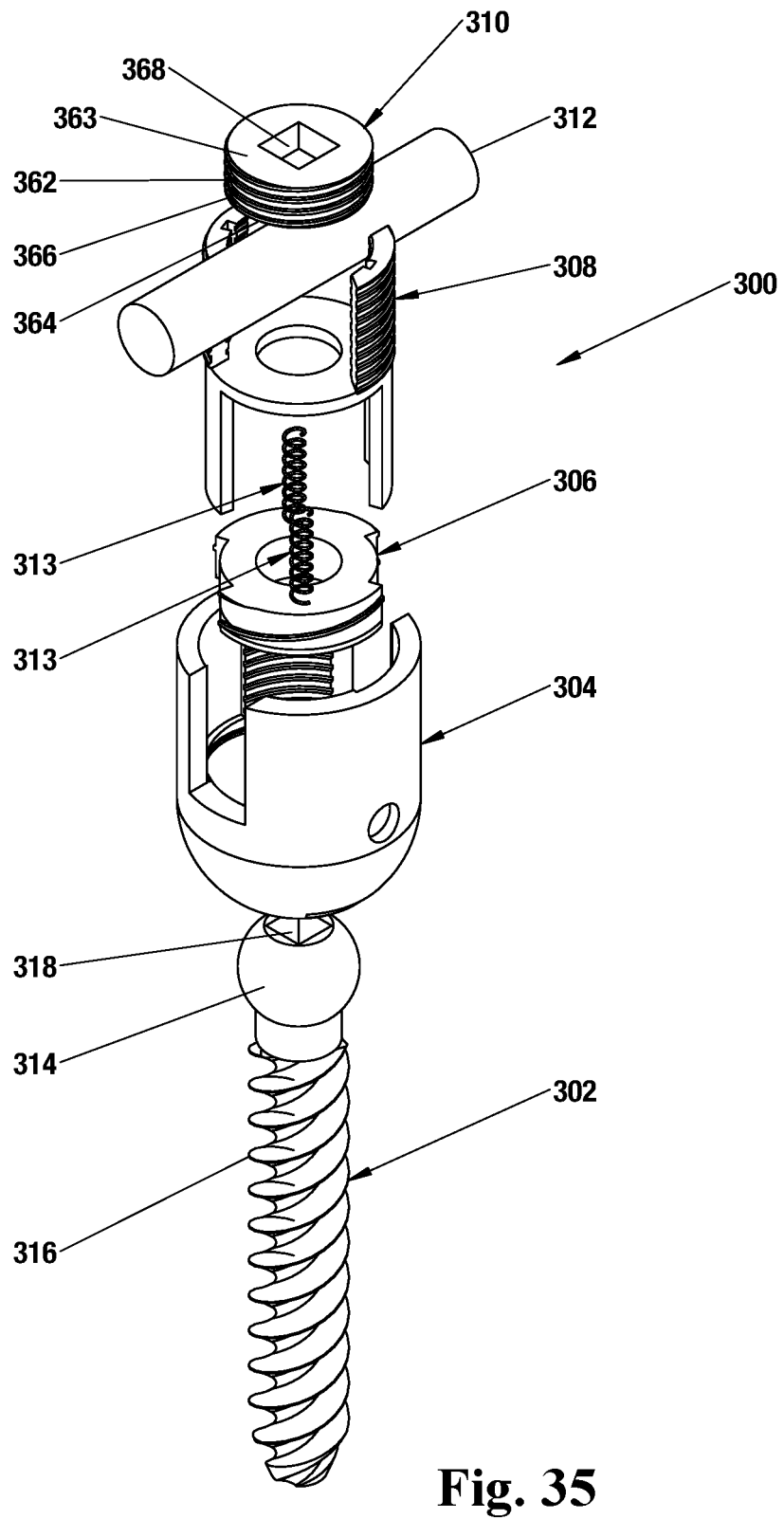
FIG. 35 is a top perspective, exploded view of a bone fixation system according to the present invention.

Turning now to FIG. 35, another variation of the bone fixation system 300 will now be described. The bone fixation system 300 of the present invention includes a bone fastener 302, an outer receiver or outer tulip 304 coupled to the bone fastener 302, a fastener locking cap 306 interconnected with an inner receiver or inner tulip 308, and a rod locking cap or set screw 310. The bone fixation system 300 may also include an elongate fixation member or connecting rod 312 and at least one spring 313 disposed between the fastener locking cap 306 and inner receiver 308. It should be noted, however, that although the bone fixation system 300 is generally illustrated and described as a single assembly for use with a single connecting rod 312, any combination of bone fixation systems 300 and connecting rods 312 can be employed during a surgical procedure. For example, in a single level spinal fixation procedure, two bone fixation systems 300 can receive a single connecting rod 312 along one side of the spine and two bone fixation systems 300 can receive another connecting rod 312 along the opposite side of the spine. A multiple level spinal fixation procedure, however, will generally require additional bone fixation systems 300. In addition, the bone fixation systems 300 need not be coupled to adjacent vertebral bodies, but rather, the bone fixation systems 300 can be positioned so as to skip adjacent vertebral bodies if desired. The bone fixation system 300 can be composed of any suitable material, such as titanium, stainless steel, metal, metal alloys, polymers, synthetic polymers such as polyether ether ketone (PEEK), plastics or any other sufficiently rigid and strong material which is biologically compatible and can maintain its strength in vivo for at least six months. The various components of the bone fixation system 300 can be made of materials that are different from the other components of the system 300.

Still referencing FIG. 35, the bone fastener 302 is configured to engage the anatomy to couple the bone fixation system 300 to the anatomy. The bone fastener 302 includes a head 314 at a proximal end and an elongate threaded shank portion 316 extending between the head 314 and a distal end along a longitudinal axis. The bone fastener 302 is configured as a typical bone screw; however, the invention is not so limited and any fastener or other-shaped anchor may be employed. The bone fastener 302 may be a self-tapping bone screw having at least one cutting flute. Alternatively, the bone screw may require a hole to be pre-tapped prior to insertion. The head 314 can be generally arcuate having a curved or bulbous outer surface and may be spherical or partially spherical in shape. The head 314 can include a driver connection feature 318 or socket at the proximal end for mating with any type of driver such as a driver with a hexagonal-shaped tip to enable the application of torque to drive the bone fastener 302 into the anatomy.

Figure 36:
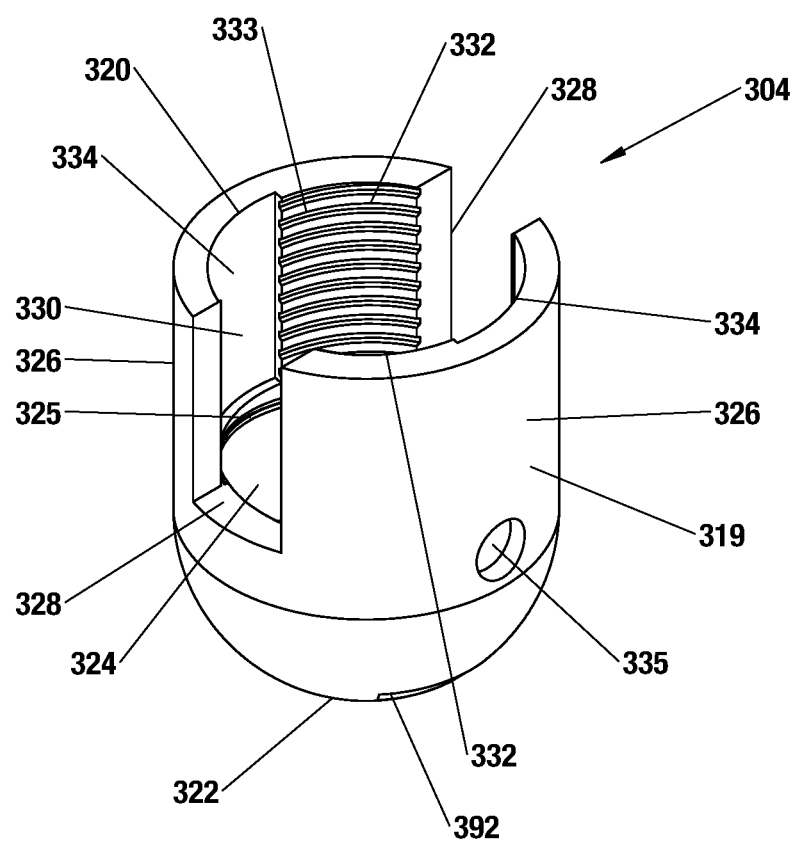
FIG. 36 is a top perspective view of an outer receiver according to the present invention.

Turning now to FIG. 36, the outer receiver or outer tulip 304 will now be described in detail. The outer receiver 304 includes a sidewall 319 having an outer surface and an inner surface. The sidewall 319 forms a proximal opening 320 at the proximal end leading into a substantially cylindrical bore that extends to a distal opening 322 at the distal end of the outer receiver 304. The distal opening 322 is configured for receiving at least a part of the shank portion 316 and/or bone fastener head 314 of the bone fastener 302. The inner surface of the outer receiver 304 at the distal end defines a bone fastener-receiving location 324. The inner surface of the outer receiver 304 in the bone fastener-receiving location 324 is contoured to form a conforming seat for the bone fastener head 314 such that when the bone fastener 302 is inserted into the distal opening 322, the bone fastener 302 may freely pivot and angulate polyaxially unimpeded relative to the outer receiver 304 as well as rotate about the longitudinal axis of the shank portion 316. The inner surface of the outer receiver 304 in the bone fastener-receiving location 324 includes threads 325 or other interlocking surface features configured for engagement with threads or other interlocking surface features on the outer surface of the fastener locking cap 306 as will be described in greater detail below.

Still referencing FIG. 36, the sidewall 319 of the outer receiver 304 forms two upstanding, oppositely disposed arms 326. The two arms 326 are spaced apart from each other to define at least one channel 328 in the sidewall 319. The channels 328 comprise two oppositely disposed, substantially U-shaped spaces that interconnect with the proximal opening 320 and the inner bore of the outer receiver 304. Each channel 328 is shaped to receive an elongate fixation member 312 such as a spinal fixation rod or other elgonate member to be connected to the outer receiver 304 by placement of the rod 312 into the channels 328. The outer receiver 304 includes a rod-receiving location 330 along at least part of the longitudinal length of the outer receiver 304. In the rod-receiving location 330 of the outer receiver 304, the inner surface defines at least two oppositely disposed threaded portions 332 having threads 333. Of course, any interlocking surface features in lieu of threads may be employed. These threaded portions 332 extend longitudinally vertically in the rod-receiving location 330 and are configured to threadingly engage threads formed on the outer surface of the inner receiver 308. Adjacent to the threaded portions 332 are two oppositely disposed smooth surfaces 334 that also run longitudinally vertically in the rod-receiving location 330. The smooth surfaces 334 provide a channel for unimpeded longitudinal, vertical translation of the inner receiver 308 relative to the outer receiver 304. The smooth surfaces 334 may appear as vertical notches or recessed portions formed into the inner surface of the outer receiver 304. Hence, the inner surface of the outer receiver 304 includes both recessed regions 334 and non-recessed regions 332. The non-recessed regions 332 include threads 333. The recessed regions 334 are recessed with respect to the non-recessed regions 332. The recessed regions 334 are smooth surfaces that extend longitudinally vertically adjacent to the longitudinally extending non-recessed threaded regions 332 in the rod receiving location 330. The recessed regions 334 are configured to receive the arms of the inner receiver 308 such that the inner receiver 308 may translate vertically relative to the outer receiver 304 within the recessed regions 334. With the inner receiver 308 positioned within the recessed regions 334, the outer surface of the arms of the inner receiver 308 are flush with the non-recessed regions 332 of the inner surface of the outer receiver 304 such that the threaded outer surface of the inner receiver may be rotated into the threads of the inner surface of the outer receiver. The outer surface of the outer receiver 304 may include two small holes 335 oppositely disposed in the arms 326 for permitting a reduction instrument or other instrument to grasp onto the receiver 304. The outer receiver 304 also includes two oppositely disposed slots 392 in the distal end of the outer receiver 304 in the bone fastener receiving location 324. The slots 392 are sized and configured for receiving the tabs 344 that extend downwardly from the inner receiver 308.

Figure 37:
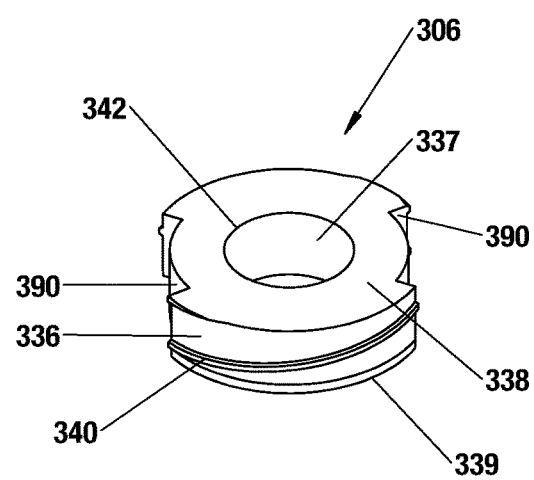
FIG. 37 is a top perspective view of a fastener locking cap according to the present invention.

Turning now to FIG. 37, the fastener locking cap 306 will now be described. The fastener locking cap 306 includes an outer surface 336 and an inner surface 337 interconnected by a top surface 338 and a bottom surface 339 to define a substantially cylindrical shape. The fastener locking cap 306 is configured to fit inside the inner bore of the outer receiver 304. The outer surface 336 includes threads 340 configured to engage the threads 325 formed on the inner surface of the outer receiver 304 in the bone fastener-receiving location 324. The bottom surface 339 of the fastener locking cap 306 may be curved to conformingly accommodate the spherical or curved head of the bone screw head 314. As the fastener locking cap 306 is threaded downwardly into the inner bore of the outer receiver 304, the bottom surface 339 will engage at least part of the bone screw head 314 and force it against the seat or inner surface of the outer receiver 304 arresting or otherwise locking the bone fastener 302 in a desired angular position relative to the outer receiver 304. Rotation of the fastener locking cap 306 in the opposite direction will unlock the angulation of the fastener 302. The fastener locking cap 306 also includes an inner bore 342 for accessing the driver connection feature 318 formed on the bone screw head 314. Furthermore, the fastener locking cap 306 includes two oppositely disposed, notches 390 or tab engaging features that extend radially inwardly from the outer surface 336. The notches 390 are sized and configured to receive tabs 344 formed on the inner receiver 308.

Figure 38A:
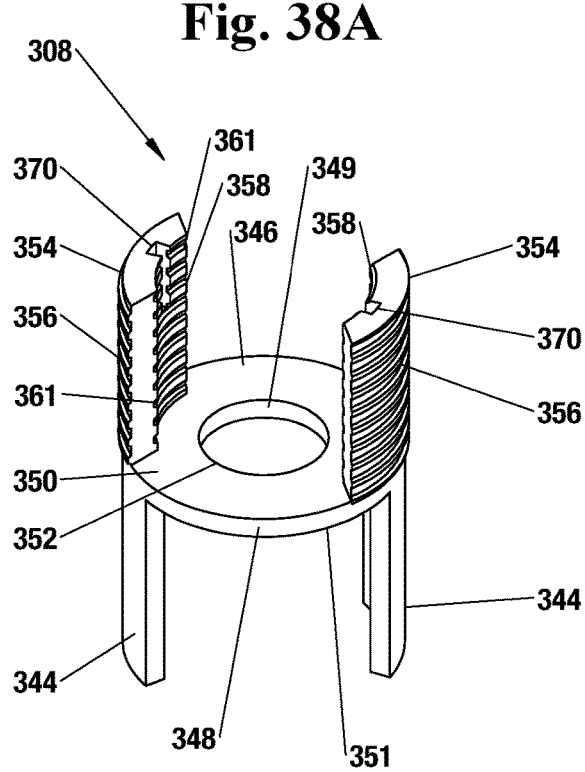
FIG. 38A is a top perspective view of an inner receiver according to the present invention.
Figure 38B:
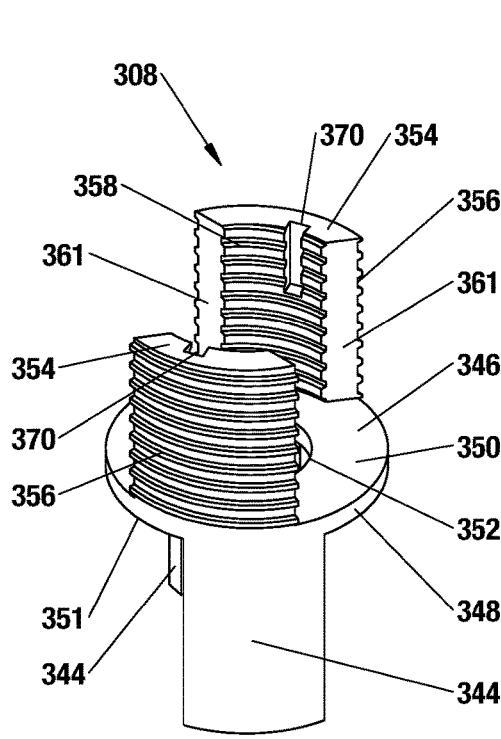
FIG. 38B is a top perspective view of an inner receiver according to the present invention.

With reference to FIGS. 38A and 38B, the inner receiver or inner tulip 308 will now be described in detail. The inner receiver 308 includes a circular base 346 and is sized and configured for insertion into the inner bore of the outer receiver 304. The base 346 includes an outer surface 348 and an inner surface 349 interconnected by a top surface 350 and a bottom surface 351. A central aperture 352 extends through the base 346 for accessing the driver connection feature 319 in the bone screw head 314 with an instrument for driving the bone fastener 302 into anatomy. Two upstanding, oppositely disposed arms 354 extend longitudinally upwardly from the top surface 350. The arms 354 are curved circumferential segments having a threaded outer surface 356 and a threaded inner surface 358. Of course, any interlocking surface in lieu of threads may be employed. The threaded outer surface 356 is configured for threadingly engaging with the threaded portions 332 of the rod-receiving location 330 and the threaded inner surfaces 358 are configured for threadingly engaging with the threads on the set screw 310. The inner receiver 308 includes two oppositely disposed tabs 344 that extend downwardly from the bottom surface 351. The tabs 344 are circumferential segments that are sized and configured to fit within the notches 390 of the fastener locking cap 306. The fastener locking cap 306 is interconnected with the inner receiver 308 by aligning the tabs 344 of the of the inner receiver 308 with the notches 390 of the inner receiver 308 and sliding the inner receiver 308 relative to the fastener locking cap 306 by any desired distance. Two oppositely disposed, substantially U-shaped channels 361 are defined between the arms 354 for receiving an elongate fixation member 312.

Referring back to FIG. 35, the set screw 310 is a substantially cylindrical object having an outer surface 362 interconnected with a top surface 363 and a bottom surface 364. The outer surface 362 includes threads 366 and is configured to fit inside the inner receiver 308 and threadingly engage with the threaded inner surface 358 of the inner receiver 308. The top surface 363 of the set screw 310 includes a driver receiving connection or socket 368 configured for engaging the tip of a driving instrument such as the instrument 272 shown in FIGS. 25 and 26 for turning the set screw 310 into a locked position or unlocked position. The bottom surface 364 of the set screw 310 may include a conforming surface that conforms to the outer contour of an elongate fixation member 312. As the set screw 310 is threaded downwardly into threaded engagement with the inner receiver 308, it will bear down with force onto the elongate fixation member 312 to lock it into the desired position. Rotation of the set screw 310 in the opposite direction will unlock the elongate fixation member 312.

Still referencing FIG. 35, the elongate fixation member 312 is a typical spinal fixation rod having a solid cylindrical shape having a circular cross-section and a length that spans any number of vertebrae that are to be fixed. Only a short portion of the elongate fixation member 312 is pictured in FIG. 35 for exemplary purposes only. Although a spinal fixation rod is pictured, the use of any fixation member having any cross-section is within the scope of the present invention.

Still referring to FIG. 35, at least one optional spring 313 is provided between the inner receiver 308 and the fastener locking cap 306. Two springs 313 are shown in FIG. 35. The at least one spring 313 provides a bias force to raise the inner receiver 308 relative to the fastener locking cap 306 so that the z-axis position of the inner receiver 308, and hence, the longitudinal, z-axis position of the elongate fixation member 312 may be more easily adjusted. Spring-receiving areas may also be provided to help retain the at least one spring 313 in position.

Figure 42C:
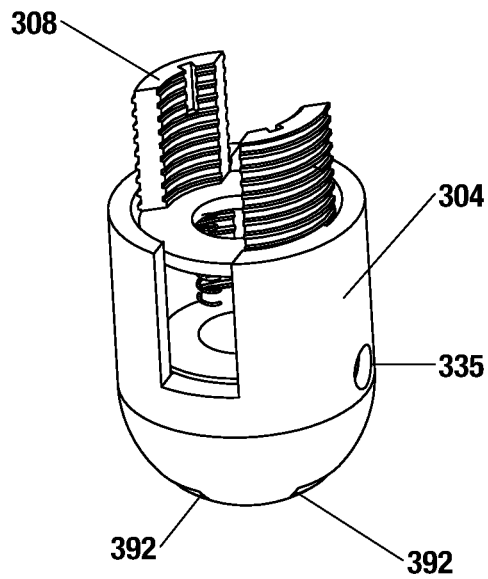
FIG. 42C is a top perspective view of a bone fixation system without a set screw and bone fastener according to the present invention.
Figure 42D:
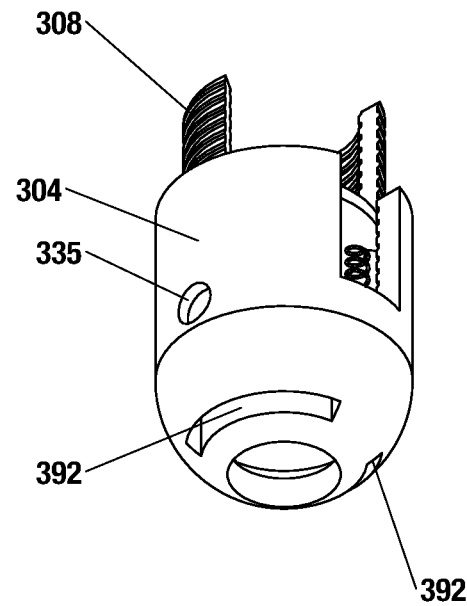
FIG. 42D is a bottom perspective view of a bone fixation system without a set screw and bone fastener according to the present invention.
Figure 42E:
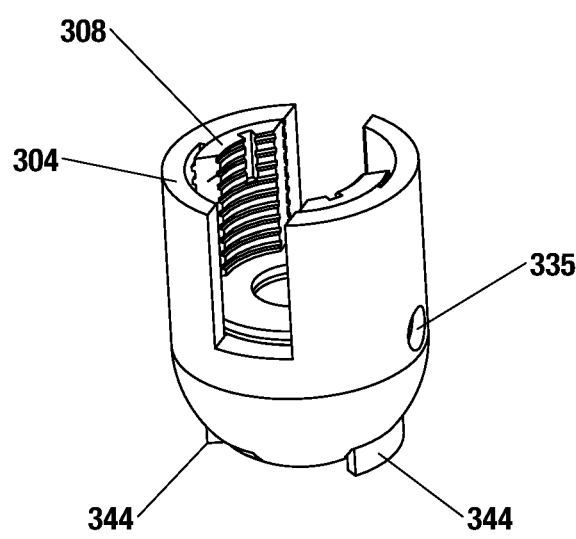
FIG. 42E is a top perspective view of a bone fixation system without a set screw and bone fastener according to the present invention.
Figure 42F:
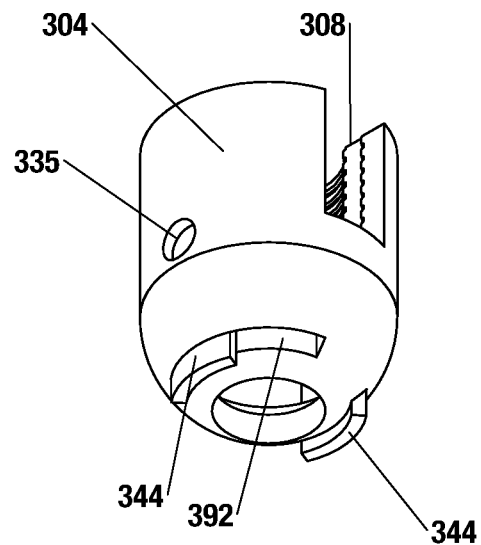
FIG. 42F is a bottom perspective view of a bone fixation system without a set screw and bone fastener according to the present invention.
Figure 43:
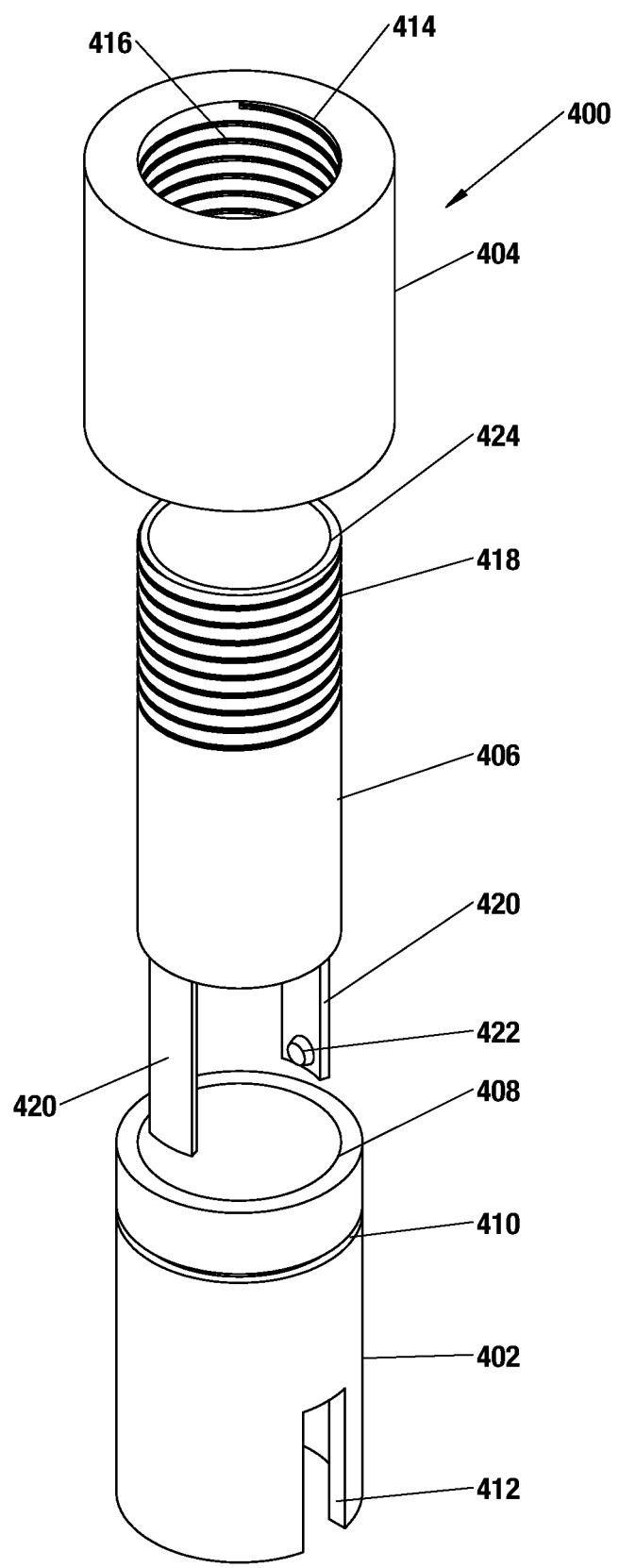
FIG. 43 is a top perspective, exploded view of a rod reduction instrument according to the present invention.

In use, the bone fixation system 300 is assembled by passing the shank portion 316 of the bone fastener 302 through the proximal opening 320 and into the distal opening 322 in the outer receiver 304 with the bone screw head 314 coming to rest in the seat of the bone fastener receiving location 324 of the outer receiver 304. An additional retainer (not shown) may be employed if the distal opening 322 is too large to retain the bone fastener head 314. The retainer forms an additional seating location for the bone fastener head 314 permitting it to be retained inside the outer receiver 304. The fastener locking cap 306 is coupled to the inner receiver 308 by sliding the tabs 344 into the notches 390 of the fastener locking cap 306. The distance between the inner receiver 308 and the fastener locking cap may be adjusted as desired. Both the fastener locking cap 306 and the inner receiver 308 are inserted into the inner bore of the outer receiver 304 such that the arms 354 of the inner receiver 308 are aligned with the smooth surfaces 334 of the outer receiver 304 so that inner receiver 308 and connected fastener locking cap 306 may telescope freely vertically within the inner bore of the outer receiver 304 for adjusting the height of the inner receiver 308, and hence, the height of the elongate fixation member 312 relative to the outer receiver 304. A driver instrument may then be inserted into the proximal opening 320 of the inner bore of the outer receiver 304 and through the central aperture 352 of the inner receiver 308 and through the bore 342 of the fastener locking cap 306 and into the driver connection feature 318 in the bone fastener head 314. The user may then rotate the driver to drive the bone fastener 302 into the anatomy. With the shank portion 316 delivered into bony anatomy, the outer receiver 304 is permitted to angulate with respect to the bone fastener 302. An elongate fixation member 312 is then placed into the channels 328, 361 and between the arms 354 of the inner receiver 308. A set screw 310 is placed into the inner receiver 308 such that its threads 366 engage the threads of the inner surface 358 of the arms 354. The set screw 310 is only slightly advanced into the inner receiver 308 such that the inner receiver 308 may still translate longitudinally relative to the outer receiver 304. Since the inner receiver 308 is advantageously free to translate longitudinally within the inner bore of the outer receiver 304, in particular, free to translate longitudinally within the rod-receiving location 330 of the outer receiver 304, substantial z-axis translation is advantageously afforded for precisely locating the elongate fixation member 312 in the desired location custom to the anatomy while keeping the elongate fixation member connected to the bone fixation system and hence to the anatomy without it popping out of position. FIGS. 39A, 39B, 41A, and 41B illustrate the elongate fixation member 312 in a relatively low position along the z-axis, that is, the elongate fixation member 312 is in a position proximal to the head 314 of the bone fastener 302. The inner receiver 308 is also in a relatively low position along the z-axis in which the inner receiver 308 is proximal to the head 314 of the bone fastener 302. As such, the tabs 344 of the inner receiver 308 extend through the slots 392 in the outer receiver 304. The tabs 344 extending through the slots 392 are clearly shown in FIGS. 42E and 42F. FIGS. 39A, 39B, 41A, and 41B illustrate the inner receiver 308 in a locked position relative to the outer receiver 304 as the arms 354 of the inner receiver 308 are adjacent to the threaded portions 332 of the outer receiver 304. FIGS. 40A, 40B, 42A and 42B illustrate the elongate fixation member 312 in a relatively high position along the z-axis, that is, the elongate fixation member 312 is in a position most distal from the head 314 of the bone fastener 302. The inner receiver 308 is also in a relatively high position together with the elongate fixation member 312 longitudinally along the z-axis in which the inner receiver 308 is distal to the head 314 of the bone fastener 302. In the high position, the tabs 344 do not protrude through slots 392 as can be seen in FIGS. 42C and 42D. FIGS. 40A, 40B, 42A and 42B illustrates the inner receiver 308 in an locked position relative to the outer receiver 304 as the arms 354 of the inner receiver 308 are adjacent to the threaded portions 332 of the outer receiver 304. In an unlocked state, the inner receiver 308, which forms a seat for the elongated fixation member 312, together with the elongate fixation member 312 are free to translate longitudinally and the longitudinal, z-axis translation may be adjusted as desired until the desired position is achieved and locked in place.

With the set screw 310 in position within the inner receiver 308, a driver instrument 272 of the type depicted in FIG. 25 is employed to turn the set screw 310. The driver instrument 272 is configured to engage the socket 368 on the set screw 310. The driver instrument 272 rotates the set screw 310 translating it longitudinally downwardly onto the elongate fixation member 312. Throughout this time, the position of the elongate fixation member 312 along the z-axis and in the cephalad-caudal or lateral direction may be adjusted. The angle of the outer receiver 304 relative to the bone fastener 302 is also adjusted at the same time. Advantageously, these adjustments may be made incrementally with the positions be locked and unlocked as needed until final positioning is achieved. The set screw 310 is advanced downwardly to precisely lock the desired position of these components. When downward force is exerted onto the elongate fixation member 312 with continued threaded advancement of the set screw 310, the elongate fixation member 312 will bear down with force against the circular base 346 of the inner receiver 308. Also, the z-axis translation of the elongate fixation member 312 will be substantially arrested. With continued rotation of the set screw 310 with the driver instrument 272, the angular moment of the set screw 310 will also turn the inner receiver 308 relative to the outer receiver 304 such that the arms 354 of the inner receiver 308 move from being in contact with or adjacent to the smooth surfaces or recessed regions 334 and into threaded engagement with the threaded portions or non-recessed regions 332 of the outer receiver 304 anywhere in the rod-receiving location 330. Such rotation of the inner receiver 308 relative to the outer receiver 304 will result in locking or arresting the z-axis, or vertical/longitudinal position of the elongate fixation member 312 relative to the outer receiver 304. Of course, reverse rotation of the set screw 310 will unlock the z-axis position of the inner receiver 308 and elongate fixation member 312 so that it can be conveniently readjusted and repositioned as needed for custom and accurate rod placement. Simultaneously, the relative rotation of the inner receiver 308 will also rotate the connected fastener locking cap 306 within the threads 340 of the bone fastener receiving location 324 resulting in the locking down and setting of the angular orientation of the outer receiver 304 relative to the bone fastener 302. Hence, the present invention permits the set screw 310 to be used to lock down simultaneously not only the exact position of the elongate fixation member 312 relative to the outer receiver 304 in at least the longitudinal direction, but also, the angulation of the outer receiver 304 relative to the bone fastener 302. Furthermore, the fastener locking cap 306 is movable relative to the inner receiver 308 which advantageously allows the distance between the inner receiver 308 and the fastener locking cap 306 to be adjusted. This adjustment of the distance between the inner receiver 308 and the fastener locking cap 306 is assisted by the presence of the at least one spring 313 located between the inner receiver 308 and the fastener locking cap 306 which biases these two elements apart. The variation of the bone fixation system of FIG. 35 is substantially identical to the variation shown in FIG. 19 with the exception that the tabs are located on the inner receiver in system 300 and extend downwardly to couple with the fastener locking cap, whereas, in system 200 the tabs are located on the fastener locking cap and extend upwardly to couple with the inner receiver.

Furthermore, the inner receiver 308 may include a notch 370 formed in each arm 254 that extends radially from the inner surface 358 of the arms 354. The at least one notch 370 is clearly shown in FIGS. 38A and 38B. Alternatively, the at least one notch 370 may be formed in the top surface of each arm 354. The notches 370 are sized and configured for receiving a tool 274 of the like shown in FIGS. 29A and 29B for rotating the inner receiver 308 relative to the outer receiver 304 independently of the set screw 310, that is the inner receiver 308 may be rotated relative to the outer receiver 304 at any time without the use of a set screw 310 or prior to the insertion of a set screw 310 in order to lock down the longitudinal, z-axis distance of the elongate fixation member 312 and inner receiver 308 relative to the outer receiver 304. FIGS. 29A and 29B illustrate the tool 274 having a handle 275 at the proximal end and distal tip having two oppositely disposed prongs 276 that are configured for engaging the oppositely disposed notches 370 of the inner receiver 308 to rotate it independently of the set screw 310. FIGS. 30A and 30B illustrates the tool 274 above the bone fixation system 200 such as the bone fixation system 300 with the distal prongs 276 substantially aligned with the notches 270. FIG. 31A illustrates the tool 274 with prongs 276 inserted into the notches 270 with the inner receiver 208 in an unlocked position and FIG. 32A illustrates the tool 274 with prongs 276 inserted into the notches 270 and the inner receiver 208 rotated into a locked position in which the arms 254 of the inner receiver 208 are engaging the threaded portions 232 of the outer receiver 204. FIGS. 31B and 32B illustrate the use of the tool 274 to lock the inner receiver relative to the outer receiver in the absence of the set screw.

Throughout this specification wherever threads, threaded portions or threaded engagements are mentioned, it is to be understood by one skilled in the art that the invention is not so limited and any coupling, locking or interlocking surface or mechanism known to one skilled in the art may be alternatively employed. For example, threaded engagement, twist-lock, snap-fit, friction fit, press-fit, ratcheting mechanism, or any friction locking system is within the scope of the present invention and may be substituted wherever such substitution is possible.

The ability to longitudinally translate the elongate fixation member relative to the outer receiver along the z-axis provides for a variation in the z-axis relation between the elongate fixation member and the bone fastener head. This advantageously allows for easier and more accurate placement of the elongate fixation member or rod, minimizing the amount of rod contouring required, while also minimizing the need for translating the vertebral body itself. Also, the system provides the surgeon with an easy way to simultaneously or independently, as needed, lock down the angulation of the tulip and the longitudinal and lateral position of the rod. These variable lockdown options afford the surgeon with greater flexibility, greater accuracy and greater ease in spinal fixation procedures.

The use of inner and outer receivers that move relative to each other, including multiple inner telescoping receivers, allow for translation when needed within the same confines of a traditional bone fixation assembly while at the same time permitting them to collapse to substantially the same height as a non-translating traditional bone fixation assembly when the translation is unnecessary. In this fashion, the amount that the screw head and rod construct protrudes above the bone surface is minimized leading to less injury to the soft tissues overlying the bone such as muscle and subcutaneous layers and resulting in less pain for the patient.

While z-axis translation can be achieved in some systems, those systems require partial manual assembly of the bone fixation assembly during surgery. Such a system requires increased operative time and increased steps of assembly. The present invention advantageously allows for pre-assembled screw heads, which simplifies the use of the system.

The present invention also advantageously provides the ability to lock the rod at multiple points along the z-axis using the same screw system. While z-axis translation can be achieved in some systems by using different screws with different head designs that secure the rod at different fixed points along the z-axis, such a system requires the surgeon to pre-plan and pre-select which screws will require exactly what amount of z-axis distance between the rod and screw and then to place the screws at the exact height that was pre-determined leaving the surgeon with fewer options for greater accuracy in-situ. The present invention allows for placement of screws of the same design in all vertebral bodies followed by adjustment of the z-axis translation as required at the time of securing the rod to the screw, rather than at the time of placing the screw into the bone.

The present invention also provides for the ability to lock the screw head and rod without transmitting force to the underlying vertebral body. Some systems lock the rod, head assembly, and screw with a locking mechanism that transmits force and/or torque to the underlying vertebral body. This force can be undesirable clinically as it can lead to fracturing of the bone, pullout of the screw, or deformation of the anatomy, among other outcomes. The present invention allows for the securing of all components while minimizing the force and/or torque transmitted to the underlying vertebral body.

Figure 44:
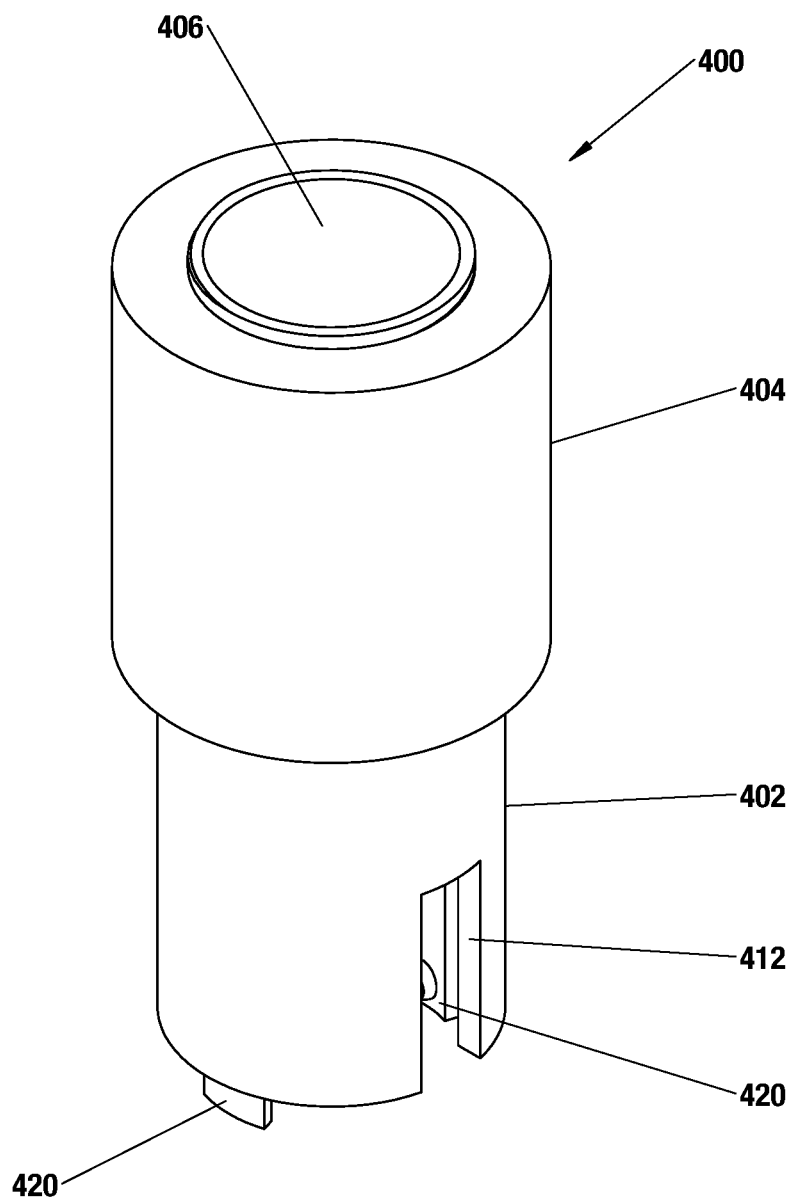
FIG. 44 is a top perspective view of a rod reduction instrument according to the present invention.
Figure 45:
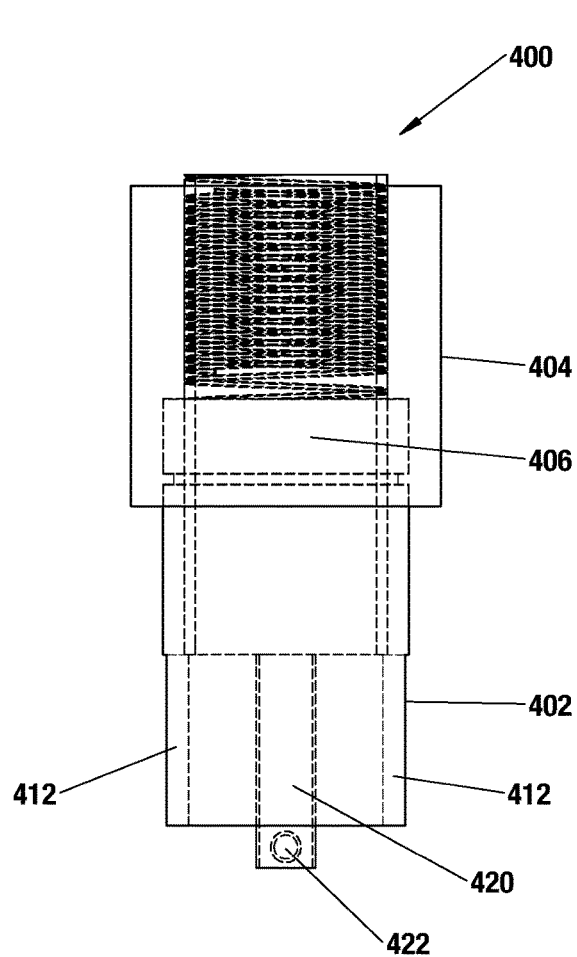
FIG. 45 is a side elevational, transparent view of a rod reduction instrument according to the present invention.
Figure 46:
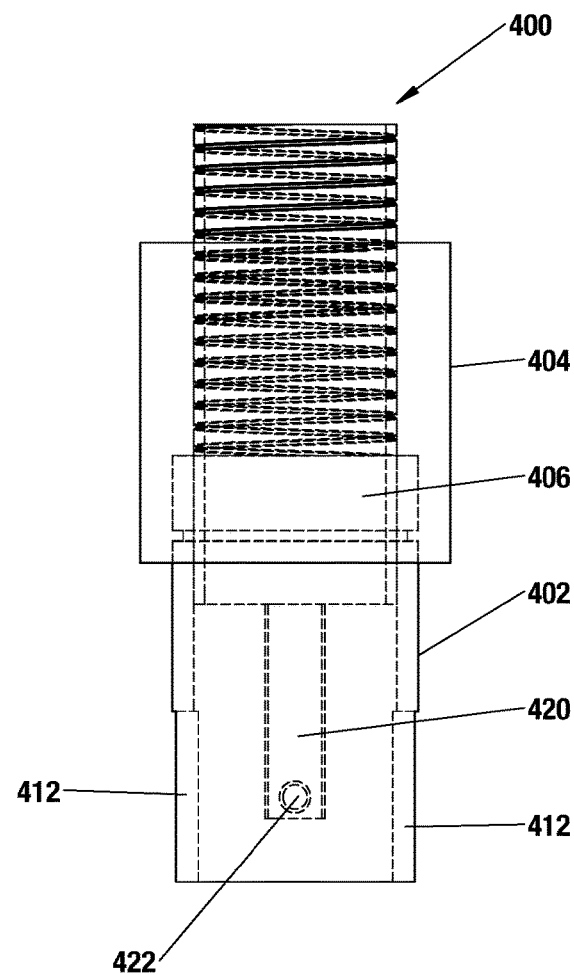
FIG. 46 is a side elevational, transparent view of a rod reduction instrument according to the present invention.

Turning now to FIGS. 43-46, there is shown a rod reduction instrument 400 according to the present invention. The rod reduction instrument 400 is configured to reduce the distance between an elongate fixation member such as a spinal fixation rod and the bone fastener in a bone fixation system of the like described above. The rod reduction instrument 400 includes a first cylinder 402 connected to a second cylinder 404 and a third cylinder 406 longitudinally movable with respect to the first and second cylinders 402, 404. The first cylinder 402 has a circular cross-section and a central lumen 408 extending between an opening at the proximal end and an opening at the distal end. The proximal end of the first cylinder 402 includes a circumferential groove configured for connecting with the second cylinder 404. The distal end of the first cylinder 402 includes two oppositely disposed rod-receiving channels 412. The rod-receiving channels 412 are sized and configured to receive an elongate fixation member such as a spinal fixation rod. The second cylinder 404 also has a circular cross-section and a central bore 414 extending between an opening at the proximal end and an opening at the distal end. The inner surface of the second cylinder 404 includes threads 416 that extend throughout the length of the central bore 414. The distal end of the second cylinder 404 is sized and configured for receiving the proximal end of the first cylinder 402. The first cylinder 402 is inserted into the distal end of the second cylinder 404 and connected thereto. The third cylinder 406 also has a circular cross-section and a central lumen 424 extending between an opening at the proximal and an opening at the distal end. The proximal end of the third cylinder 406 includes an outer surface with threads 418 along at least a portion of the longitudinal length of the outer surface. The distal end of the third cylinder 406 includes two oppositely disposed, distally extending prongs 420. The prongs 420 include radially inwardly extending nibs 422. The prongs 420 are spaced apart from each other and the nibs 422 are sized and configured to be inserted into holes formed in the outer surface of the outer receiver or outer tulip such as the holes 235 shown in FIGS. 20, 23, 24, 27, 28, 30B, 33A, and 34 and holes 335 shown in FIGS. 36, 39B, 41B and 42B. The third cylinder 406 is inserted into the central lumen 408 of the first cylinder 402 and into the central bore 414 of the second cylinder 404 and threading engaged with the second cylinder 404 such that the threads 418 of the third cylinder 406 are threadingly connected to the threads 416 on the inner surface of the second cylinder 404 as shown in FIGS. 44-46. FIG. 45 illustrates the rod reduction instrument 400 with the prongs 420 extending beyond the distal end of the first cylinder 402. Rotation of the second cylinder 404 draws the third cylinder 406 upwardly as it is connected with threads to the second cylinder 404. The third cylinder 406 in a proximal position relative to the first cylinder 402 is depicted in FIG. 46. The prongs 402 may be configured such that they have a tendency to splay radially outwardly when not confined within the central lumen 408 of the first cylinder 402. The splaying of prongs 420 makes it easier to connect the rod reduction instrument 400 to a bone fixation system.

Figure 49B:
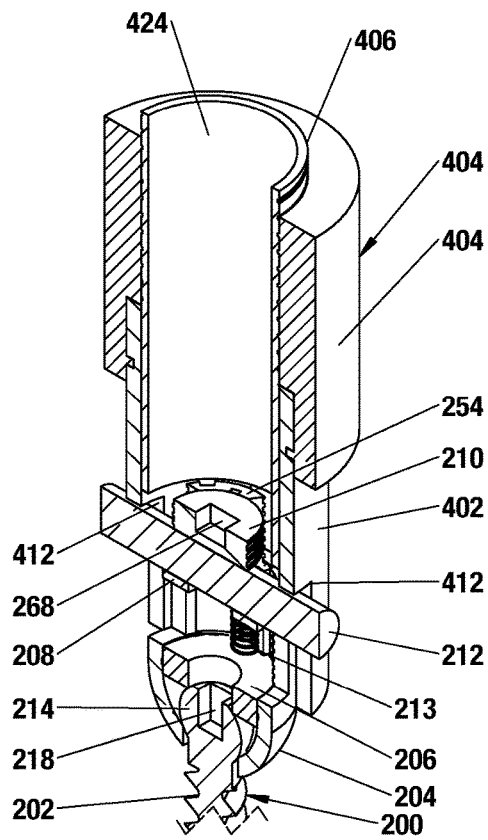
FIG. 49B is a cross-sectional view taken along line 49B-49B of FIG. 49A of a bone fixation system and rod reduction instrument according to the present invention.
Figure 50B:
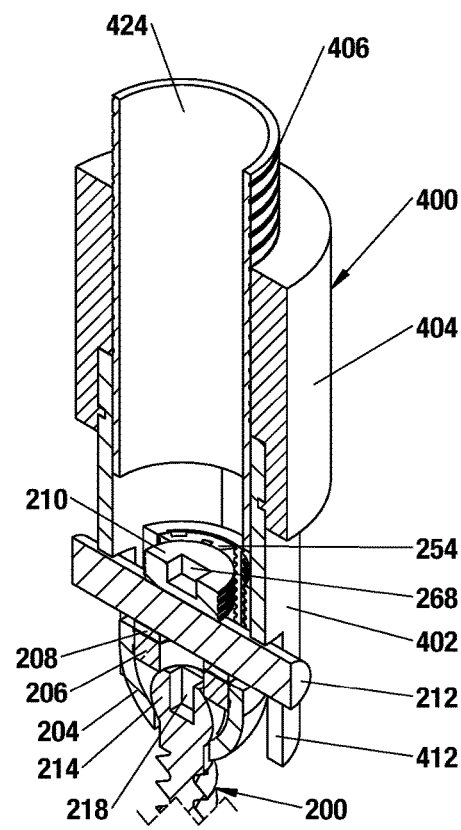
FIG. 50B is a cross-sectional view taken along line 50B-50B of FIG. 50A of a bone fixation system and rod reduction instrument according to the present invention.
Figure 49A:
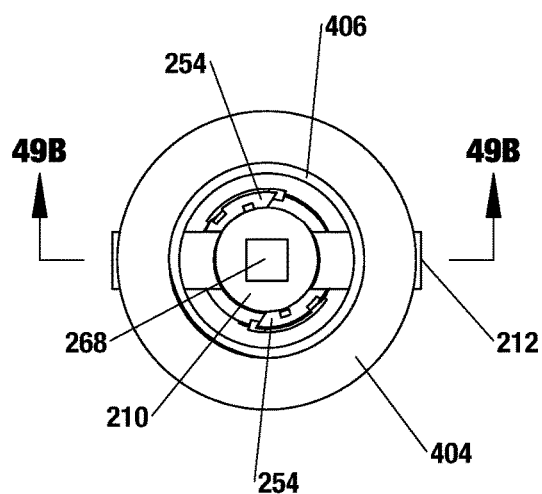
FIG. 49A is a top view of bone fixation system and rod reduction instrument according to the present invention.
Figure 50A:
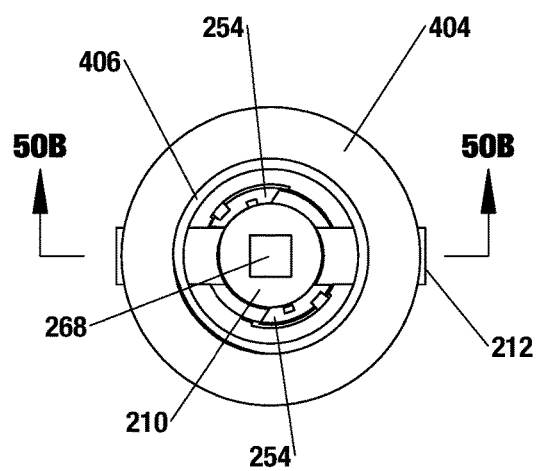
FIG. 50A is a top view of bone fixation system and rod reduction instrument according to the present invention.
Figure 51:
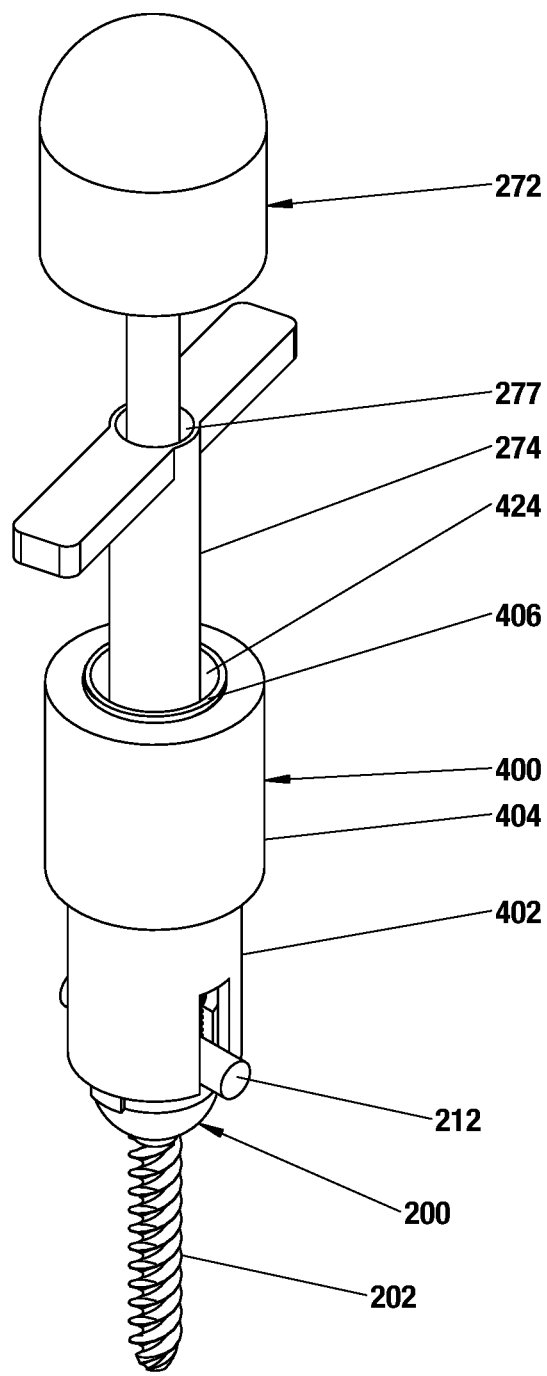
FIG. 51 is a top perspective view of a bone fixation system, rod reduction instrument, tool, and driver instrument according to the present invention.

In use, the rod reduction instrument 400 is manipulated so that the prongs 420 extend beyond the distal end of the first cylinder 402. The rod reduction instrument 400 is then brought into proximity above a target bone fixation assembly of the like described above and connected thereto by inserting the nibs 422 of the prongs 420 into holes such as the holes 235, 335. The elongate fixation member 212 that is associated with the target bone fixation assembly 200 is placed within the rod receiving channels 412 of the first cylinder 402. The second cylinder 404 is rotated from a position shown in FIGS. 47A, 47B, 49A, 49B to a position shown in FIGS. 48A, 48B, 50A, 50B in which the elongate fixation member 212 is drawn closer to the bone fastener 202. The set screw 210 may be rotated to lock the relative position of the rod 212 to the outer receiver 204. FIG. 51 illustrates the rod reduction instrument 400 connected to a bone fixation system 200 with a tool 274 inserted through the central lumen 424 of the third cylinder 406 and into connection with the inner receiver 208. In particular, the prongs 276 at the distal end of the tool 274 are inserted into notches 270 of the inner receiver 208. With the tool 274 connected to the inner receiver 208, the tool 274 can be rotated to lock the longitudinal, z-axis position of the inner receiver 208 and hence the rod 212 relative to the outer receiver 204. Still referencing FIG. 51, the driver instrument 272 is also inserted into the central lumen 277 of the tool 274 and passed through the rod reduction instrument 400 to engage the socket 268 of the set screw 210. Rotation of the set screw 210 with the driver instrument 272 would further lock the rod 212 relative to the inner receiver 208. Typically the anatomy is manipulated relative to the bone fixation system 200 as the elongate fixation member 212 is connected at its other end to another bone fixation system 200 implanted in another vertebra. With such manipulation, placement of the elongate fixation rod 212 would require readjustment of the position of the rod 212 relative to the outer receiver 204. The tool 274 would be rotated to unlock the inner receiver 208 from the outer receiver 204 such that it is free to translate along the z-axis. At such point the second cylinder 404 of the rod reduction instrument 400 can be rotated to further draw the rod 212 closer to the bone fastener 202 or further downwardly within the outer receiver 204 as shown in FIGS. 50A and 50B. While FIGS. 49A and 49B illustrate the inner receiver 208 unlocked from the outer receiver 204, FIGS. 50A and 50B illustrate the inner receiver 208 and rod 212 further reduced relative to the outer receiver 204. The positions are locked by the rotation of the inner receiver 208 relative to the outer receiver 204 by way of the either the driver instrument 272 or the tool 274. This process of reducing the distance between the rod 212 and the bone fastener 202 or otherwise drawing or seating the rod 212 downwardly into the outer receiver 204 and then locking the newly reduced position by turning the inner receiver 208 relative to the outer receiver 204 independently of the set screw 210 with the tool 274 or by turning the set screw 210 with driver 272 until the inner receiver 208 rotates into a locked position relative to the outer receiver 204 or both can be repeated as needed by unlocking either the set screw 210 or the inner receiver 208 relative to the outer receiver 204 and then readjusting the position of the rod 212 or further reducing the rod 212 relative to the outer receiver 204. It should be repeated that bone fixation system of the present invention advantageously allows the outer receiver 204 to be locked and unlocked relative to the bone fastener 202 to also adjust and readjust the angulation of the bone fastener 202 relative to the outer receiver 204 simultaneously with the reduction of the rod 212 or not according to surgeon preference. Hence, the bone fixation systems of the present invention are highly versatile suiting all the needs of the surgeon in complex spinal surgeries.

It will be understood that many modifications can be made to the various disclosed embodiments without departing from the spirit and scope of the concept. For example, various sizes of the surgical devices are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention.

We claim:

1. A bone fixation system, comprising:
an outer receiver including a sidewall that defines an inner bore and an open proximal end; the sidewall has an inner surface and an outer surface that define at least one channel in the proximal end opening to the inner bore and the open proximal end; the outer receiver includes an interlocking inner surface formed on the inner surface;
an inner receiver including a sidewall that defines an interior, an open proximal end, and an inner base at a distal end; the sidewall having an inner surface and an outer surface that defines at least one channel in the proximal end opening to the interior and the open proximal end; the inner receiver includes an interlocking inner surface formed on the inner surface; the inner receiver being located inside the outer receiver such that the at least one channel of the inner receiver is substantially aligned with the at least one channel of the outer receiver; the inner receiver being movable along a longitudinal axis relative to the outer receiver in an unlocked position;
a locking cap having an interlocking outer surface; the locking cap being located in the inner receiver and interlocked with the interlocking inner surface of the outer receiver and the interlocking inner surface of the inner receiver in a locked position wherein longitudinal translation of the inner receiver is fixed relative to the outer receiver.

2. The bone fixation system of claim 1 wherein the locking cap rotates from an unlocked position to the locked position to engage the interlocking outer surface of the locking cap simultaneously with the interlocking inner surface of the outer receiver and the interlocking inner surface of the inner receiver.

3. The bone fixation system of claim 1 wherein the inner surface of the outer receiver defines at least one translation surface adjacent to the interlocking inner surface of the outer receiver; the inner receiver being located within the outer receiver adjacent to the translation surface.

4. The bone fixation system of claim 3 wherein the translation surface extends longitudinally and is laterally adjacent to the interlocking inner surface of the outer receiver.

5. The bone fixation system of claim 1 wherein the channel of the outer receiver has a U-like shape and the channel of the inner receiver has a U-like shape.

6. A bone fixation system, comprising:
an outer receiver including a sidewall that defines an inner bore and an open proximal end; the sidewall has an inner surface and an outer surface that define at least one channel opening to the inner bore and the open proximal end; the outer receiver includes an interlocking inner surface formed on the inner surface;
an inner receiver including a sidewall that defines an interior, an open proximal end, and an inner base at a distal end; the sidewall having an inner surface and an outer surface that defines at least one channel opening to the interior and the open proximal end; the inner receiver includes an interlocking inner surface formed on the inner surface; the inner receiver being located inside the outer receiver such that the at least one channel of the inner receiver is substantially aligned with the at least one channel of the outer receiver; the inner receiver being movable along a longitudinal axis relative to the outer receiver in an unlocked position;
a locking cap having an interlocking outer surface; the locking cap being located in the inner receiver and interlocked with the interlocking inner surface of the outer receiver and the interlocking inner surface of the inner receiver in a locked position wherein longitudinal translation of the inner receiver is fixed relative to the outer receiver;
wherein the inner surface of the outer receiver defines at least one translation surface laterally adjacent to the interlocking inner surface of the outer receiver; the inner receiver being located within the outer receiver adjacent to the translation surface.

7. The bone fixation system of claim 6 wherein the translation surface is configured such that the interlocking inner surface of the outer receiver and the interlocking inner surface of the inner receiver are flush to provide a smooth transition between them for unimpeded locking engagement.

8. The bone fixation system of claim 6 wherein the interlocking inner surface of the outer receiver, the interlocking inner surface of the inner receiver and the interlocking outer surface of the locking cap are threaded and when the locking cap is inserted at the proximal end, the interlocking outer surface of the locking cap threads into both the interlocking inner surface of the outer receiver and the interlocking inner surface of the inner receiver substantially at the same time.

9. The bone fixation system of claim 6 wherein the translation surface is smooth.

10. The bone fixation system of claim 6 wherein the translation surface is recessed into the inner surface of the outer receiver.

11. The bone fixation system of claim 10 wherein the inner receiver is located in the recessed translation surface.

12. The bone fixation system of claim 6 wherein the translation surface extends longitudinally vertically and the interlocking inner surface of the outer receiver extends longitudinally vertically.

* * * * *